United States Patent
Cote et al.

(10) Patent No.: US 12,297,220 B2
(45) Date of Patent: May 13, 2025

(54) PHENETHYLAMINES AND CATHINONES PRECURSORS

(71) Applicant: Transcend Therapeutics, Inc., New York, NY (US)

(72) Inventors: Bernard Cote, Notre-Dame-de-l'Ile-Perrot (CA); Jennifer Schmidt, Garden City, NY (US); Martin Stogniew, Lakewood Ranch, FL (US)

(73) Assignee: TRANSCEND THERAPEUTICS, INC., New York, NY (US)

( * ) Notice: Subject to any disclaimer, the term of this patent is extended or adjusted under 35 U.S.C. 154(b) by 0 days.

(21) Appl. No.: 18/955,261

(22) Filed: Nov. 21, 2024

(65) Prior Publication Data

US 2025/0129108 A1    Apr. 24, 2025

Related U.S. Application Data

(63) Continuation of application No. PCT/US2023/030140, filed on Aug. 14, 2023.

(Continued)

(51) Int. Cl.
*C07F 9/655* (2006.01)
*A61K 9/00* (2006.01)
(Continued)

(52) U.S. Cl.
CPC ........ *C07F 9/65517* (2013.01); *A61K 9/0019* (2013.01); *A61K 9/0053* (2013.01); *A61K 31/665* (2013.01); *C07D 317/48* (2013.01)

(58) Field of Classification Search
CPC .. C07F 9/65517; C07D 317/48; A61K 31/665
See application file for complete search history.

(56) References Cited

U.S. PATENT DOCUMENTS

| | | |
|---|---|---|
| 3,536,809 A | 10/1970 | Applezweig |
| 3,845,770 A | 11/1974 | Theeuwes et al. |

(Continued)

FOREIGN PATENT DOCUMENTS

| | | |
|---|---|---|
| PL | 232830 | 7/2019 |
| WO | WO 1996/039133 | 12/1996 |

(Continued)

OTHER PUBLICATIONS

International Search Report and Written Opinion, dated Jan. 26, 2024, from corresponding International Application No. PCT/US23/30140.

(Continued)

*Primary Examiner* — Sarah Pihonak
*Assistant Examiner* — Padmaja S Rao
(74) *Attorney, Agent, or Firm* — PEARL COHEN ZEDEK LATZER BARATZ LLP

(57) ABSTRACT

The subject matter disclosed generally relates to phenethylamines or cathinones covalently bound to a chemical moiety in a prodrug form. The presently described technology allows slow/sustained/controlled delivery of the parent phenethylamines or cathinones into the blood system in a manner that increase the duration of therapeutic efficacy, ease of application, patient compliance and/or a combination of these characteristics when administered, in particular, orally. Additionally, the described technology allows gradual release of the parent phenethylamines or cathinones over an extended period of time thereby eliminating spiking of drug levels which lessen cardiovascular stress, addiction/abuse potential and/or other common stimulant side effects associated with psychoactive compounds.

8 Claims, 1 Drawing Sheet

Related U.S. Application Data

(60) Provisional application No. 63/471,369, filed on Jun. 6, 2023, provisional application No. 63/398,703, filed on Aug. 17, 2022.

(51) Int. Cl.
*A61K 31/665* (2006.01)
*C07D 317/48* (2006.01)

(56) References Cited

U.S. PATENT DOCUMENTS

| | | | |
|---|---|---|---|
| 3,916,899 | A | 11/1975 | Theeuwes et al. |
| 5,059,595 | A | 10/1991 | Le Grazie |
| 7,105,486 | B2 | 9/2006 | Mickle et al. |
| 7,662,787 | B2 | 2/2010 | Mickle et al. |
| 2007/0155729 | A1 | 7/2007 | Morgan et al. |
| 2010/0160666 | A1 | 6/2010 | Ben Moha-Lerman et al. |
| 2015/0274670 | A1 | 10/2015 | Remenar et al. |
| 2017/0145044 | A1 | 5/2017 | Hudson et al. |

FOREIGN PATENT DOCUMENTS

| | | | | |
|---|---|---|---|---|
| WO | WO 2020/008064 | | 1/2020 | |
| WO | WO 2022/053696 | | 3/2022 | |
| WO | WO-2022053696 | A1 * | 3/2022 | ............... A61P 25/00 |
| WO | WO 2023/137453 | | 7/2023 | |
| WO | WO-2023137453 | A1 * | 7/2023 | ............... A61P 25/00 |

OTHER PUBLICATIONS

Elmore et al., "Pharmacokinetic Profiles and Pharmacodynamic Effects for Methylone and Its Metabolites in Rats", Neuropsychopharmacology (2017) 42: 649-660.
Rautio et al., "The expanding role of prodrugs in contemporary drug design and development", Nat. Rev. Drug Discov. (2018) 17:559.
Heather et al., "Organic impurity profiling of methylone and intermediate compounds synthesized from catechol", Drug Test Analysis (2017) 9:436-445.
Mahuex et al. "Identification of polymorphism in ethylone hydrochloride: synthesis and characterization", Drug Test Analysis (2016) 8:847-857.
Maheux et al., "Chemical analysis of two new designer drugs: buphedrone and pentedrone", Drug Test Analysis (2012) 4:17-23.
Milhazes et al., "Electrochemical and spectroscopic characterisation of amphetamine-like drugs: Application to the screening of 3,4-methylenedioxymethamphetamine (MDMA) and its synthetic precursors", Analytica Chimica Acta, Jul. 2007, 596(2): 231-241.
Safadi et al., "Phosphoryloxymethyl Carbamates and Carbonates—Novel Water-Soluble Prodrugs for Amines and Hindered Alcohols", Pharmaceutical Research, 1993, 10(9):1350-1355.
Nicolaou et al., "Phosphate Prodrugs for Amines Utilizing a Fast Intramolecular Hydroxy Amide Lactonization", J. Org. Chem. 1996, 61(24): 8636-8641.
Crouch, "Selective deprotection of silyl ethers", Tetrahedron, Mar. 2013, 69(11):2383-2417.
Liao et al., "Substituted coumarins as esterase-sensitive prodrug moieties with improved release rates", Bioorganic & Medicinal Chemistry Letters, Jul. 1999, 9(13):1795-1800.
Porsolt et al., "Depression: a new animal model sensitive to antidepressant treatments", Nature (1977) 266:730-732.
Detke et al., "Active behaviors in the rat forced swimming test differentially produced by serotonergic and noradrenergic antidepressants", Psychopharmacology, Sep. 1995, 121:66-72.
Wicking et al., "Deficient fear extinction memory in posttraumatic stress disorder", Neurobiology of Learning and Memory, Dec. 2016, 136:116-126.
Pedraza et al., "Chronic fluoxetine prevents fear memory generalization and enhances subsequent extinction by remodeling hippocampal dendritic spines and slowing down systems consolidation", Transl. Psychiatry (2019) 9:53.
Feduccia et al., "MDMA-assisted psychotherapy for PTSD: Are memory reconsolidation and fear extinction underlying mechanisms?", Progress in Neuro-Psychopharmacology and Biological Psychiatry, Jun. 2018, vol. 84, Part A, pp. 221-228.
Young et al., "3,4-Methylenedioxymethamphetamine facilitates fear extinction learning", Transl. Psychiatry, Sep. 2015, 5: e634.
Stefkova et al., "Pharmacokinetic, Ambulatory, and Hyperthermic Effects of 3,4-Methylenedioxy-N-Methylcathinone (Methylone) in Rats", Front. Psychiatry, Nov. 2017, vol. 8, Article 232.
Warner-Schmidt et al., "Methylone, a rapid acting entactogen with robust anxiolytic and antidepressant-like activity", Front. Psychiatry, Jan. 9, 2023; 13:1041277.
Yu et al., "The Medial Prefrontal Cortex, Nucleus Accumbens, Basolateral Amygdala, and Hippocampus Regulate the Amelioration of Environmental Enrichment and Cue in Fear Behavior in the Animal Model of PTSD", Behavioural Neurology, Feb. 7, 2022; vol. 2022, Article ID 7331714, 14 pages.
Cuijpers et al., "A network meta-analysis of the effect of psychotherapies, pharmacotherapies and their combination in the treatment of adult depression", World Psychiatry, Feb. 2020; 19:92-107.

* cited by examiner

PHENETHYLAMINES AND CATHINONES PRECURSORS

CROSS-REFERENCE TO RELATED APPLICATIONS

This application is a continuation of International Application No. PCT/US2023/030140, filed Aug. 14, 2023, which claims the benefit of U.S. Provisional Applications Nos. 63/398,703, filed Aug. 17, 2022, and 63/471,369, filed Jun. 6, 2023, which are hereby incorporated by reference.

FIELD OF THE INVENTION

The subject matter disclosed generally relates to phenethylamines or cathinones covalently bound to a chemical moiety in a prodrug form. The presently described technology allows slow/sustained/controlled delivery of the parent phenethylamines or cathinones into the blood system in a manner that increase the duration of therapeutic efficacy, ease of application, patient compliance and/or a combination of these characteristics when administered, orally in particular. Additionally, the described technology allows gradual release of the parent phenethylamines or cathinones over an extended time period, thereby eliminating spiking of drug levels which lessen cardiovascular stress, addiction/abuse potential and/or other common stimulant side effects associated with psychoactive compounds.

BACKGROUND OF THE INVENTION

Methylone (3,4-methylenedioxy-N-methylacthinone) belongs to the group of psychoactive active synthetic cathinones known as β-keto amphetamine. It is a synthetic analog of MDMA that differs by the presence of a ketone at the benzylic position. First synthesized in 1996 as an antidepressant and anti-Parkinsonian, methylone is a recreational street drug. It induces psychostimulant and empathogenic effects similar to MDMA with a mechanism of action that involve the monoaminergic system.

MDMA (3,4-methylenedioxymethamphetamine, commonly known as ecstasy, is a psychoactive drug primarily used for recreational purposes. MDMA acts primarily by increasing the activity of the neurotransmitters serotonin, dopamine and noradrenaline in parts of the brain. In 2017, the United States Food and Drug Administration (FDA) approved limited research on MDMA-assisted psychotherapy for post-traumatic stress disorder (PTSD), with some preliminary evidence that MDMA may facilitate psychotherapy efficacy.

Despite its close structural analogy with MDMA, methylone has distinct pharmacological and functional properties. Methylone has been shown to improve symptoms of PTSD in 81% of patients in a clinical case series of 21 individuals. Currently, the only approved treatments for PTSD are the serotonergic antidepressants sertraline and paroxetine, so drugs that show antidepressant-like activity should improve PTSD symptoms. Methylone has the strongest effect possible in the classic preclinical screen of antidepressant activity, the forced swim test. Methylone also shows benefit in a PTSD mouse model, improving fear extinction recall after fear conditioning, which is consistent with a therapeutic response in this test. Together with the results of the clinical case series, these data strongly support the potential for clinically effective treatment of PTSD.

Methylone consumers have reported a rapid 15-30 minutes onset of action and a short 2-3.5 hours duration. In a prospective observational-naturalistic study (Lourdes et al. (2021) *Biology* 10:788) comparing healthy volunteers self-administration of methylone and MDMA, a significant increase in systolic and diastolic blood pressure was observed for both drugs while only methylone was associated with an increase in heart rate. Subjects reported stimulant-like effects starting at 1 hour post-dosing while most of these effects had almost disappeared after 4 hours.

Parent and metabolites analysis from human and rat urine samples showed a similar metabolic pathway for methylone and MDMA. They are both extensively biotransformed by the cytochrome p450 isoform 2D6 which is in line with their rapid kinetic and short duration of action. In rat PK/PD studies, methylone displayed a rapid kinetic with a $T_{Max}$ of 15 minutes and a $t_{1/2}$ of 1 hour (Elmore et al. (2017) *Neuropsychopharmacology* 42:649). In the same study, it appears that the methylone plasma concentration correlates with locomotor activation.

As an alternative to sustained released formulations, prodrugs have been used to extend the duration of action and reduce the toxicity and/or side effects associated with the initial spiking of drug levels. Examples of such prodrugs can be found in U.S. Pat. No. 7,105,486 B2 and WO 2022/053696 where the amine functionality of d-amphetamine and MDMA has been covalently linked to an amino acid to form an amide bond. In the case of d-amphetamine, the resulting L-Lysine conjugated prodrug known as lisdexamfetamine, displayed a longer duration of action of 10-12 hours compared to 3-6 hours for the unconjugated form of d-amphetamine. A more favorable toxicity/tolerability profile has also been reported for lisdexamfetamine compared to the unconjugated form of d-amphetamine and can be attributed, but not limited to a significant decrease of the prodrug pharmacological activity due to structure modification, a natural gating mechanism at the site of hydrolysis that limits the release of the active amphetamine from the prodrug, and a lack of brain permeability of the prodrug.

Amino groups, such as the one found in methylone or MDMA, can be derivatized to different conjugate prodrugs which are characterized by the newly formed functional group and its specific conversion process to liberate the active drug. Examples of conjugated amine prodrugs such as amide prodrugs, peptide or polypeptide prodrugs, carbamate prodrugs, acyloxyalkoxycarbonyl prodrugs, acyloxymethyl prodrugs, phosphoramide prodrugs and phosphoryloxyalkyl prodrugs can be found in Rautio et al. (2018) *Nat. Rev. Drug Discov.* 17:559.

It is therefore an object of the present invention to provide a psychoactive agent that displays an advantageous pharmacokinetic and/or pharmacodynamic profile for the treatment of CNS disorder such as PTSD.

It is a further object of the invention to provide a psychoactive agent that would display a favorable toxicity and/or tolerability profile for the treatment of CNS disorders such as PTSD.

It is a further object of the invention to provide prodrugs of a phenethylamine such as MDMA or prodrugs of a cathinone such as methylone that can be hydrolyzed after absorption and be converted directly to the therapeutically active form of the parent compounds.

SUMMARY OF THE INVENTION

The present invention is directed to compounds that are phenethylamine or cathinone precursors in a prodrug form. This invention also provides a pharmaceutical composition that includes an effective amount of the phenethylamine or cathinone precursor and a pharmaceutically acceptable carrier. This invention further provides a method of treatment in mammals of, for example, post-traumatic stress disorder (PTSD), anxiety disorder, attention deficit hyperactivity disorder (ADHD), obsessive compulsive disorder (OCD), fibromyalgia, depression, cluster headache, a condition associated with cancer, diminished drive, burn-out, bore-out, migraine, Parkinson's disease, pulmonary hypertension, schizophrenia, an eating disorder, nausea, or vomiting, by the administration of an effective amount of the phenethylamine or cathinone precursor.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

(FIG. 1A) Schematic of experimental design. A single CS—US (tone-shock) pairing on day 1 was followed by 6 CS presentations in a novel context (context B). Methylone or saline vehicle was injected 30 min prior to extinction training on day 2. On day 3, the time spent freezing to the CS was quantified. (FIG. 1B) Freezing time during the first cue on day 3 (extinction recall) was significantly reduced by methylone compared to saline ($t_{(26)}=2.350$, $p<0.05$). (FIG. 1C) The time freezing before vs. during each of 6 cues on day 3 (to control for locomotor effects) are shown. There was a significant cue×drug interaction ($F_{(5, 130)}=2.409$, $p<0.05$). (FIG. 1D) No locomotor changes were observed on day 3 ($t_{(26)}=1.073$, $p>0.05$). N=12 for methylone group (30 mg/kg, IP, orange diamonds) and N=16 for saline control group (black squares). *$p<0.05$

DETAILED DESCRIPTION OF THE INVENTION

Figure 1A:
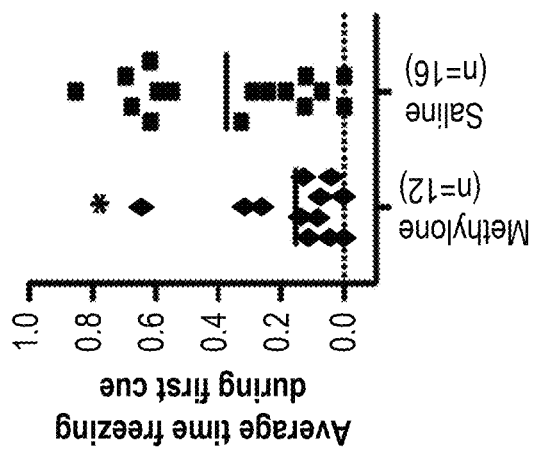
FIGS. 1A-1D: Methylone improves fear extinction recall in a mouse model of PTSD.

The present invention provides phenethylamine or cathinone prodrugs that exhibit advantageous pharmacokinetic properties and a beneficial side effect profile, which renders the compounds provided herein particularly well suitable for therapeutic use.

In one aspect, provided herein are compounds represented by Formula (I):

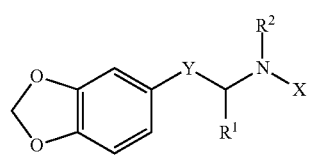
(I)

or a pharmaceutically acceptable salt thereof, wherein:
Y is —C(O)— or —CH$_2$—;
X is independently selected from the group consisting of:
(a) an amino acid or a peptide,
(b) —C(O)R$^3$,
(c) —C(O)OR$^3$,
(d) —C(O)OCH(R$^4$)OR$^5$,
(e) —CH$_2$OC(O)R$^3$,
(f) —P(O)(OH)$_2$,
(g) —CH$_2$OP(O)(OH)$_2$,
(h) —C(O)(CH$_2$)$_n$Z$^a$R$^5$,

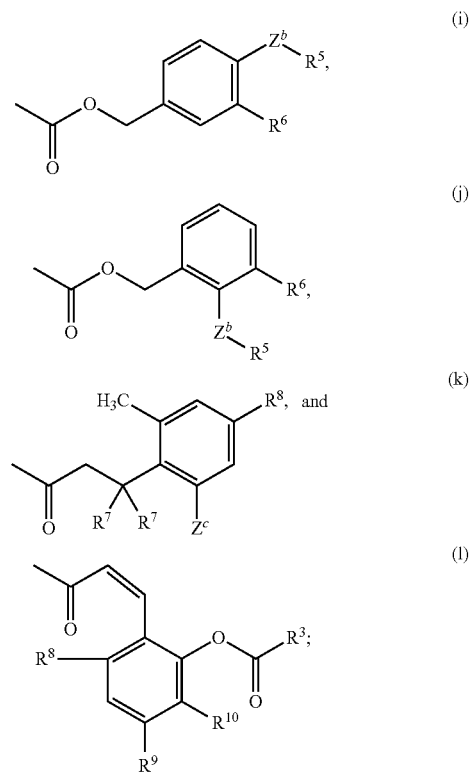

wherein:
n is 3 or 4;
R$^1$ and R$^2$ are each independently —C$_{1-6}$alkyl or —C$_{3-6}$cycloalkyl;
R$^3$ is selected from the group consisting of: —C$_{1-6}$alkyl, —C$_{3-6}$cycloalkyl, —C$_{1-6}$haloalkyl, aryl, heteroaryl,

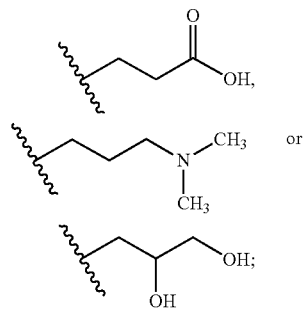

R$^4$, R$^7$, R$^8$, R$^9$ and R$^{10}$ are each independently H, —C$_{1-6}$alkyl or —C$_{3-6}$cycloalkyl;

$R^5$ is selected from the group consisting of: —C(O)R³, —C(O)OR³, —P(O)OR¹¹(OR¹²), an amino acid, and a peptide;

$Z^a$ and $Z^b$ are each independently O or NR⁴;

$Z^c$ is selected from: OC(O)R³ or OP(O)(OR⁴)₂;

$R^6$ is selected from the group consisting of: H, —C₁₋₆alkyl, —C₃₋₆cycloalkyl, alkoxy, amino, nitro, halo, cyano, —OH and CF₃;

$R^{11}$ and $R^{12}$ are each independently H, —C₁₋₆alkyl, —C₁₋₆heteroalkyl, —C₃₋₆cycloalkyl, —C₁₋₆haloalkyl, aryl or heteroaryl, wherein —C₁₋₆alkyl, —C₁₋₆heteroalkyl, —C₃₋₆cycloalkyl, —C₁₋₆haloalkyl, aryl or heteroaryl is unsubstituted or substituted with one or more —C₁₋₆alkyl, —C₁₋₆heteroalkyl, —C₃₋₆cycloalkyl, —C₁₋₆haloalkyl, aryl or heteroaryl.

In some embodiments of the foregoing compounds, $R^1$ and $R^2$ are each independently methyl or ethyl. In some embodiments, $R^4$ is H or methyl. In some embodiments, $Z^a$, is NH. In some embodiments, $Z^b$ is O or NH. In some embodiments, $Z^b R^5$ taken together is NO₂ or N₃. In some embodiments, $R^6$ is H, methyl, methoxy, nitro or chloro. In some embodiments, $R^7$ is methyl. In some embodiments, $R^8$, $R^9$, $R^{10}$, $R^{11}$ and $R^{12}$ are each independently H or methyl. In some embodiments, $R^{10}$ is methyl. In some embodiments, when Y is —CH₂—, X is not an amino acid, peptide, or —P(O)(OH)₂ group.

According to another embodiment, the compound of Formula (I) is a compound having the structure of Formula (III):

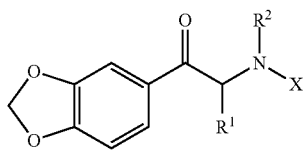
(III)

or a pharmaceutically acceptable salt thereof, wherein:
X is independently selected from the group consisting of:
(a) an amino acid or a peptide;
(b) —C(O)R³,
(c) —C(O)OR³,
(d) —C(O)OCH(R⁴)OR⁵,
(e) —CH₂OC(O)R³,
(f) —P(O)(OH)₂,
(g) —CH₂OP(O)(OH)₂,
(h) —C(O)(CH₂)ₙZ^aR⁵,

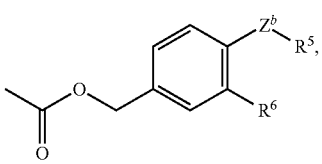
(i)

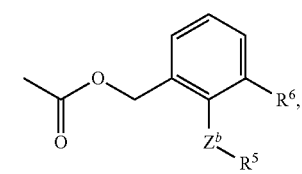
(j)

-continued

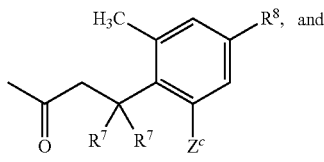
(k)

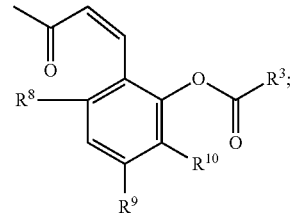
(l)

wherein:
n is 3 or 4;
$R^1$ and $R^2$ are each independently —C₁₋₆alkyl or —C₃₋₆cycloalkyl;
$R^3$ is selected from the group consisting of: —C₁₋₆alkyl, —C₃₋₆cycloalkyl, —C₁₋₆haloalkyl, aryl, heteroaryl,

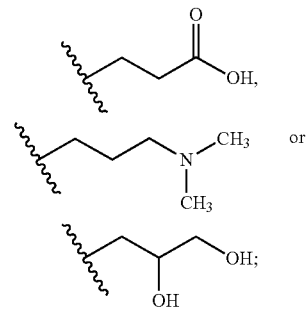

$R^4$, $R^7$, $R^8$, $R^9$ and $R^{10}$ are each independently H, —C₁₋₆alkyl or —C₃₋₆cycloalkyl;

$R^5$ is selected from the group consisting of: —C(O)R³, —C(O)OR³, —P(O)OR¹¹(OR¹²), an amino acid, and a peptide;

$Z^a$ and $Z^b$ are each independently O or NR⁴;

$Z^c$ is selected from: OC(O)R³ or OP(O)(OR⁴)₂;

$R^6$ is selected from the group consisting of: H, —C₁₋₆alkyl, —C₃₋₆cycloalkyl, alkoxy, amino, nitro, halo, cyano, —OH and CF₃;

$R^{11}$ and $R^{12}$ are each independently H, —C₁₋₆alkyl, —C₁₋₆heteroalkyl, —C₃₋₆cycloalkyl, —C₁₋₆haloalkyl, aryl or heteroaryl, wherein —C₁₋₆alkyl, —C₁₋₆heteroalkyl, —C₃₋₆cycloalkyl, —C₁₋₆haloalkyl, aryl or heteroaryl is unsubstituted or substituted with one or more —C₁₋₆alkyl, —C₁₋₆heteroalkyl, —C₃₋₆cycloalkyl, —C₁₋₆haloalkyl, aryl or heteroaryl.

In some embodiments of the foregoing compounds, $R^1$ and $R^2$ are each independently methyl or ethyl. In some embodiments, $R^4$ is H or methyl. In some embodiments, $Z^a$, is NH. In some embodiments, $Z^b$ is O or NH. In some embodiments, $Z^b R^5$ taken together is NO₂ or N₃. In some embodiments, $R^6$ is H, methyl, methoxy, nitro or chloro. In some embodiments, $R^7$ is methyl. In some embodiments, $R^8$, $R^9$, $R^{10}$, $R^{11}$ and $R^{12}$ are each independently H or methyl. In some embodiments, $R^{10}$ is methyl. In some embodiments, X is an amino acid. In some embodiments, the compound is selected from the group consisting of compounds 1-402 of Table 1, 2 and 3 below.

According to some embodiments, the compound of Formula (I) is a compound having the structure of Formula (IV):

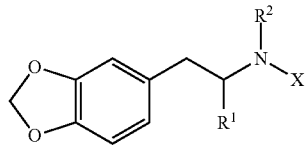
(IV)

or a pharmaceutically acceptable salt thereof, wherein:
X is independently selected from the group consisting of:
(a) —C(O)$R^3$,
(b) —C(O)O$R^3$,
(c) —C(O)OCH($R^4$)O$R^5$,
(d) —$CH_2$OC(O)$R^3$,
(e) —$CH_2$OP(O)(OH)$_2$,
(f) —C(O)($CH_2$)$_n$$Z^a$$R^5$,

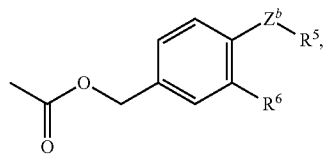
(g)

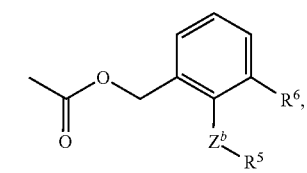
(h)

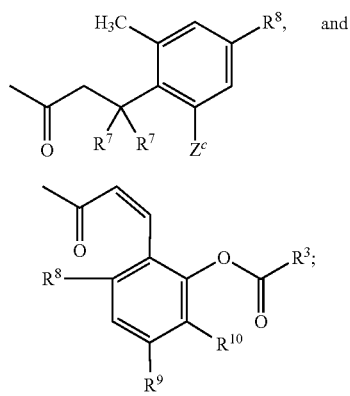
(i)

(j)

wherein:
n is 3 or 4;
$R^1$ and $R^2$ are each independently —$C_{1-6}$alkyl or —$C_{3-6}$cycloalkyl;
$R^3$ is selected from the group consisting of: —$C_{1-6}$alkyl, —$C_{3-6}$cycloalkyl, —$C_{1-6}$haloalkyl, aryl, heteroaryl,

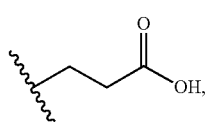

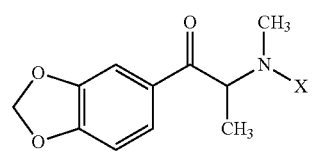
or

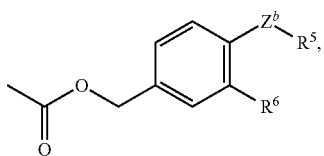
;

$R^4$, $R^7$, $R^8$, $R^9$ and $R^{10}$ are each independently H, —$C_{1-6}$alkyl or —$C_{3-6}$cycloalkyl;
$R^5$, is selected from the group consisting of: —C(O)$R^3$, —C(O)O$R^3$, —P(O)O$R^{11}$(O$R^{12}$), an amino acid, and a peptide;
$Z^a$ and $Z^b$ are each independently O or N$R^4$;
$Z^c$ is selected from: OC(O)$R^3$ or OP(O)(O$R^4$)$_2$;
$R^6$ is selected from the group consisting of: H, —$C_{1-6}$alkyl, —$C_{3-6}$cycloalkyl, alkoxy, amino, nitro, halo, cyano, —OH and $CF_3$;
$R^{11}$ and $R^{12}$ are each independently H, —$C_{1-6}$alkyl, —$C_{1-6}$heteroalkyl, —$C_{3-6}$cycloalkyl, —$C_{1-6}$haloalkyl, aryl or heteroaryl, wherein —$C_{1-6}$alkyl, —$C_{1-6}$heteroalkyl, —$C_{3-6}$cycloalkyl, —$C_{1-6}$haloalkyl, aryl or heteroaryl is unsubstituted or substituted with one or more —$C_{1-6}$alkyl, —$C_{1-6}$heteroalkyl, —$C_{3-6}$cycloalkyl, —$C_{1-6}$haloalkyl, aryl or heteroaryl.

In some embodiments of the foregoing compounds, $R^1$ and $R^2$ are each independently methyl or ethyl. In some embodiments, $R^4$ is H or methyl. In some embodiments, $Z^a$, is NH. In some embodiments, $Z^b$ is O or NH. In some embodiments, $Z^b R^5$ taken together is $NO_2$ or $N_3$. In some embodiments, $R^6$ is H, methyl, methoxy, nitro or chloro. In some embodiments, $R^7$ is methyl. In some embodiments, $R^8$, $R^9$, $R^{10}$, $R^{11}$ and $R^{12}$ are each independently H or methyl. In some embodiments, $R^{10}$ is methyl.

According to some embodiments, the compound of Formula (I) is a compound having the structure of Formula (V):

(V)

or a pharmaceutically acceptable salt thereof, wherein:
X is independently selected from the group consisting of:
(a) an amino acid or a peptide;
(b) —C(O)$R^3$,
(c) —C(O)O$R^3$,
(d) —C(O)OCH($R^4$)O$R^5$,
(e) —$CH_2$OC(O)$R^3$,
(f) —P(O)(OH)$_2$,
(g) —$CH_2$OP(O)(OH)$_2$,
(h) —C(O)($CH_2$)$_n$$Z^a$$R^5$, (i)

-continued

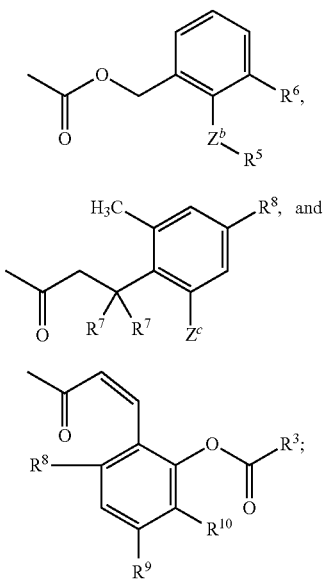

(j)

(k)

(l)

wherein:
n is 3 or 4;
R³ is selected from the group consisting of: —C₁₋₆alkyl, —C₃₋₆cycloalkyl, —C₁₋₆haloalkyl, aryl, heteroaryl,

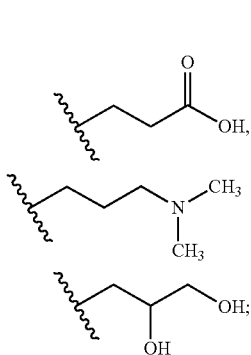

R⁴, R⁷, R⁸, R⁹ and R¹⁰ are each independently H, —C₁₋₆alkyl or —C₃₋₆cycloalkyl;
R⁵ is selected from the group consisting of: —C(O)R³, —C(O)OR³, —P(O)OR¹(OR¹²), an amino acid, and a peptide;
$Z^a$ and $Z^b$ are each independently O or NR⁴;
$Z^c$ is selected from: OC(O)R³ or OP(O)(OR⁴)₂;
R⁶ is selected from the group consisting of: H, —C₁₋₆alkyl, —C₃₋₆cycloalkyl, alkoxy, amino, nitro, halo, cyano, —OH and CF₃;
R¹¹ and R¹² are each independently H, —C₁₋₆alkyl, —C₁₋₆heteroalkyl, —C₃₋₆cycloalkyl, —C₁₋₆haloalkyl, aryl or heteroaryl, wherein —C₁₋₆alkyl, —C₁₋₆heteroalkyl, —C₃₋₆cycloalkyl, —C₁₋₆haloalkyl, aryl or heteroaryl is unsubstituted or substituted with one or more —C₁₋₆alkyl, —C₁₋₆heteroalkyl, —C₃₋₆cycloalkyl, —C₁₋₆haloalkyl, aryl or heteroaryl.

In some embodiments of the foregoing compounds, R⁴ is H or methyl. In some embodiments, $Z^a$ is NH. In some embodiments, $Z^b$ is O or NH. In some embodiments, $Z^bR^5$ taken together is NO₂ or N₃. In some embodiments, R⁶ is H, methyl, methoxy, nitro or chloro. In some embodiments, R⁷ is methyl. In some embodiments, R⁸, R⁹, R¹⁰, R¹¹ and R¹² are each independently H or methyl. In some embodiments, R¹⁰ is methyl. In some embodiments, X is an amino acid.

According to some embodiments, the compound of Formula (I) is a compound having the structure of Formula (VI):

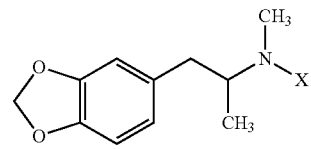

(VI)

or a pharmaceutically acceptable salt thereof, wherein:
X is independently selected from the group consisting of:
(a) —C(O)R³,
(b) —C(O)OR³,
(c) —C(O)OCH(R⁴)OR⁵,
(d) —CH₂OC(O)R³,
(e) —CH₂OP(O)(OH)₂,
(f) —C(O)(CH₂)ₙZ^aR⁵,

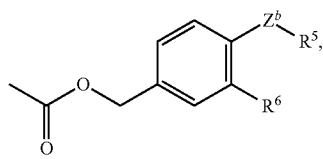

(g)

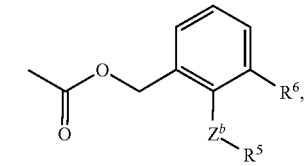

(h)

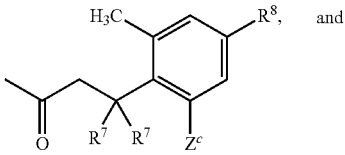

(i)

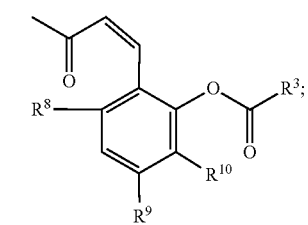

(j)

wherein:
n is 3 or 4;
R³ is selected from the group consisting of: —C₁₋₆alkyl, —C₃₋₆cycloalkyl, —C₁₋₆haloalkyl, aryl, heteroaryl,

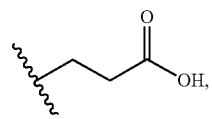

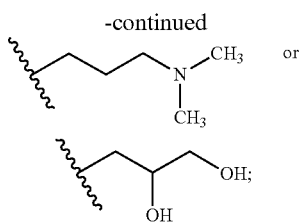

$R^4$, $R^7$, $R^8$, $R^9$ and $R^{10}$ are each independently H, —$C_{1-6}$alkyl or —$C_{3-6}$cycloalkyl;

$R^5$, is selected from the group consisting of: —C(O)$R^3$, —C(O)O$R^3$, —P(O)O$R^{11}$(O$R^{12}$), an amino acid, and a peptide;

$Z^a$ and $Z^b$ are each independently O or N$R^4$;

$Z^c$ is selected from: OC(O)$R^3$ or OP(O)(O$R^4$)$_2$;

$R^6$ is selected from the group consisting of: H, —$C_{1-6}$alkyl, —$C_{3-6}$cycloalkyl, alkoxy, amino, nitro, halo, cyano, —OH and C$F_3$;

$R^{11}$ and $R^{12}$ are each independently H, —$C_{1-6}$alkyl, —$C_{1-6}$heteroalkyl, —$C_{3-6}$cycloalkyl, —$C_{1-6}$haloalkyl, aryl or heteroaryl, wherein —$C_{1-6}$alkyl, —$C_{1-6}$heteroalkyl, —$C_{3-6}$cycloalkyl, —$C_{1-6}$haloalkyl, aryl or heteroaryl is unsubstituted or substituted with one or more —$C_{1-6}$alkyl, —$C_{1-6}$heteroalkyl, —$C_{3-6}$cycloalkyl, —$C_{1-6}$haloalkyl, aryl or heteroaryl.

In some embodiments, $R^4$ is H or methyl. In some embodiments, $Z^a$, is NH. In some embodiments, $Z^b$ is O or NH. In some embodiments, $Z^b R^5$ taken together is NO$_2$ or N$_3$. In some embodiments, $R^6$ is H, methyl, methoxy, nitro or chloro. In some embodiments, $R^7$ is methyl. In some embodiments, $R^1$, $R^9$, $R^{10}$, $R^{11}$ and $R^{12}$ are each independently H or methyl. In some embodiments, $R^{10}$ is methyl. In some embodiments, the compound is selected from the group consisting of compounds 403-511 of Table 4 below.

For some embodiments of the foregoing compounds, the amino acid, dipeptide, tripeptide or polypeptide may comprise one or more of the naturally occurring (L-) amino acids: alanine, arginine, asparagine, aspartic acid, cysteine, glycine, glutamic acid, glutamine, histidine, isoleucine, leucine, lysine, methionine, proline, phenylalanine, serine, tryptophan, threonine, tyrosine, and valine.

Without wishing to be bound by theory, prodrugs of cathinones, such as methylone, or of phenethylamines, such as MDMA, are believed to act as a systemic controlled release system of the parent molecule active principal through in vivo bioactivation. Such bioactivation can be accomplished by either the enzymatic or chemical cleavage of the covalently bound promoiety or by a combination of both enzymatic and chemical cleavage of the covalently bound promoiety.

As used herein, "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "haloalkyl" refers to an alkyl group having 1-9 halo groups attached. Examples include —CH$_2$F, —CHF$_2$, —CF$_3$, —CH$_2$CH$_2$F, —CHFCH$_2$F, —CF$_2$CH$_2$F, —CF$_2$CHF$_2$ and —CF$_2$CF$_3$.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalenyl, adamantanyl, indanyl, indenyl, fluorenyl, 1,2,3,4-tetrahydronaphthalenyl and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "cycloalkyloxy" unless specifically stated otherwise includes a cycloalkyl group connected to the oxy connecting atom.

The term "alkoxy" unless specifically stated otherwise includes an alkyl group connected to the oxy connecting atom.

The term "aryl" unless specifically stated otherwise includes multiple ring systems as well as single ring systems such as, for example, phenyl or naphthyl.

The term "aryloxy" unless specifically stated otherwise includes multiple ring systems as well as single ring systems such as, for example, phenyl or naphthyl, connected through the oxy connecting atom to the connecting site.

The term "$C_0$-$C_6$alkyl" includes alkyls containing 6, 5, 4, 3, 2, 1, or no carbon atoms. An alkyl with no carbon atoms is a hydrogen atom substituent when the alkyl is a terminus moiety. An alkyl with no carbon atoms is a direct bond when the alkyl is a bridging moiety.

The term "hetero" unless specifically stated otherwise includes one or more O, S, or N atoms. For example, heterocycloalkyl and heteroaryl include ring systems that contain one or more O, S, or N atoms in the ring, including mixtures of such atoms. The heteroatoms replace ring carbon atoms. Thus, for example, a heterocyclo$C_5$alkyl is a five membered ring containing from 5 to no carbon atoms. Examples of heteroaryl include, pyridinyl, quinolinyl, isoquinolinyl, pyridazinyl, pyrimidinyl, pyrazinyl, quinoxalinyl, furyl, benzofuryl, dibenzofuryl, thienyl, benzothienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl.

The term "heteroaryloxy" unless specifically stated otherwise describes a heteroaryl group connected through an oxy connecting atom to the connecting site. Examples of heteroaryl($C_{1-6}$)alkyl include, for example, furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl. Examples of heterocyclo$C_{3-7}$alkyl include, for example, azetidinyl, pyrrolidinyl, piperidinyl, perhydroazepinyl, piperazinyl, morpholinyl, tetrahydrofuranyl, imidazolinyl, pyrolidin-2-one, piperidin-2-one, and thiomorpholinyl.

The term "N-heterocyclo$C_{4-7}$alkyl" describes nonaryl heterocyclic compounds having 3-6 carbon atoms and one nitrogen atom forming the ring. Examples include azetidinyl, pyrrolidinyl, piperidinyl, and perhydroazepinyl. Examples of aryl($C_{1-6}$)alkyl include, for example, phenyl($C_{1-6}$)alkyl, and naphthyl($C_{1-6}$)alkyl. Examples of heterocycloC$_{3-6}$alkylcarbonyl(C$_{1-6}$)alkyl include, for example, azetidinyl carbonyl(C$_{1-6}$)alkyl, pyrrolidinyl carbonyl(C$_{1-6}$) alkyl, piperidinyl carbonyl(C$_{1-6}$)alkyl, piperazinyl carbonyl (C$_{1-6}$)alkyl, morpholinyl carbonyl(C$_{1-6}$)alkyl, and thiomorpholinyl carbonyl(C$_{1-6}$)alkyl.

The term "amine" unless specifically stated otherwise includes primary, secondary and tertiary amines.

Unless otherwise stated, the term "carbamoyl" includes —NHC(O)OC$_1$-C$_4$alkyl, and —OC(O)NHC$_1$-C$_4$alkyl.

The term "halogen" includes fluorine, chlorine, bromine and iodine atoms.

The term "optionally substituted" is intended to include both substituted and unsubstituted. Thus, for example, optionally substituted aryl could represent a pentafluorophenyl or a phenyl ring. Further, the substitution can be made at any of the groups. For example, substituted aryl(C$_{1-6}$) alkyl includes substitution on the aryl group as well as substitution on the alkyl group.

The term "oxide" of heteroaryl groups is used in the ordinary well-known chemical sense and include, for example, N-oxides of nitrogen heteroatoms.

Compounds described herein contain one or more double bonds and may thus give rise to cis/trans isomers as well as other conformational isomers. The present invention includes all such possible isomers as well as mixtures of such isomers.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula (I) is shown without a definitive stereochemistry at certain positions. The present invention includes all stereoisomers of Formula (I) and pharmaceutically acceptable salts thereof. Further, mixtures of stereoisomers as well as isolated specific stereoisomers are also included.

During the course of the synthetic procedures used to prepare such compounds, or in using racemization or epimerization procedures known to those skilled in the art, the products of such procedures can be mixtures of stereoisomers.

In another aspect, provided herein are pharmaceutical compositions comprising a compound described herein or a pharmaceutically acceptable salt thereof; and a pharmaceutically acceptable carrier. In some embodiments, the pharmaceutical composition comprises a salt of a compound described herein.

The term "pharmaceutically acceptable salts" refers to salts prepared from pharmaceutically acceptable non-toxic bases or acids or co-crystal formers. The crystalline form can exist as salt, solvate, hydrate, or clathrate. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases or co-crystals from which salts or co-crystals can be formed include ion exchange resins such as, for example, arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the likes.

When the compound of the present invention is basic, its corresponding salt or co-crystals can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are benzenesulfonic, citric, hydrobromic, hydrochloric, maleic, phosphoric, sulfuric, and tartaric acids.

According to some embodiments, pharmaceutical compositions comprising a compound represented by Formula (I) (or pharmaceutically acceptable salts or co-crystals thereof) as an active ingredient, and a pharmaceutically acceptable carrier and optionally other therapeutic ingredients or adjuvants may be prepared.

According to another embodiment, the pharmaceutical compositions of this invention may include a pharmaceutically acceptable carrier/excipients, a compound or a pharmaceutically acceptable salt/co-crystal of Formula (I) and the corresponding parent psychoactive agent of the compound of Formula (I).

Dosage levels from about 0.0001 mg/kg to about 100 mg/kg of body weight per day may be useful in the treatment of conditions such as: post-traumatic stress disorder (PTSD), anxiety disorder, attention deficit hyperactivity disorder (ADHD), obsessive compulsive disorder (OCD), fibromyalgia, depression, cluster headache, a condition associated with cancer, diminished drive, burn-out, bore-out, migraine, Parkinson's disease, pulmonary hypertension, schizophrenia, an eating disorder, nausea, or vomiting.

The amount of active ingredient that may be combined with the carrier materials to produce a single dosage form will vary depending upon the treated target and the particular mode of administration. For example, a formulation intended for the oral administration to humans may conveniently contain from about 0.5 mg to about 5 g of active agent, formulated with an appropriate and acceptable amount of "GRAS" materials which may vary from about 5 to about 95 percent of the total composition. Unit dosage forms will generally contain between about 0.001 mg to about 5000 mg of the active ingredient, typically 0.001 mg, 0.005 mg, 0.025 mg, 0.1 mg, 0.5 mg, 2.5 mg, 5.0 mg, 10 mg, 30 mg, 60 mg, 100 mg, 300 mg, 600 mg, 1000 mg, 3000 mg, 5000 mg or any dose in-between.

Pharmaceutical compositions suitable for use as described herein include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. It is understood, however, that the specific dose level for any particular patient will depend upon a variety of factors including the age, body weight, general health, sex, diet, time of administration, route of administration, rate of excretion, drug combination and the severity of the particular disease undergoing therapy.

The composition, shape and type of dosage forms provided herein will typically vary depending on their use. For example, a dosage form used in the acute treatment of a disease may contain large amounts of one or more of the active ingredients including Formula (I) it comprises than a dosage form used in the chronic treatment of the same disease. Similarly, a parenteral dosage form may contain smaller amounts of one or more of the active ingredients including Formula (I) it comprises than an oral dosage form used to treat the same disease. These and other ways in which specific dosage forms provided herein will vary from one another will be readily apparent to those skilled in the art. See, e.g., *Remington's Pharmaceutical Sciences, 20<sup>th</sup>* ed., Mack Publishing, Easton, Pa (2000). In practice, the compounds represented by Formula (I), or pharmaceutically acceptable salts/co-crystals thereof, of this invention can be combined as the active ingredient in intimate admixture with a pharmaceutical excipients, carrier, or diluents according to conventional pharmaceutical compounding techniques. The carrier may take a wide variety of forms depending on the form of preparation desired for administration, e.g., oral, mucosal (e.g., nasal, sublingual, vaginal, inhalational, cystic, rectal, ocular, buccal or aural), parenteral (including intravenous, intradermal, subcutaneous, bolus injection, intramuscular or intraarterial) or topical (e.g., transdermal, transcutaneous, eye drops or other ophthalmic preparations). Thus, the pharmaceutical compositions of the present invention can be presented as discrete units suitable for oral administration such as capsules (coated or non-coated with polymers as sustained release or enteric coated or modified for target delivery), sachets or tablets (coated or uncoated or bilayers or sustained release or delayed release including micro-encapsulation) or tablets containing spray dried intermediates each containing a predetermined amount of the active ingredient. Further, the compositions can be presented as a powder, as granules, as coated sustained release particles, as a solution, as a suspension in an aqueous liquid, as a non-aqueous liquid, as an oil-in-water emulsion or as a water-in-oil liquid emulsion, liposomes, nanosuspension. In addition to the common dosage forms set out above, the compound represented by Formula (I), or pharmaceutically acceptable salts or co-crystals thereof, may also be administered by controlled or modified release formulation and/or delivery devices. The compositions may be prepared by any of the methods of pharmacy. In general, such methods include a step of bringing into association the active ingredient with the excipients or carriers that constitutes one or more necessary ingredients. In general, the compositions are prepared by uniformly and intimately admixing the active ingredient with liquid carriers/excipients or finely divided solid carriers/excipients or both. The product can then be conveniently shaped into the desired presentation.

Thus, the pharmaceutical compositions of this invention may include a pharmaceutically acceptable carrier/excipients and a compound or a pharmaceutically acceptable salt/co-crystal of Formula (I). The compounds of Formula (I), or pharmaceutically acceptable salts/co-crystals thereof, can also be included in pharmaceutical compositions in combination with one or more other therapeutically active compounds.

The pharmaceutical carrier employed can be, for example, to form oral solid preparations such as powders, capsules and tablets include fillers such as talc, calcium carbonate, microcrystalline cellulose, kaolin, mannitol, silicic acid, sorbitol, starch, and mixture thereof. Binder such as Kollidon. Disintegrants such as croscarmellose sodium, crospovidone, sodium starch glycolate, pre-gelatinized starch, gums and other starches and mixtures thereof. Lubricants such as calcium stearate, magnesium stearate, syloid silica gel, mineral oil, glycerine, sorbitol, mannitol, polyethylene glycol, stearic acid, sodium lauryl sulphate, talc, hydrogenated vegetable oil (e.g., peanut oil, sesame oil, corn oil or soybean oil), ethyl oleate agar or other lipid formulation lubricants and mixtures thereof. Because of their ease of administration, tablets and capsules are the preferred oral dosage units whereby solid pharmaceutical carriers are employed. Each of the solid oral dosage units can be further coated with specialized polymers that can delay release or sustained release the contents of the dosage units. Formula (I) can be administered by delayed release or sustained release means or by delivery devices that are well known to those of ordinary skill in the art. Non-limiting examples of delayed release or sustained release include those described in U.S. Pat. Nos. 3,845,770; 3,916,899; 3,536,809; 5,059, 595. Such dosage forms can be used to provide slow or controlled release of one or more ingredients using for example polymers such as hydroxylpropylmethyl cellulose usually in a matrix form such as gel, permeable membranes, micro-emulsions, osmotic systems, liposomes, microspheres or combinations thereof. Controlled release formulation can be used to protect the dosage units from exposure to the gastric environment; delay release of active ingredient to the lower gastrointestinal tract such as the colon; or slow the release of the active ingredient such that blood levels of the drug can be lowered and affect the occurrence of side effects.

Examples of gaseous carriers include carbon dioxide and nitrogen.

In preparing the oral liquid compositions for oral dosage form, any convenient pharmaceutical media may be employed. For example, water, glycols, oils, alcohols, flavoring agents, preservatives, coloring agents and the like may be used to form oral liquid preparations such as suspensions, elixirs, and solutions.

A tablet containing the composition of this invention may be prepared by compression or molding, optionally with one or more accessory ingredients or adjuvants.

Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.001 mg to about 5000 mg of the active ingredient and each cachet or capsule preferably containing from about 0.001 mg to about 5000 mg of the active ingredient.

Pharmaceutical compositions of the present invention suitable for parenteral administration (including intravenous, intramuscular, subcutaneous, ocular, and intraarterial) may be prepared as solutions or suspensions of the active compounds in injectable ingredients. Parenteral dosage forms are preferably sterile or capable of being sterilized prior to administration to a patient. Non-limiting examples of suitable vehicles include Water for Injection USP; Dextrose Injection; Sodium Chloride Injection and lactated Ringer's Injection. A suitable surfactant can be included such as, for example, polysorbate 80. Dispersions can also be prepared in glycerol, liquid polyethylene glycols, ethyl alcohol, polypropylene glycol and mixtures thereof in non-aqueous vehicles such as oils (e.g., corn oil, sesame oil, isopropyl myristate). An antioxidant to help stabilize the formulation such as Vit C palmitate. Further, a preservative can be included to prevent the detrimental growth of microorganisms.

Furthermore, the compositions can be in the form of sterile powders for the extemporaneous preparation of such sterile injectable solutions or dispersions. In all cases, the final injectable form must be sterile, non-irritating with addition of tonicity agents and must be effectively fluid for easy syringeability. The pharmaceutical compositions must be stable under the conditions of manufacture and storage; thus, preferably should be preserved against the contaminating action of microorganisms such as bacteria and fungi such as benzalkonium chloride, chlorobutanol, methyl paraben, propyl paraben, edetate disodium, sorbic acid or other agents known to those skilled in the art. Pharmaceutical compositions of the present invention can be in a form suitable for topical applied locally to the skin and its adnexa or to a variety of mucous membranes such as, for example, an aerosol, patch, cream, ointment, lotion, dusting powder, emulsions or the like. The routes that can be used include nasal, sublingual, vaginal, rectal, ocular, buccal or aural. Further, the compositions can be in a form suitable for use in transdermal or intradermal micro-needle devices. These formulations may be prepared, utilizing a compound represented by Formula (I) of this invention, or pharmaceutically acceptable salts thereof, via conventional processing methods. As an example, a lotion, cream or ointment is prepared by mixing hydrophilic material and water, together with about 5 wt % to about 30 wt % of the compound, to produce a cream, lotion or ointment having a desired consistency. Examples of typical excipients include water, acetone, ethanol, ethylene glycol, propylene glycol, isopropyl myristate, mineral oil and mixtures thereof. Moisturizers such as occlusive, humectant, emollients can also be added to the pharmaceutical compositions and dosage forms if desired. pH of a pharmaceutical composition or dosage form may also be adjusted to improve delivery of Formula (I). Dosage forms suitable for treating mucosal tissues within the oral cavity can be formulated as mouthwashes or as oral gel.

Pharmaceutical compositions of this invention can be in a form suitable for rectal administration wherein the carrier is a solid or liquid or spray. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, binders, surface-active agents, thickeners, lubricants, preservatives (including antioxidants) and the like. Furthermore, other adjuvants can be included to render the formulation isotonic with the blood of the intended recipient. Compositions containing a compound described by Formula (I), or pharmaceutically acceptable salts thereof, may also be prepared in powder or liquid concentrate form. Addition of preservatives such as antioxidants are widely acceptable in pharmaceutical arts as a means of simulating long-term storage in order to determine characteristics such as shelf life or stability of formulations over time (See e.g., Jens T. Carstensen, *Drug stability: Principles & Practice.* $2^{nd}$ Ed., Marcel Dekker, NY, NY. 1995, pp 379-80).

All diseases, conditions, and disorders listed herein defined as described in the Diagnostic and Statistical Manual of Mental Disorders (DSM-5), published by the American Psychiatric Association, or in International Classification of Diseases (ICD), published by the World Health Organization.

As used herein, the terms "reduce," "decrease," "lessen" and similar terms mean a decrease of at least about 10%, about 15%, about 20%, about 25%, about 35%, about 50%, about 75%, about 80%, about 85%, about 90%, about 95%, about 97%, or more.

As used herein, the terms "improve," "increase," "enhance," and similar terms indicate an increase of at least about 10%, about 15%, about 20%, about 25%, about 50%, about 75%, about 100%, about 150%, about 200%, about 300%, about 400%, about 500%, or more.

In one embodiment, a variety of other therapeutic agents may find use for administration with the compositions and methods provided herein.

In another aspect, provided herein are methods of treating and/or preventing a disease or condition, such as a neuropsychiatric illness, and/or ameliorating a symptom thereof in a subject in need thereof comprises administering to the subject an effective amount of a compound provided herein. In some embodiments, the disease or condition is selected from post-traumatic stress disorder (PTSD), anxiety disorder, attention deficit hyperactivity disorder (ADHD), obsessive compulsive disorder (OCD), fibromyalgia, depression, cluster headache, a condition associated with cancer, diminished drive, burn-out, bore-out, migraine, Parkinson's disease, pulmonary hypertension, schizophrenia, an eating disorder, nausea, or vomiting. In some embodiments, the disease or condition is PTSD. In some embodiments, the disease or condition is an anxiety disorder. In some embodiments, the disease or condition is depression.

The compounds provided herein may be used for various therapeutic purposes. In one embodiment, the compounds are administered to a subject to treat a neuropsychiatric illness. A "subject" for the purposes of the compositions and methods provided herein includes humans and other animals, preferably mammals and most preferably humans. Thus, the compounds provided herein have both human therapy and veterinary applications. In another embodiment the subject is a mammal, and in yet another embodiment the subject is human. By "condition", "disease", or "illness" herein are meant a disorder that may be ameliorated by the administration of compounds provided herein and pharmaceutical compositions thereof.

Methods and compositions described herein can be used for prophylaxis, as well as amelioration of signs and/or symptoms of a condition, such as a neuropsychiatric illness. The terms "treating" and "treatment" used to refer to treatment of a condition in a subject include: preventing, inhibiting or ameliorating the condition in the subject, as well as reducing or ameliorating a sign or symptom of the condition. Treatment goals may incorporate endpoints such as improvement in DSM-5 severity scales, to measure if resilience and quality of life are enhanced, with engagement of positive cognitive valence systems, and corresponding reduction in negative valence.

It is to be understood by one of skill in the art that the methods of treatment and/or prevention comprising administering a compound provided herein for the treatment and/or prevention of one or more indications as described herein also include: the use of a compound provided herein in the manufacture of a medicament for the treatment and/or prevention of one or more indications as described herein;

and the use of a compound provided herein for the treatment and/or prevention of one or more indications as described herein.

Pharmaceutical compositions are contemplated for the compounds and methods provided herein. Formulations of the compositions and methods provided herein are prepared for storage by mixing said compound having the desired degree of purity with optional pharmaceutically acceptable carriers, excipients, or stabilizers, in the form of lyophilized formulations or aqueous solutions. Acceptable carriers, excipients, or stabilizers are nontoxic to recipients at the dosages and concentrations employed, and include buffers such as phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches; binding agents; additives; coloring agents; salt-forming counter-ions such as sodium; metal complexes (e.g., Zn-protein complexes); and/or non-ionic surfactants or polyethylene glycol (PEG). In another embodiment, the pharmaceutical compositions provided herein are in a water-soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The formulations to be used for in vivo administration are preferably sterile. This is readily accomplished by filtration through sterile filtration membranes or other methods.

Pharmaceutically acceptable excipients for formulations of compounds provided herein include, but are not limited to: diluents, e.g., microcrystalline cellulose, starch, mannitol, calcium hydrogen phosphate anhydrous or co-mixtures of silicon dioxide, calcium carbonate, microcrystalline cellulose and talc; disintegrants, e.g., sodium starch glycolate or croscarmellose sodium; binders, e.g., povidone, co-povidone or hydroxyl propyl cellulose; lubricants, e.g., magnesium stearate or sodium stearyl fumurate; glidants, e.g., colloidal silicon dioxide; and film coats, e.g., Opadry II white or PVA based brown Opadry II.

The compounds provided herein may also be entrapped in microcapsules prepared by methods including, but not limited to, coacervation techniques, interfacial polymerization (e.g., using hydroxymethylcellulose or gelatin-microcapsules, or poly-(methylmethacylate) microcapsules), colloidal drug delivery systems (e.g., liposomes, albumin microspheres, microemulsions, nano-particles and nanocapsules), and macroemulsions. Sustained-release preparations may be prepared. Suitable examples of sustained-release preparations include semipermeable matrices of solid hydrophobic polymer, which matrices are in the form of shaped articles, e.g., films, or microcapsules. Examples of sustained-release matrices include polyesters, hydrogels (for example poly(2-hydroxyethyl-methacrylate), or poly(vinylalcohol)), polylactides, copolymers of L-glutamic acid and gamma ethyl-L-glutamate, non-degradable ethylene-vinyl acetate, degradable lactic acid-glycolic acid copolymers (which are injectable microspheres composed of lactic acid-glycolic acid copolymer and leuprolide acetate), and poly-D-(−)-3-hydroxybutyric acid) which is a microsphere-based delivery system composed of the desired bioactive molecule incorporated into a matrix of poly-DL-lactide-co-glycolide (PLG).

Administration of the pharmaceutical composition comprising the compounds provided herein, for example in the form of a sterile aqueous solution, may be done in a variety of ways, including, but not limited to orally, subcutaneously, intravenously, intranasally, intraotically, transdermally, topically (e.g., gels, salves, lotions, creams, etc.), intraperitoneally, intramuscularly, intrapulmonary, vaginally, parenterally, rectally, or intraocularly. As is known in the art, the pharmaceutical composition may be formulated accordingly depending upon the manner of introduction.

In some embodiments, the pharmaceutical formulation is an oral dosage form. In some embodiments, the pharmaceutical formulation is a parenteral dosage form. In some embodiments, the pharmaceutical composition comprises a tablet. In some embodiments, the pharmaceutical composition comprises a capsule. In some embodiments, the pharmaceutical composition comprises a dry powder. In some embodiments, the pharmaceutical composition comprises a solution. In some embodiments, more than one dosage form is administered to the subject at substantially the same time. In some embodiments, the subject may be administered the entire therapeutic dose in one tablet or capsule. In some embodiments, the therapeutic dose may be split among multiple tablets or capsules.

As used herein, the singular forms "a," "an," and "the" include plural references unless the context clearly dictates otherwise. For example, the term "a molecule" can also include a plurality of molecules.

The terms "about" or "approximately", which are used interchangeably herein, means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Furthermore, the term "about" as used herein when referring to a measurable value such as a dose, time, temperature, and the like, is meant to encompass variations of ±20%, ±10%, ±5%, ±1%, ±0.5%, or even ±0.1% of the specified amount.

Reference to a particular numerical value includes at least that particular value, unless the context clearly dictates otherwise. When a range of values is expressed, another embodiment includes from the one particular value and/or to the other particular value. Further, reference to values stated in ranges include each and every value within that range. All ranges are inclusive and combinable.

The phrase "and/or," as used herein, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements can optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements can optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Unless the context indicates otherwise, it is specifically intended that the various features described herein can be used in any combination.

Any patent, patent application publication, or scientific publication, cited herein, is incorporated by reference herein in its entirety.

The following examples are presented in order to more fully illustrate the preferred embodiments of the invention. They should in no way be construed, however, as limiting the broad scope of the invention.

Example 1

Methods of Synthesis

The compounds of Formula (I) of the present invention can be prepared according to the proposed synthetic routes outlined in Schemes 1-17 below starting from the parent molecule II. Methylone IIa (Y=CO, $R^1$=$CH_3$, $R^2$=$CH_3$), ethylone IIb (Y=CO, $R^1$=$CH_3$, $R^2$=$CH_2CH_3$), butylone IIc (Y=CO, $R^1$=$CH_2CH_3$, $R^2$=$CH_3$) and MDMA IId (Y=$CH_2$, $R^1$=$CH_3$, $R^2$=$CH_3$) can be prepared using procedures such as the one described in WO9639133A1 (IIa); Heather E. et al. *Drug Test. Analysis*, 2017, 9, 426 (IIa); Maheux C. R. et al. *Drug Test. Analysis*, 2016, 8, 847 (IIb); Maheux C. R. et al. *Drug Test. Analysis*, 2012, 4, 17 (IIc) and Milhazes N. et al. *Anal. Chem. Act.* 2007, 596, 231 (IId).

The amino acid derived prodrugs of Formula Ib and Id may be prepared by coupling the requisite amine II with appropriate amino acids as presented in Scheme 1 below where $R^{11}$ and $R^{12}$ are each independently selected from the side chain residue of the naturally occurring amino acid. To conjugate an amino acid with II, the one amino group is preferably protected with a protecting group (Pg) before the amino acid is reacted with II. Agents and methods for protecting amino groups in a reactant are known in the art. Examples of protecting groups that may be used to protect the amino groups include, but are not limited to, fluorenylmethoxycarbonyl (Fmoc), t-butylcarbonate (Boc), trifluoroacetate (TFA), acetate (Ac) and benzyloxycarbonyl (CBZ). Preferably, the carboxylic acid group in the N-protected amino acid is activated by an acid activating agent (sometimes also called coupling reagent) to help the reaction of the N-protected amino acid with II. Examples of acid activating agents (coupling reagents) well known in the art include, but are not limited to, dicyclohexylcarbodiimide (DCC), 1-ethyl-3-(3'-dimethylaminopropyl)-carbodiimide (EDC), 1,1-carbonyldiimidazole (CDI), diisopropylcarbodiimide (DIC), hexafluorophosphate benzotriazole tetramethyl uronium (HBTU) and hexafluorophosphate azabenzotriazole tetramethyl uranium (HATU). The use of appropriate acyl halide or anhydride as an activated acylating group in the N-protected amino acid is also contemplated. After coupling with any standard coupling procedure to afford the intermediate protected prodrug Ia, deprotection can occur with standard reagent known in the art to afford the desired prodrugs Ib. This amino acid prodrug can be further derivatized to a dipeptide by repeating the coupling procedure to afford the prodrug Id, after deprotection of the newly added amino group of Ic.

Scheme 1

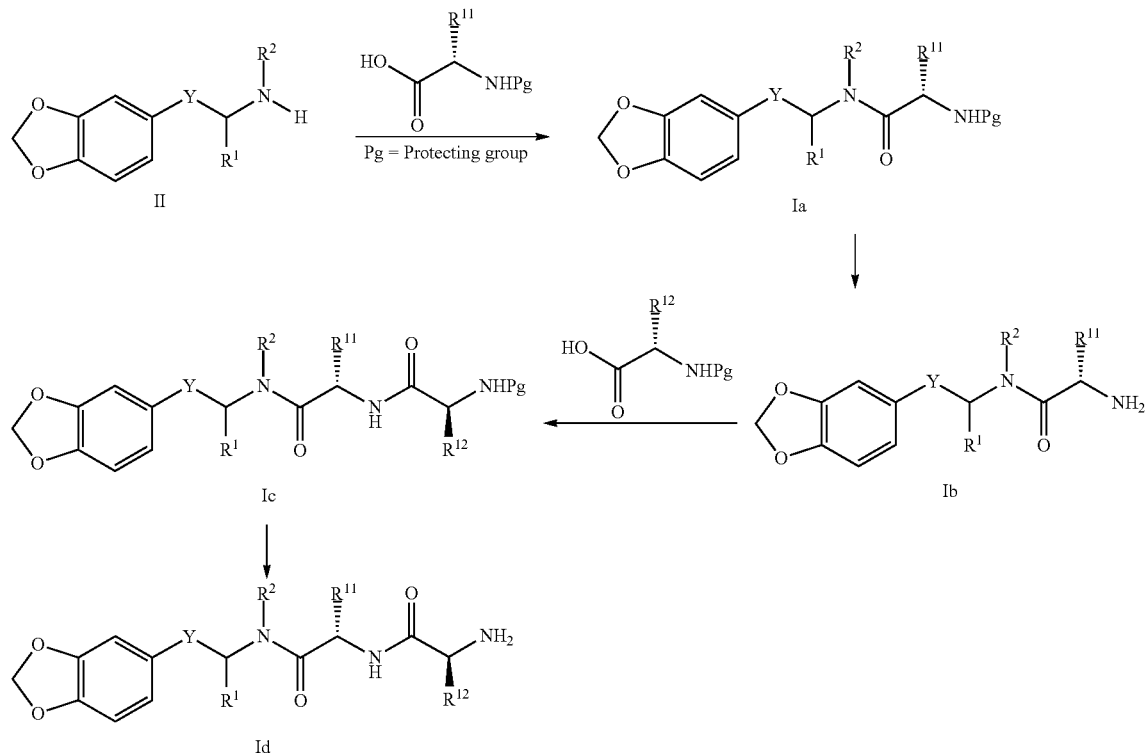

Alternatively, the peptide derived prodrug of Formula Id may be prepared by coupling the requisite amine II and an appropriate dipeptide as presented in Scheme 2 below. Such a conjugation may be accomplished under the conditions previously described for the intermediate Ia (Scheme 1). The requisite dipeptide is provided by the coupling of two amino acids, each independently selected from the naturally occurring L amino acids using standard peptide coupling protocols known in the art.

The amide prodrug of Formula Ie may be prepared by coupling the requisite amine II with an appropriate acylating agent as presented in Scheme 3 below. Acylation of the amino group of II may be accomplished by reaction with an acid chloride (Z=Cl) or anhydride (Z=—OC(O)R$^3$ or —OC(O)t-Butyl) in the presence of a base such as diisopropylethylamine (DIPEA), triethylamine, 4-methylmorpholine, NaHCO$_3$, K$_2$CO$_3$ or 2,6-lutidine in an appropriate solvent such as methylene chloride, THF, DMF, acetonitrile, or toluene. The coupling reaction may also be performed Scheme 2

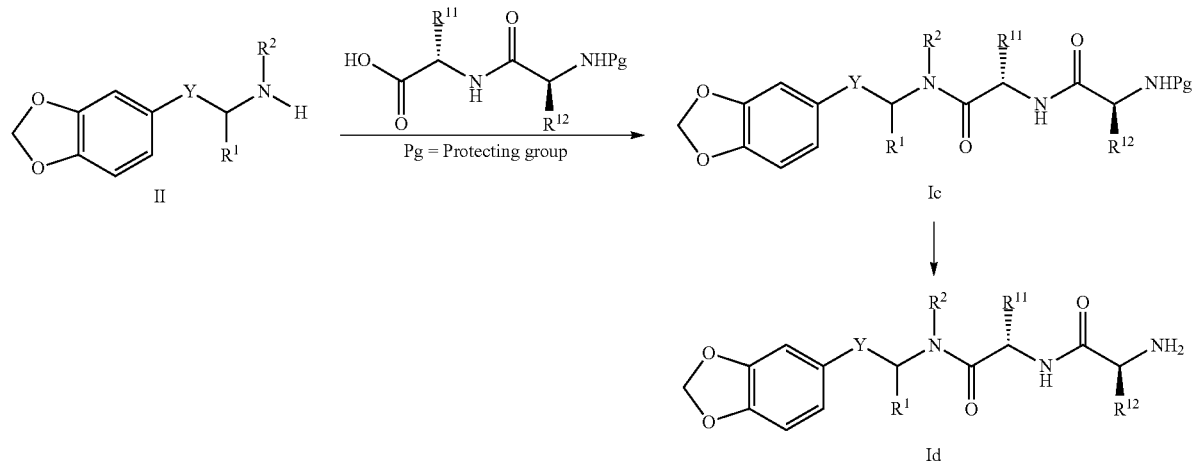

with a carboxylic acid (Z=OH) in the presence of a coupling reagent, such as N,N-dicyclohexylcarbodiimide (DCC), N-ethyl-N'-(3-dimethylaminopropyl)-carbodiimide (EDC), 1,1-carbonyldiimidazole (CDI), diisopropylcarbodiimide (DIC), hexafluorophosphate benzotriazole tetramethyl uronium (HBTU) and hexafluorophosphate azabenzotriazole tetramethyl uranium (HATU) or other similar reagents well known to one skilled in the art.

Scheme 3

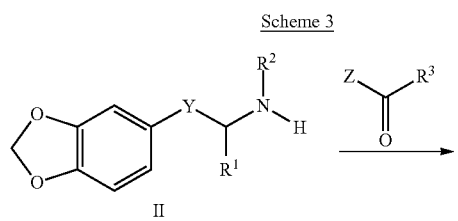

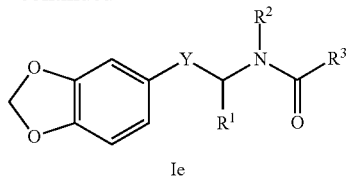

Ie

The carbamate prodrug of Formula If may be prepared by coupling the requisite amine II with an appropriate chloroformate as presented in Scheme 4 below. The coupling reaction is performed in the presence of a base such as diisopropylethylamine (DIPEA), triethylamine, NaOH, NaHCO$_3$, K$_2$CO$_3$ or pyridine in an appropriate solvent such as methylene chloride, THF, ethyl acetate, acetonitrile, 1,4-dioxanne or water. Alternatively, the carbamate If can be prepared by the sequential addition of triphosgene to the amine II in presence of a base such as diisopropylethylamine (DIPEA) in a solvent such as methylene chloride, followed by the addition of an alkoxide such as NaOR$^3$.

Scheme 4

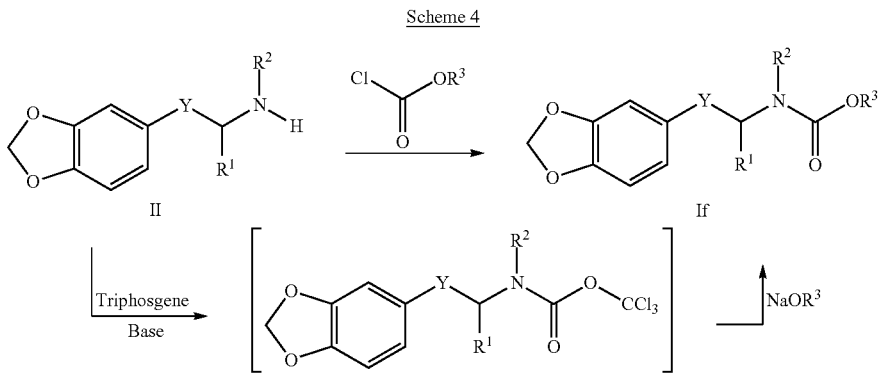

The acyloxyalkoxycarbonyl prodrug of Formula Ig (Scheme 5) may be prepared by sequentially coupling the requisite amine II with 1-chloroethyl chloroformate in the presence of a base, such as triethylamine or diisopropylethylamine in a solvent, such as methylene chloride, followed by the addition of a selected carboxylate. Such a carboxylate may be generated by reacting the corresponding carboxylic acid R$^3$CO$_2$H with a base such as triethylamine or cesium carbonate in a solvent such as DMF or acetonitrile. Alternatively, the acyloxyalkoxycarbonyl prodrug of Formula Ig could be directly accessed by coupling the requisite amine II with an electrophilic acylating agent such as 1-(((4-nitrophenoxy)carbonyl)oxy)ethyl carboxylate in the presence of a base, such as triethylamine or diisopropylethylamine in a solvent, such as methylene chloride.

Scheme 5

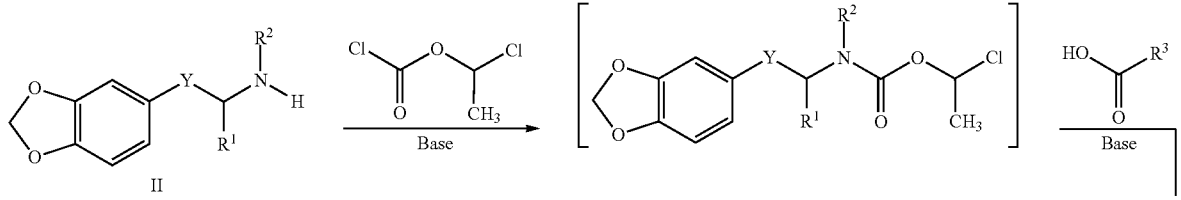

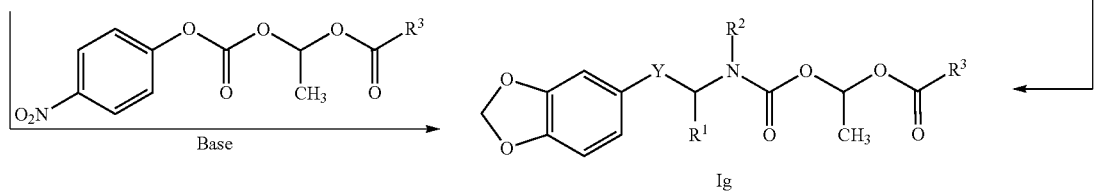

Ig

The acyloxymethyl prodrug of Formula Ih may be prepared by coupling the requisite amine II with an appropriate chloromethyl ester in the presence of a basic agent such as triethylamine in a solvent such as acetonitrile (Scheme 6). The chloromethyl ester $R^3C(O)OCH_2Cl$ can be prepared according to the procedures described in US20150274670A1 and US 20070155729A1 where the acyl chloride of formula $R^3COCl$ would be reacted with paraformnaldehyde.

The phosphoryloxymethyl of Formula Ik may be prepared in a two-step sequence from the requisite amine II as presented in Scheme 8 below. Following the procedure found in WO 2020/008064, a solution of amine II in a solvent such as acetonitrile can be treated with a basic agent such $K_2CO_3$, NaI and di-tert-butyl chloromethylphosphate at a controlled temperature of 50° C. to afford the protected phosphonate Ij. Hydrolysis of this intermediate under aqueous acidic conditions would provide the phosphoryloxymethyl prodrug Ik.

Scheme 6

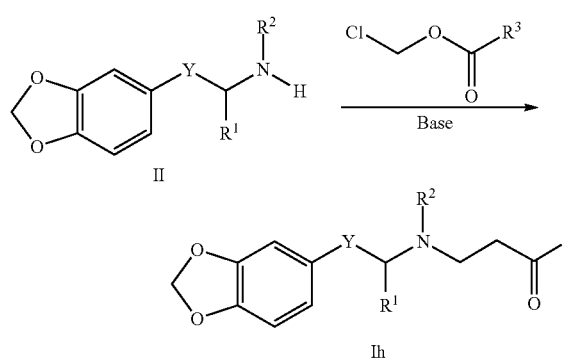

The phosphoramide prodrug of Formula Ii may be prepared according to the procedure described in WO 2020/008064. As depicted in the Scheme 7 below, $PCl_5$ is added to the requisite amine II in the presence of abasic agent such pyridine and in a solvent such as methylene chloride. A mixture of water/DMSO in then added to hydrolyse the dichlorophosphoramide solution to afford the phosphoramide prodrug of Formula Ii.

Scheme 7

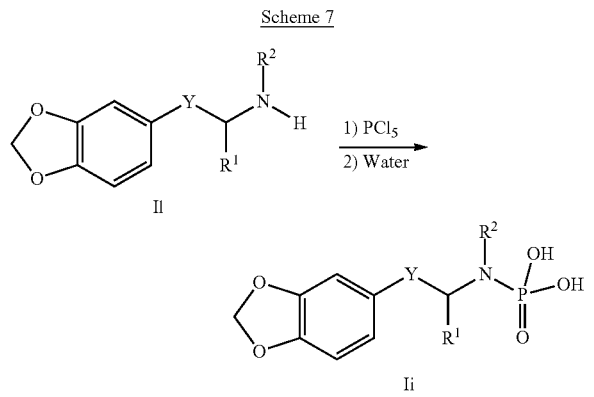

Scheme 8

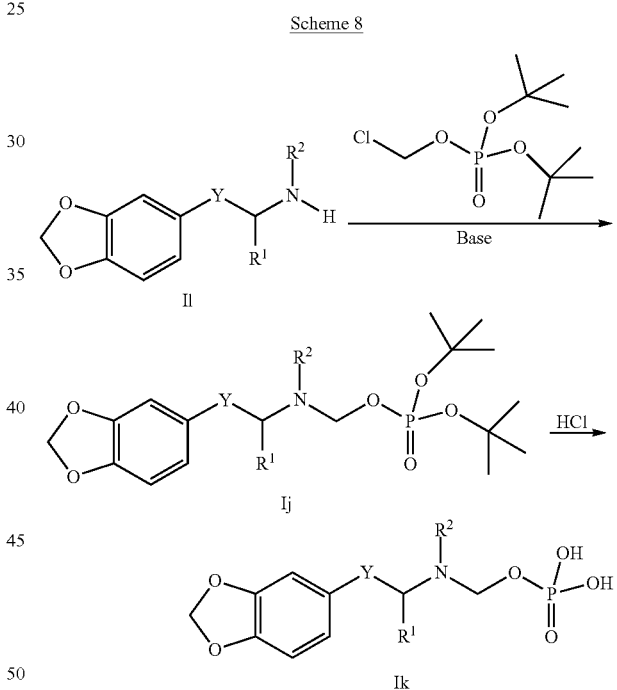

The phosphoryloxyalkoxycarbonyl prodrug of Formula Im (Scheme 9) may be prepared according to the procedure describe by Safadi M. et al. *Pharm Res,* 1993, 10(9), 1350, by sequentially coupling the requisite amine II with a chloroalkyl chloroformate in the presence of a base, such as triethylamine or diisopropylethylamine in a solvent, such as methylene chloride, followed by the addition of a suitably protected phosphate such as dibenzyl phosphate ($R^{11}$ and $R^{12}$=benzyl). Such a phosphate may be generated by reacting the corresponding phosphonic acid with a base such as silver carbonate in a solvent such as DMF or acetonitrile. When $R^{11}$ and $R^{12}$ are benzyl, the dihydrogen phosphate Im may be obtained by deprotecting the phosphate intermediate IL using a catalytic amount of Pd/C under $H_2$ atmosphere in a solvent such as ethyl acetate.

Scheme 9

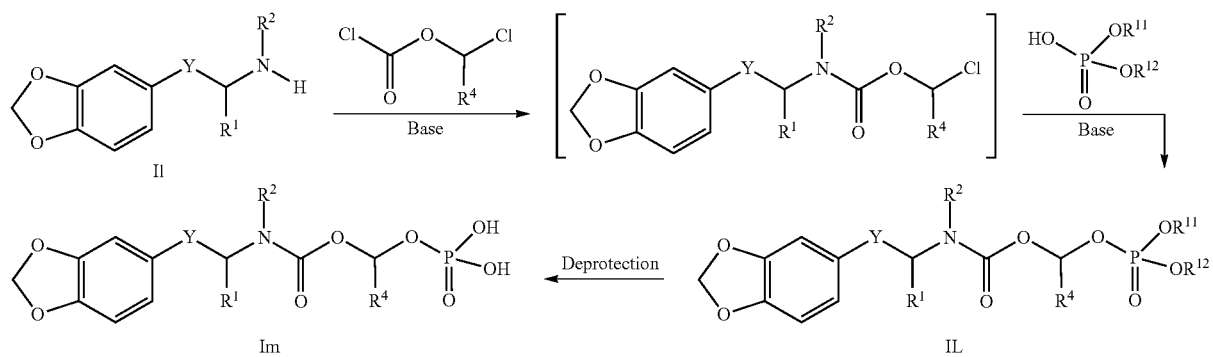

The amide prodrug of Formula Ip may be prepared by coupling the requisite amine II with the carboxylic acid Io as presented in Scheme 10 below. When $Z^a$ is O, NH or $NCH_3$, those carboxylic acids may be obtained from a commercial source where a wide diversity of $R^3$ groups such as alkyl, cycloalkyl, aryl, heteroaryl and amino acids could be found. The coupling reaction may be performed in the presence of a coupling reagent, such as N,N-dicyclohexylcarbodiimide (DCC), N-ethyl-N'-(3-dimethylaminopropyl)-carbodiimide (EDC), 1,1-carbonyldiimidazole (CDI), diisopropylcarbodiimide (DIC), hexafluorophosphate benzotriazole tetramethyl uronium (HBTU) and hexafluorophosphate azabenzotriazole tetramethyl uranium (HATU) or other similar reagents well known to one skilled in the art. In the event that the carboxylic acid would not be commercially available, Io could be prepared by acylation of the amino group ($Z^a=NR^4$) or of the hydroxy group ($Z^a=O$) of In by reaction with a carboxylic acid (Z=OH) in the presence of a coupling agent as described above. Alternatively, the amine In may also be reacted with an acid chloride (Z=Cl) or with an anhydride (Z=—OC(O)$R^3$ or —OC(O)t-Butyl) in the presence of a base such as diisopropylethylamine (DIPEA), triethylamine, 4-methylmorpholine, $NaHCO_3$, $K_2CO_3$ or 2,6-lutidine in an appropriate solvent such as methylene chloride, THF, DMF, acetonitrile, or toluene.

Scheme 10

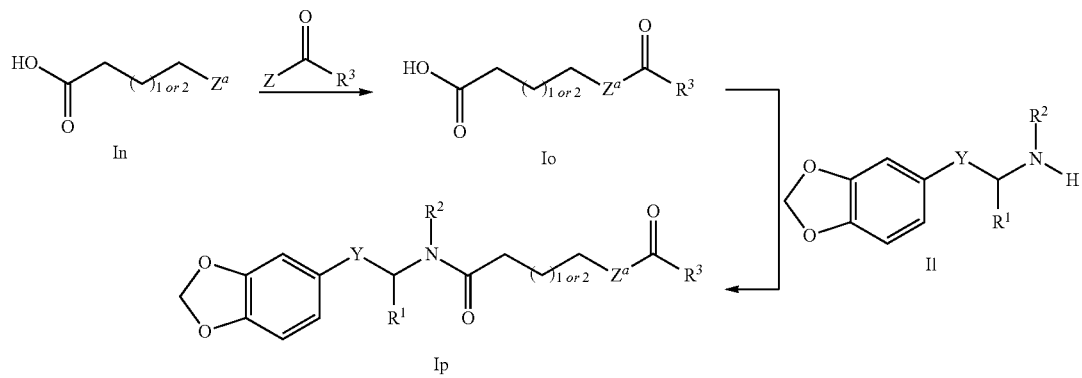

The carbamate prodrug of Formula It may be prepared by coupling the requisite amine II with a benzylic alcohol Is as presented in Scheme 11 below. When $Z^b$ is O, NH or $NCH_3$, benzylic alcohols may be obtained from a commercial source where a wide diversity of $R^3$ group such as alkyl, cycloalkyl, aryl, heteroaryl and amino acids could be found. The coupling reaction may be performed as described in US 2017/0145044 A1 by the sequential reaction of the benzylic alcohol with a reagent such as carbonyl diimidazole in a solvent such as dichloromethane, followed by the addition of the amine 1l. In the event that the benzylic alcohol would not be commercially available, Is could be prepared following a two-step sequence where the requisite commercially available phenol ($Z^b$=O) or aniline ($Z^b$=NR$^4$) Iq would be acylated in an analogous way as described above for Io preparation (Scheme 10), followed by the reduction of the benzaldehyde Ir with a reagent such as sodium borohydride in a solvent such as dichloromethane in the presence of an alcohol such as isopropanol.

obtained from a commercial source where a wide diversity of R$^3$ group such as alkyl, cycloalkyl, aryl, heteroaryl and amino acids could be found. The coupling reaction may be performed by the sequential reaction of the benzylic alcohol with a reagent such as carbonyl diimidazole in a solvent such as dichloromethane, followed by the addition of the amine II. In the event that the benzylic alcohol would not be commercially available, Iw could be prepared following a two-step sequence where the requisite commercially available phenol ($Z^b$=O) or aniline ($Z^b$=NR$^4$) Iu would be

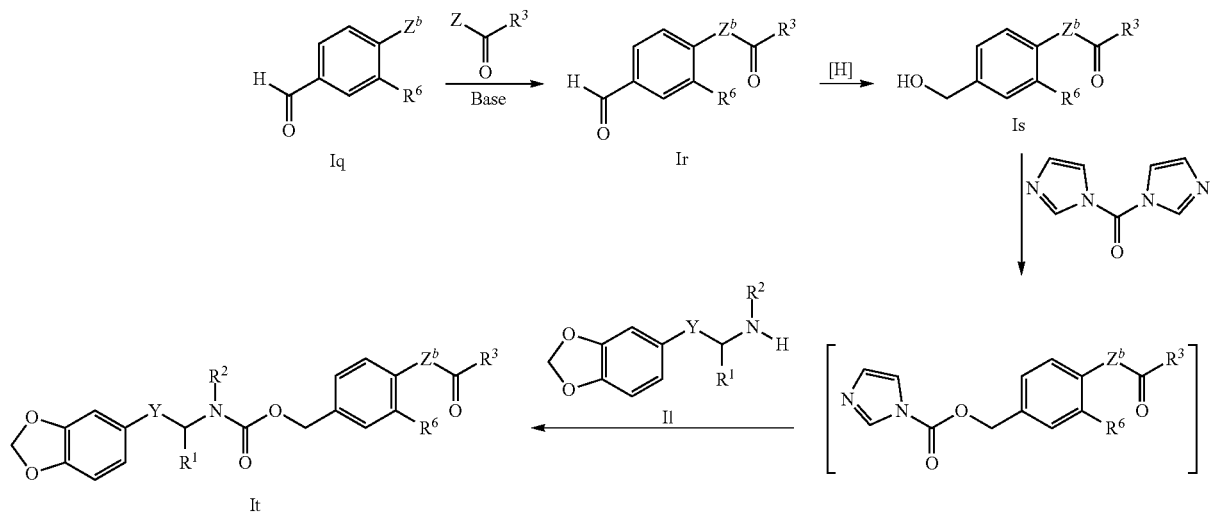

Scheme 11

The carbamate prodrug of Formula Ix may be prepared by coupling the requisite amine II with a benzylic alcohol Iw as presented in Scheme 12 below and following an analogous assemblage sequence as described above in Scheme 11. When $Z^b$ is O, NH or NCH$_3$, benzylic alcohols may be acylated in an analogous way as described above for Io preparation (Scheme 10), followed by the reduction of the benzaldehyde Iv with a reagent such as sodium borohydride in a of solvent such as dichloromethane in the presence of an alcohol such as isopropanol.

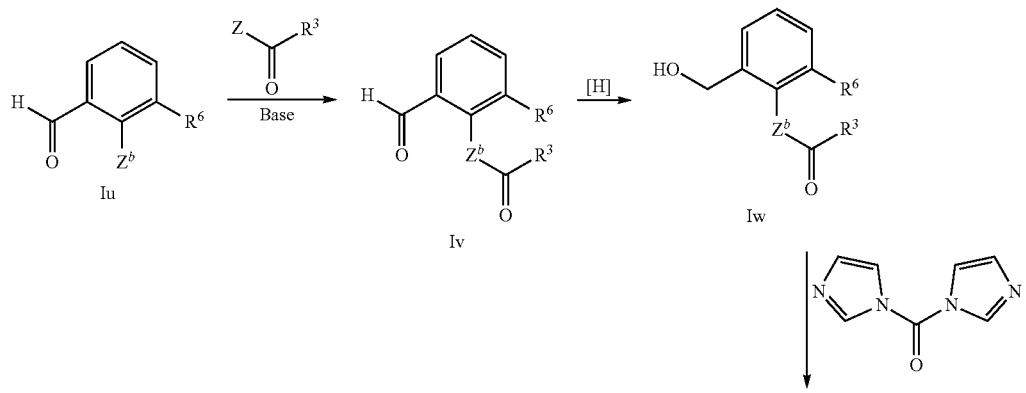

Scheme 12

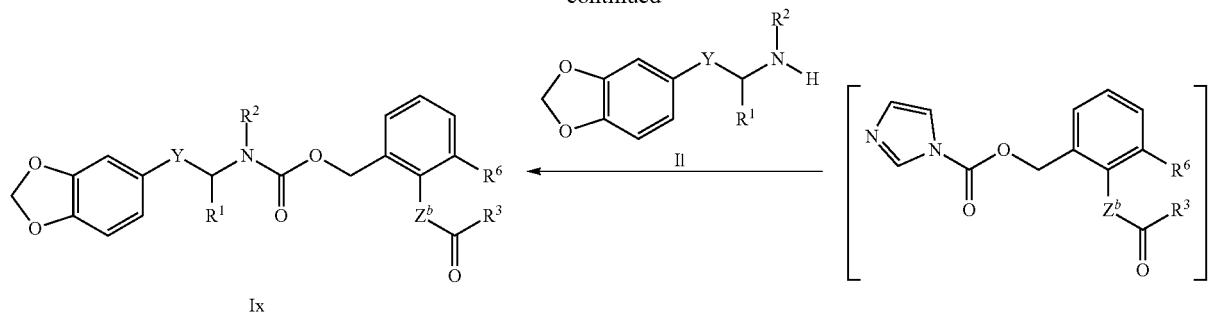

The phosphonate prodrug of Formula Iaa may be prepared by coupling the requisite amine II with a benzylic alcohol Iz as presented in Scheme 13 below and following an analogous assemblage sequence as described previously in Scheme 11. The protected phosphate Iy may be obtained by the reaction of a commercially available phenol Iq-1 with a protected phosphate reagent such as di-tert-butylchlorophosphate or di-benzylchlorophosphate in the presence of a base such as triethylamine, i-$Pr_2$NEt or DBU in a solvent such as THF or dichloromethane in the presence of a catalyst such as DMAP. Treatment of the benzaldehyde Iy with a reagent such as sodium borohydride in a of solvent such as dichloromethane in the presence of an alcohol such as isopropanol would afford the benzylic alcohol Iz. Carbamate bound formation may be performed by the reaction of the benzylic alcohol with a reagent such as carbonyl diimidazole in a solvent such as dichloromethane, followed by the addition of the amine II. Deprotection of the phosphate to afford Iaa may be performed under acidic conditions (Pg=tert-butyl) using a reagent such as TFA or $HCl_{aq}$· in solvent such as methylene chloride or THF. Unless $R^6$ is not compatible with reductive conditions, such as $R^6$=$NO_2$, CN or Br, the deprotection may also be done under hydrogenolysis conditions (Pg=benzyl) using Pd/C as a catalyst in a solvent such as methanol under an atmosphere of $H_2$.

The phosphonate prodrug of Formula Idd may be prepared by coupling the requisite amine II with a benzylic alcohol Icc as presented in Scheme 14 below and following an analogous assemblage sequence as described previously in Scheme 11. The protected phosphate Ibb may be obtained by the reaction of a commercially available phenol Iu-1 with a protected phosphate reagent such as di-tert-butylchlorophosphate or di-benzylchlorophosphate in the presence of a base such as triethylamine, i-$Pr_2$NEt or DBU in a solvent such as THF or dichloromethane in the presence of a catalyst such as DMAP. Treatment of the benzaldehyde Ibb with a reagent such as sodium borohydride in a of solvent such as dichloromethane in the presence of an alcohol such as isopropanol would afford the benzylic alcohol Icc. Carbamate bound formation may be performed by the reaction of the benzylic alcohol with a reagent such as carbonyl diimidazole in a solvent such as dichloromethane, followed by the addition of the amine II. Deprotection of the phosphate to afford Iaa may be performed under acidic conditions (Pg=tert-butyl) using a reagent such as TFA or $HCl_{aq}$· in solvent such as methylene chloride or THF. Unless $R^6$ is not compatible with reductive conditions, such as $R^6$=$NO_2$, CN or Br, the deprotection may also be done under reductive conditions (Pg=benzyl) using Pd/C as a catalyst in a solvent such as methanol under an atmosphere of $H_2$.

Scheme 13

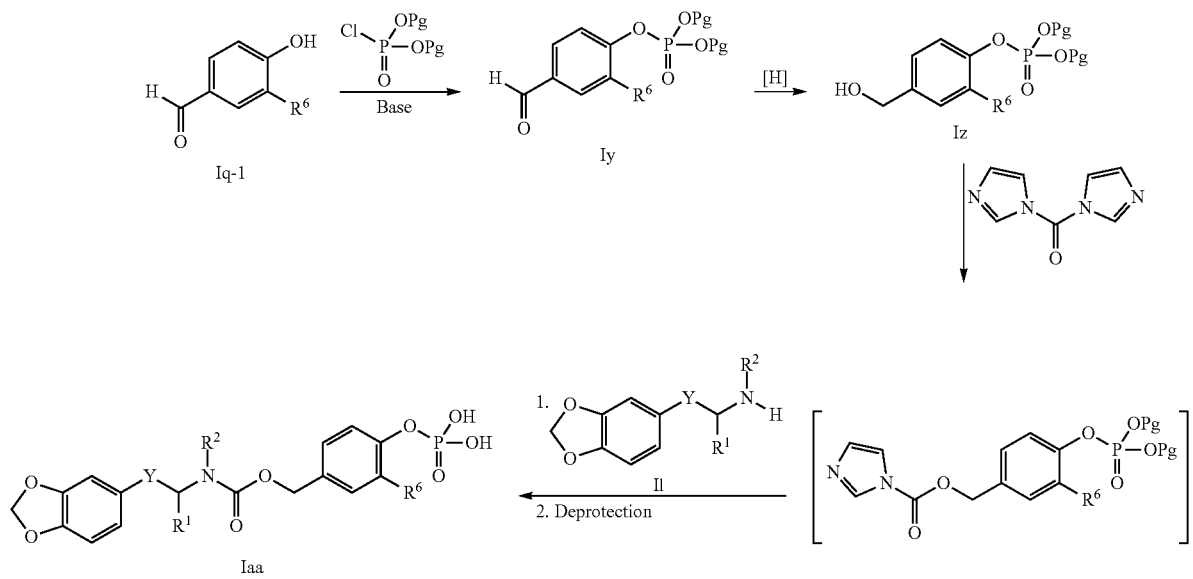

Scheme 14

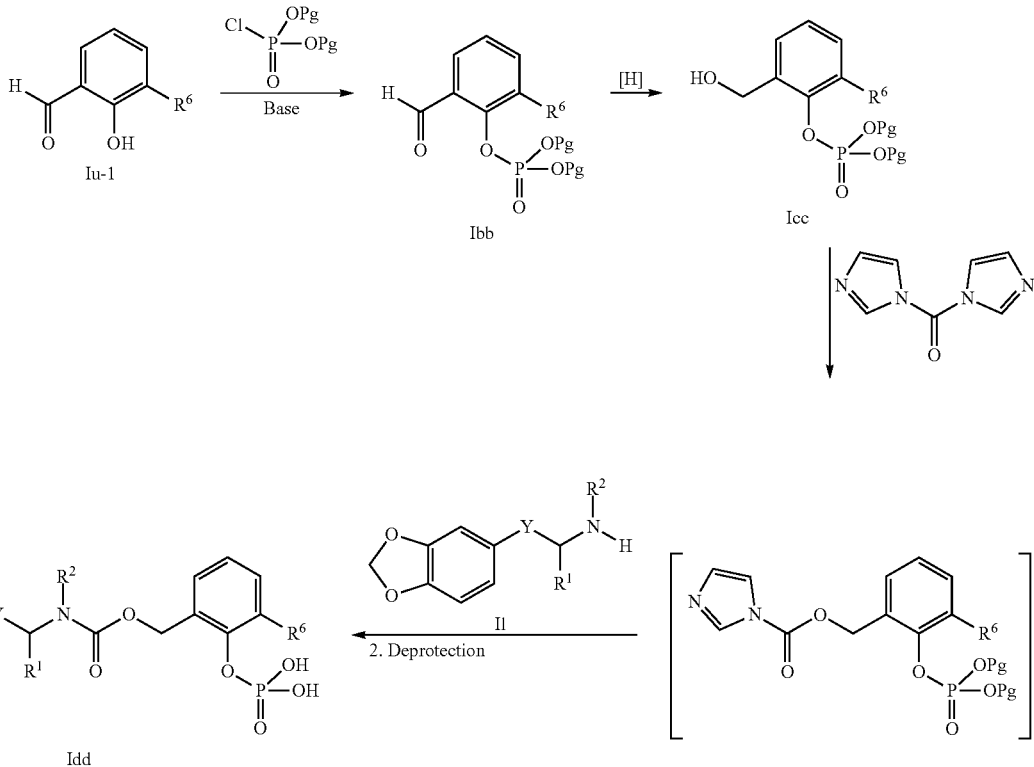

The amide prodrug of Formula Ihh may be prepared by coupling the requisite amine II with the carboxylic acid Igg as presented in Scheme 15 below. Such a carboxylic acid may be generated by a 3-step sequence starting with the phenol Iee that may be prepared according to the synthesis reported by Nicolaou M. G. et al. (*J. Org. Chem,* 1996, 61, 8636). Acylation of Iee may be performed by reaction of the phenol with a carboxylic acid (Z=OH) in the presence of a coupling reagent, such as N,N-dicyclohexylcarbodiimide (DCC), N-ethyl-N'-(3-dimethylaminopropyl)-carbodiimide (EDC), 1,1-carbonyldiimidazole (CDI), diisopropylcarbodiimide (DIC), hexafluorophosphate benzotriazole tetramethyl uronium (HBTU) and hexafluorophosphate azabenzotriazole tetramethyl uranium (HATU) or other similar reagents well known to one skilled in the art. Alternatively, the phenol Iee may also be reacted with an acid chloride (Z=Cl) or with an anhydride (Z=—OC(O)$R^3$ or —OC(O) t-Butyl) in the presence of a base such as diisopropylethylamine (DIPEA), triethylamine, 4-methylmorpholine, $NaHCO_3$, $K_2CO_3$ or 2,6-lutidine in an appropriate solvent such as methylene chloride, THF, DMF, acetonitrile, or toluene. Deprotection of Iff may be accomplished under mild acidic conditions (Pg=TBS) using a reagent such as PPTS in a solvent such as methanol (Crouch, R. D. *Tetrahedron,* 2013, 69, 2383) or under reductive conditions (Pg=benzyl) using Pd/C as a catalyst in a solvent such as methanol under an atmosphere of $H_2$. The corresponding primary alcohol may be oxidized using a reagent such as Jones' reagent in a solvent such as acetone to afford the carboxylic acid Igg which may then be coupled with the amine II in the presence of a coupling reagent as described above.

Scheme 15

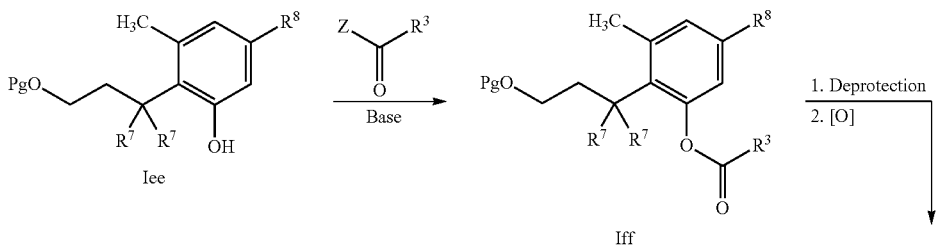

-continued

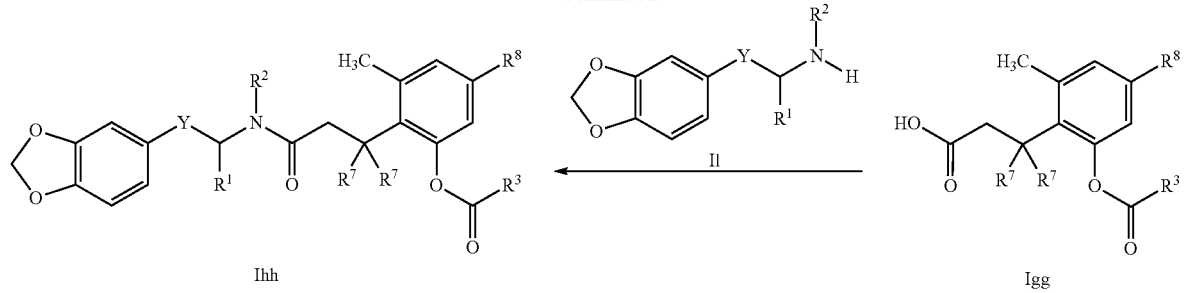

Ihh

Igg

The phosphonate prodrug of Formula Ijj may be prepared by coupling the requisite amine II with the carboxylic acid Iii as depicted in Scheme 16 below. Such a carboxylic acid may be obtained according to the synthesis reported by Nicolaou M. G. et al. (*J. Org. Chem,* 1996, 61, 8636). Amide bound formation may be performed by reaction of requisite amine II with the carboxylic acid Iii in the presence of a coupling reagent, such as N,N-dicyclohexylcarbodiimide (DCC), N-ethyl-N'-(3-dimethylaminopropyl)-carbodiimide (EDC), 1,1-carbonyldiimidazole (CDI), diisopropylcarbodiimide (DIC), hexafluorophosphate benzotriazole tetramethyl uronium (HBTU) and hexafluorophosphate azabenzotriazole tetramethyl uranium (HATU) or other similar reagents well known to one skilled in the art. The phosphonate prodrug Ijj may be obtained by deprotection of the corresponding di-benzylphosphate under reductive conditions using Pd/C as a catalyst in a solvent such as methanol under an atmosphere of $H_2$.

reaction of the phenol with a carboxylic acid (Z=OH) in the presence of a coupling reagent, such as N,N-dicyclohexylcarbodiimide (DCC), N-ethyl-N'-(3-dimethylaminopropyl)-carbodiimide (EDC), 1,1-carbonyldiimidazole (CDI), diisopropylcarbodiimide (DIC), hexafluorophosphate benzotriazole tetramethyl uronium (HBTU) and hexafluorophosphate azabenzotriazole tetramethyl uranium (HATU) or other similar reagents well known to one skilled in the art. Alternatively, the phenol Ikk may also be reacted with an acid chloride (Z=Cl) or with an anhydride (Z=—OC(O)R$^3$ or —OC(O)t-Butyl) in the presence of a base such as diisopropylethylamine (DIPEA), triethylamine, 4-methylmorpholine, NaHCO$_3$, K$_2$CO$_3$ or 2,6-lutidine in an appropriate solvent such as methylene chloride, THF, DMF, acetonitrile, or toluene. Deprotection of ILL may be accomplished under mild acidic conditions (Pg=TBS) using a reagent such as AcOH in a solvent mixture such as THF/H$_2$O. The corresponding primary alcohol may be oxidized to Scheme 16

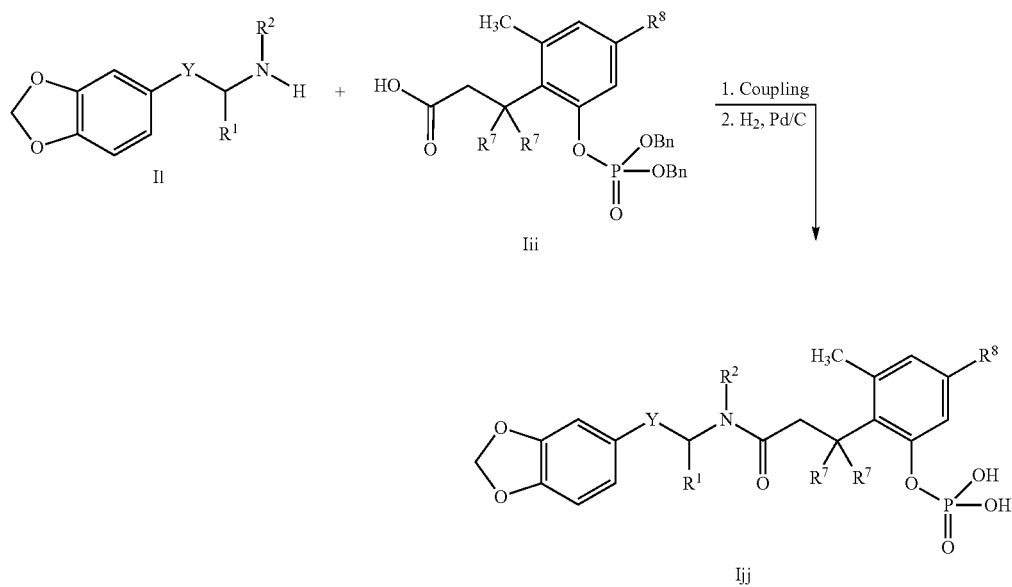

The amide prodrug of Formula Inn may be prepared by coupling the requisite amine II with the carboxylic acid Imm as presented in Scheme 17 below. Such a carboxylic acid may be generated by a 4-step sequence starting with the phenol Ikk that may be prepared according to the synthesis reported by Liao Y. and Wang B. (*Bioorg. Med. Chem. Lett.,* 1999, 9, 1795). Acylation of Ikk may be performed by the carboxylic acid Imm in a 2-step sequence where the alcohol is first oxidized to the aldehyde using a reagent such as MnO$_2$ in a solvent such as dichloromethane followed by a Kraus type reaction using reagents well known to one skilled in the art. Finally, coupling of the carboxylic acid Imm with the amine II may be performed in the presence of a coupling reagent as described above to afford the prodrug Inn.

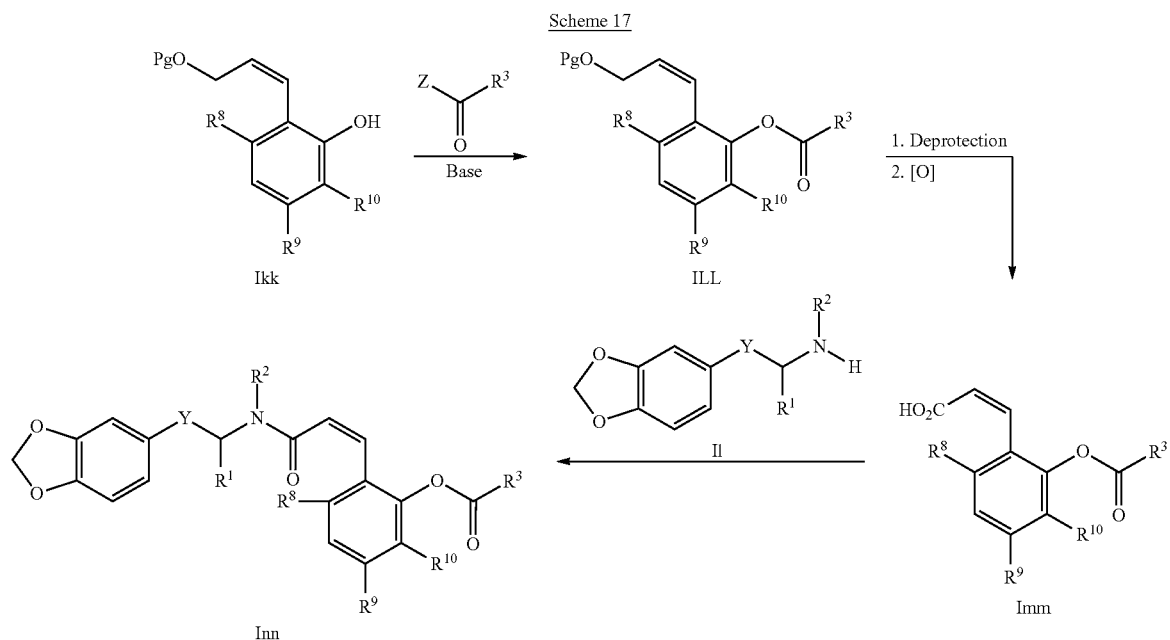
Examples of the compounds of Formula (I) according to the invention include any one of the compounds 1-402 of Table 1, 2 and 3 compounds 403-511 of Table 4 below (as well as pharmaceutically acceptable salts of any of these compounds):

TABLE 1-continued
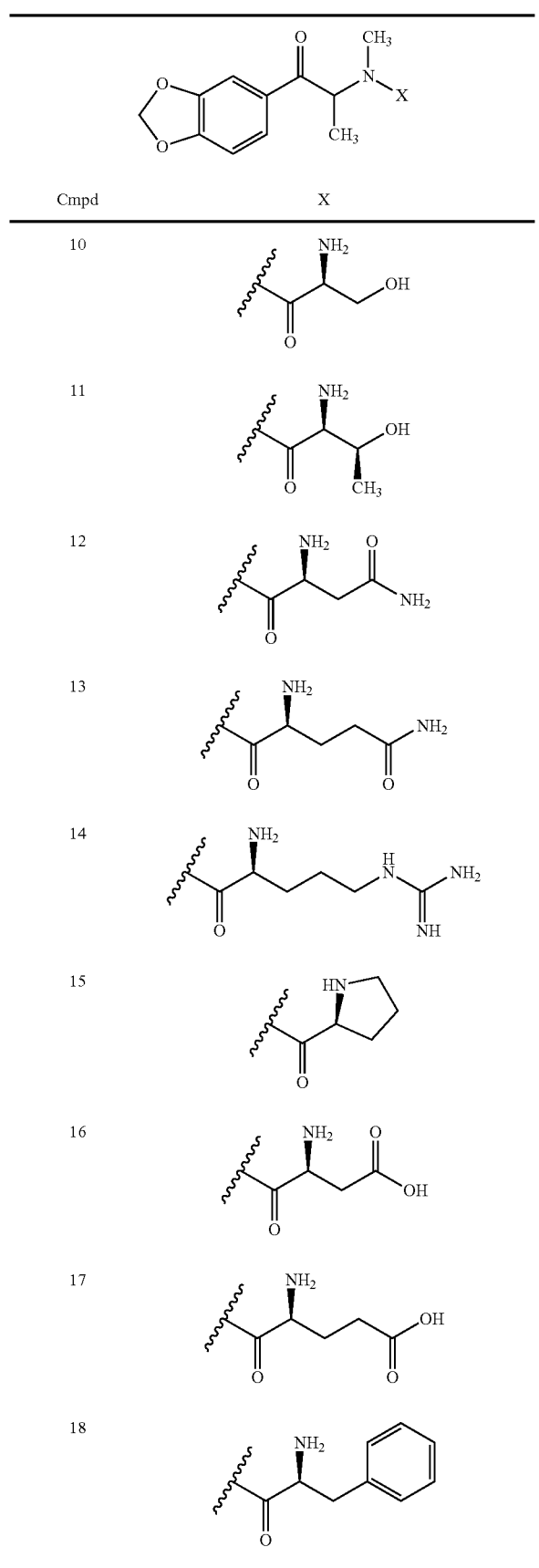
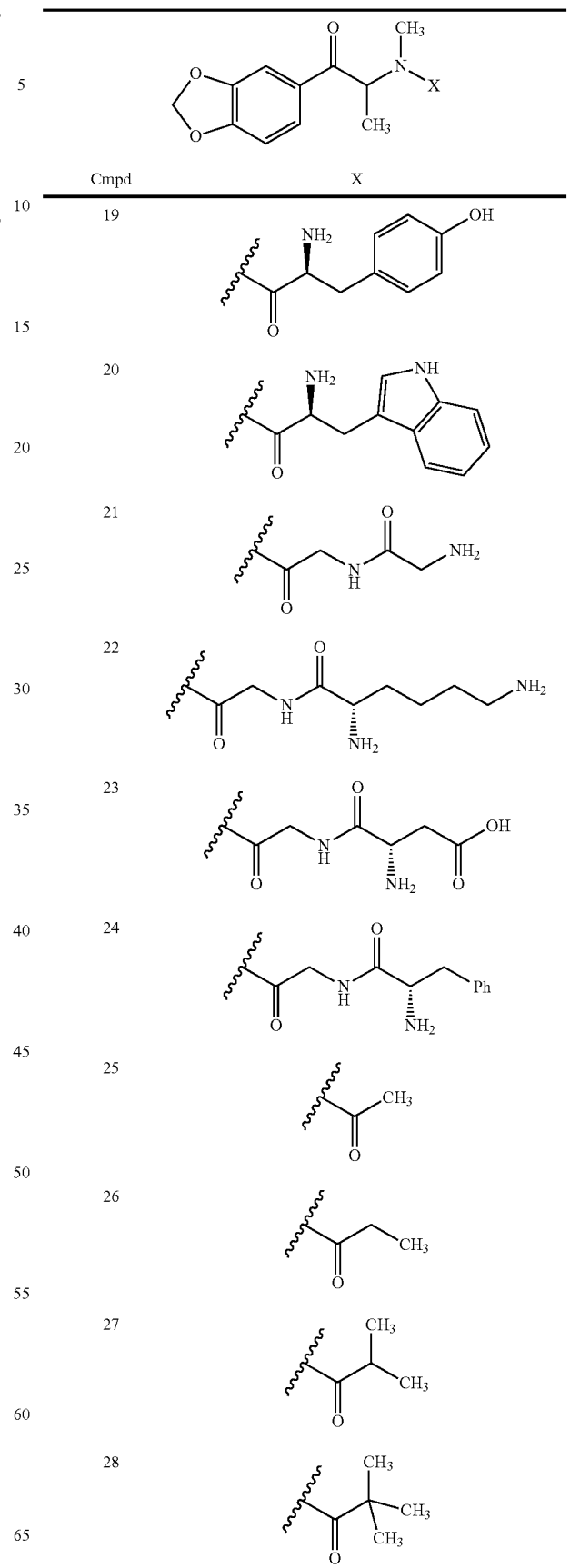

TABLE 1-continued

[Structure: 1-(benzo[d][1,3]dioxol-5-yl)-2-(N-methyl-N-X-amino)propan-1-one]

| Cmpd | X |
|------|---|
| 29 | -C(=O)-CH₂-CH(CH₃)₂ (isobutyl ketone) |
| 30 | -C(=O)-CH₂-CH₂-CH₃ (butanoyl) |
| 31 | -C(=O)-cyclopropyl |
| 32 | -C(=O)-cyclobutyl |
| 33 | -C(=O)-cyclopentyl |
| 34 | -C(=O)-cyclohexyl |
| 35 | -C(=O)-CH₂-CH₂-C(=O)OH |
| 36 | -C(=O)-CH₂-CH₂-CH₂-N(CH₃)₂ |
| 37 | -C(=O)-phenyl |
| 38 | -C(=O)-(4-nitrophenyl) |
| 39 | -C(=O)-(4-methoxyphenyl) |
| 40 | -C(=O)-(pyridin-2-yl) |
| 41 | -C(=O)-(pyridin-3-yl) |
| 42 | -C(=O)-(pyridin-4-yl) |
| 43 | -C(=O)-(1H-imidazol-2-yl) |
| 44 | -C(=O)-CCl₃ |
| 45 | -C(=O)-CF₃ |
| 46 | -C(=O)-O-CH₂-O-P(=O)(OH)₂ |

TABLE 1-continued

| Cmpd | X |
|---|---|
| 47 | [phosphate ester: -C(O)O-CH(CH3)-O-P(O)(OH)2] |
| 48 | [-C(O)O-CH(CH3)-O-C(O)CH3] |
| 49 | [-C(O)O-CH(CH3)-O-C(O)CH2CH3] |
| 50 | [-C(O)O-CH(CH3)-O-C(O)CH(CH3)2] |
| 51 | [-C(O)O-CH(CH3)-O-C(O)C(CH3)3] |
| 52 | [-C(O)O-CH(CH3)-O-C(O)(CH2)3CH3] |
| 53 | [-C(O)O-CH(CH3)-O-C(O)-cyclopropyl] |
| 54 | [-C(O)O-CH2-O-C(O)CH3] |
| 55 | [-C(O)O-CH2-O-C(O)CH2CH3] |
| 56 | [-C(O)O-CH2-O-C(O)CH(CH3)2] |

TABLE 1-continued

| Cmpd | X |
|---|---|
| 57 | [-C(O)O-CH2-O-C(O)C(CH3)3] |
| 58 | [-C(O)O-CH2-O-C(O)(CH2)2CH3] |
| 59 | [-C(O)O-CH2-O-C(O)-cyclopropyl] |
| 60 | [-CH2CH2-O-C(O)CH3] |
| 61 | [-CH2CH2-O-C(O)CH2CH3] |
| 62 | [-CH2CH2-O-C(O)CH(CH3)2] |
| 63 | [-CH2CH2-O-C(O)C(CH3)3] |
| 64 | [-CH2CH2-O-C(O)CH2CH(CH3)2] |
| 65 | [-CH2CH2-O-C(O)(CH2)2CH3] |
| 66 | [-CH2CH2-O-C(O)-cyclopropyl] |

TABLE 1-continued

Structure: 1-(benzo[d][1,3]dioxol-5-yl)-2-(N-methyl-N-X-amino)propan-1-one

| Cmpd | X |
|---|---|
| 67 | –CH₂CH₂OC(O)CH₂CH₂C(O)OH |
| 68 | –CH₂CH₂OC(O)CH₂CH(OH)CH₂OH |
| 69 | –CH₂CH₂OC(O)CH₂CH₂CH₂N(CH₃)₂ |
| 70 | CH₂OPO(OH)₂ |
| 71 | –C(O)OCH₃ |
| 72 | –C(O)OCH₂CH₃ |
| 73 | –C(O)OCH(CH₃)₂ |
| 74 | –C(O)OC(CH₃)₃ |
| 75 | –C(O)OCH₂CH(CH₃)₂ |
| 76 | –C(O)OCH₂CH₂CH₂CH₃ |
| 77 | –C(O)OCH₂CH₂CH₂CH₂CH₃ |
| 78 | –C(O)OCF₃ |
| 79 | –C(O)OCCl₃ |
| 80 | –C(O)O-cyclopropyl |
| 81 | –C(O)OCH₂CH(OH)CH₂OH |
| 82 | –C(O)OCH₂CH₂CH₂N(CH₃)₂ |
| 83 | –C(O)OCH₂CH₂C(O)OH |
| 84 | PO(OH)₂ |
| 85 | –C(O)CH₂CH₂CH₂NHC(O)CH₃ |
| 86 | –C(O)CH₂CH₂CH₂NHC(O)CH(CH₃)₂ |
| 87 | –C(O)CH₂CH₂CH₂NHC(O)CH₂NH₂ |
| 88 | –C(O)CH₂CH₂CH₂OC(O)CH₃ |

TABLE 1-continued

| Cmpd | X |
|---|---|
| 89 | -C(=O)-CH₂CH₂-C(=O)-O-CH₂CH₂-O-C(=O)-CH(CH₃)₂ |
| 90 | -C(=O)-CH₂CH₂CH₂-O-C(=O)-CH₂-NH₂ |
| 91 | -C(=O)-CH₂CH₂CH₂-O-P(=O)(OH)₂ |
| 92 | -C(=O)-CH₂CH₂CH₂CH₂-NH-C(=O)-CH₃ |
| 93 | -C(=O)-CH₂CH₂CH₂CH₂-NH-C(=O)-CH₂-NH₂ |
| 94 | -C(=O)-O-CH₂-(4-OC(=O)CH₃-phenyl) |
| 95 | -C(=O)-O-CH₂-(4-OC(=O)CH(CH₃)₂-phenyl) |
| 96 | -C(=O)-O-CH₂-(4-OC(=O)CH₃-3-NO₂-phenyl) |
| 97 | -C(=O)-O-CH₂-(4-OC(=O)CH(CH₃)₂-3-NO₂-phenyl) |
| 98 | -C(=O)-O-CH₂-(4-NHC(=O)CH₃-phenyl) |
| 99 | -C(=O)-O-CH₂-(4-NHC(=O)CH(CH₃)₂-phenyl) |
| 100 | -C(=O)-O-CH₂-(4-NHC(=O)CH₃-3-NO₂-phenyl) |
| 101 | -C(=O)-O-CH₂-(4-NHC(=O)CH(CH₃)₂-3-NO₂-phenyl) |
| 102 | -C(=O)-O-CH₂-(4-NHC(=O)CH₂NH₂-3-NO₂-phenyl) |
| 103 | -C(=O)-O-CH₂-(4-OP(=O)(OH)₂-phenyl) |
| 104 | -C(=O)-O-CH₂-(2-OC(=O)CH₃-phenyl) |

TABLE 1-continued
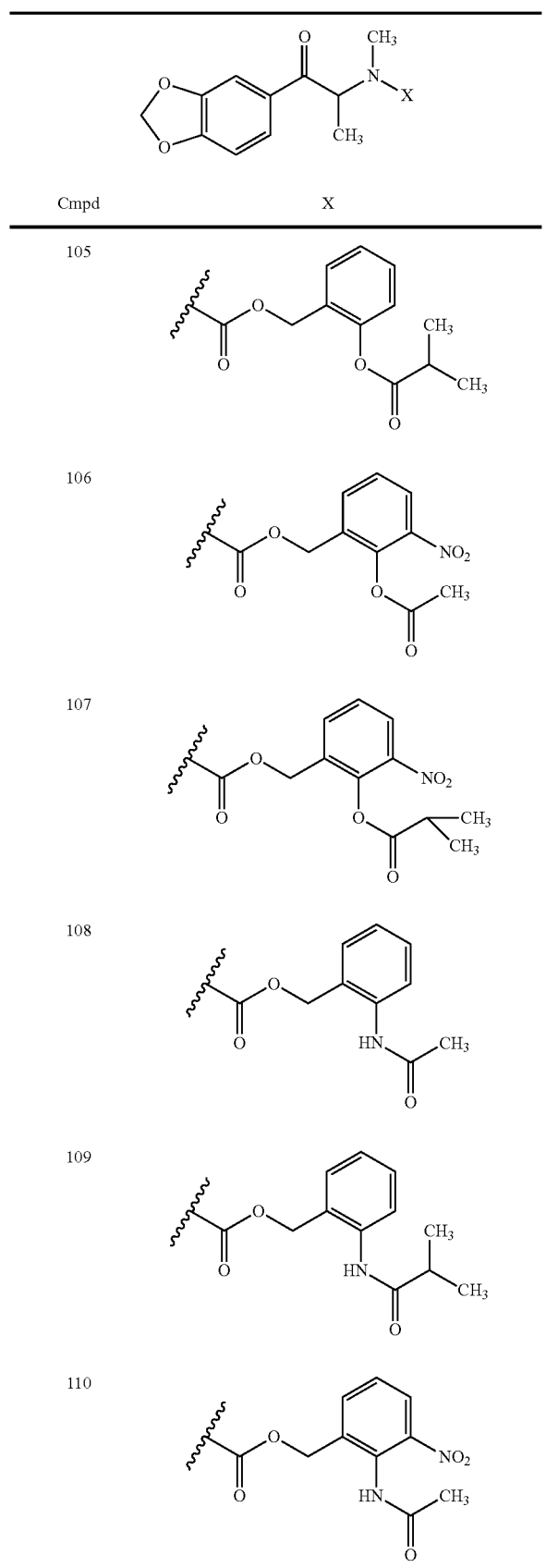
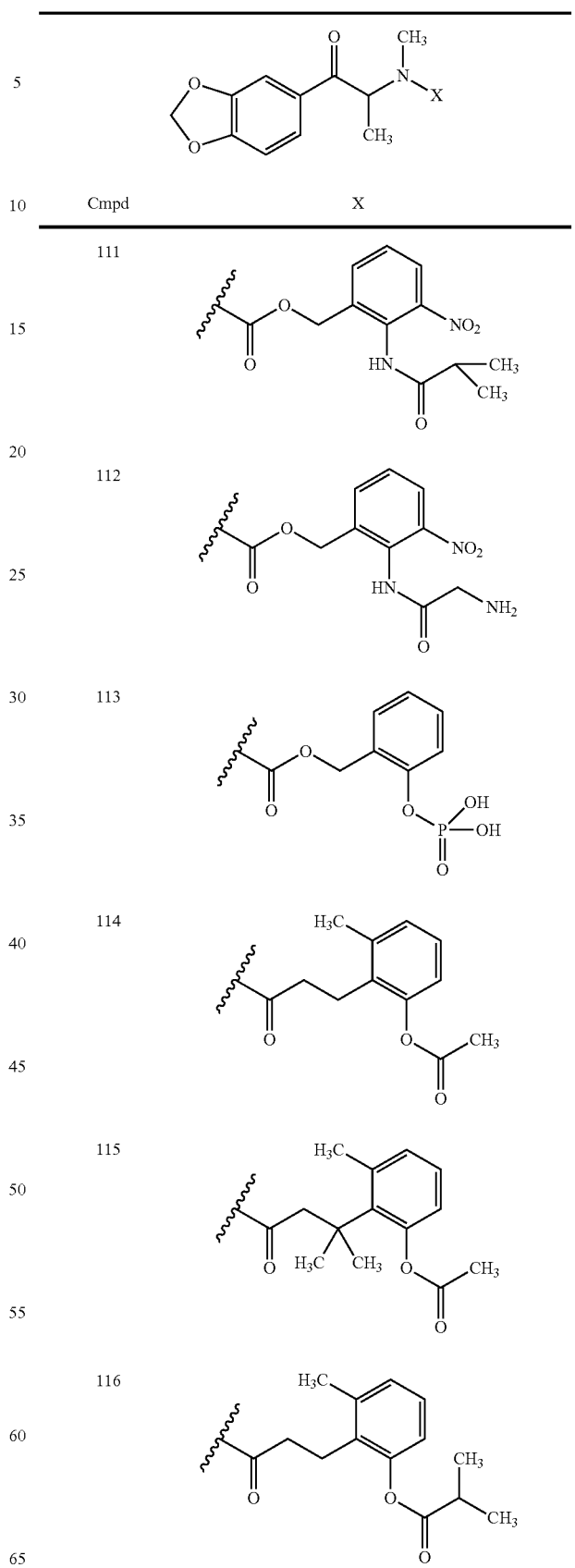

TABLE 1-continued
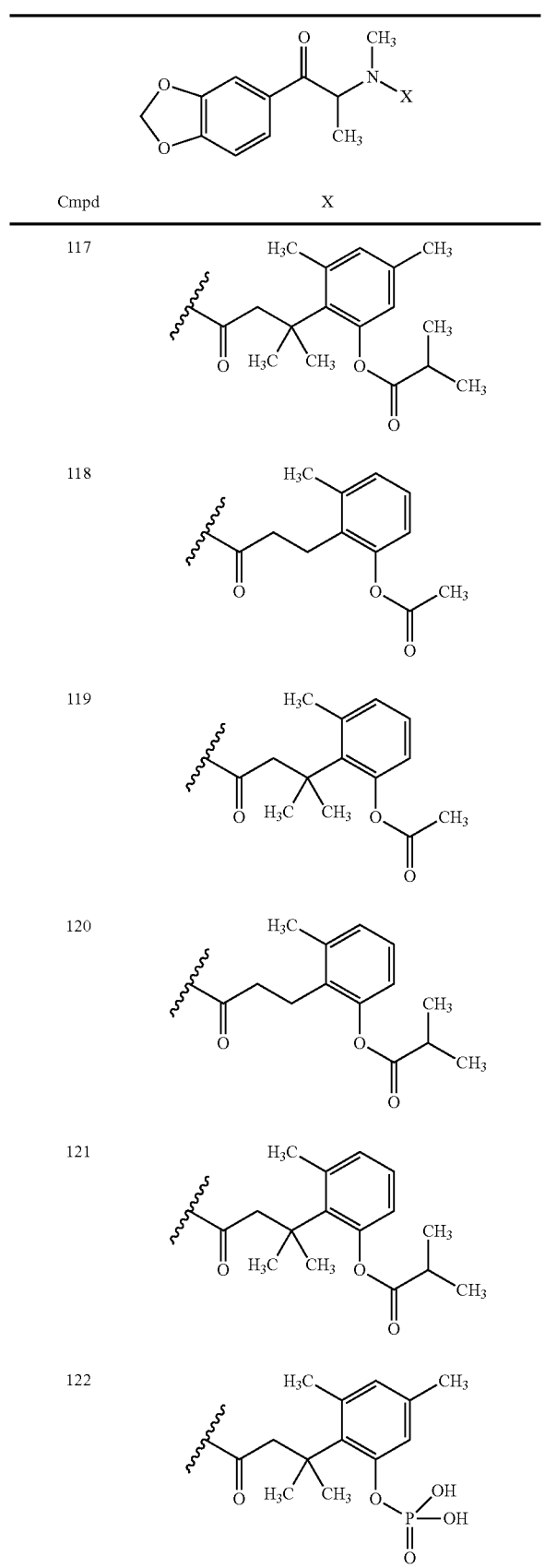
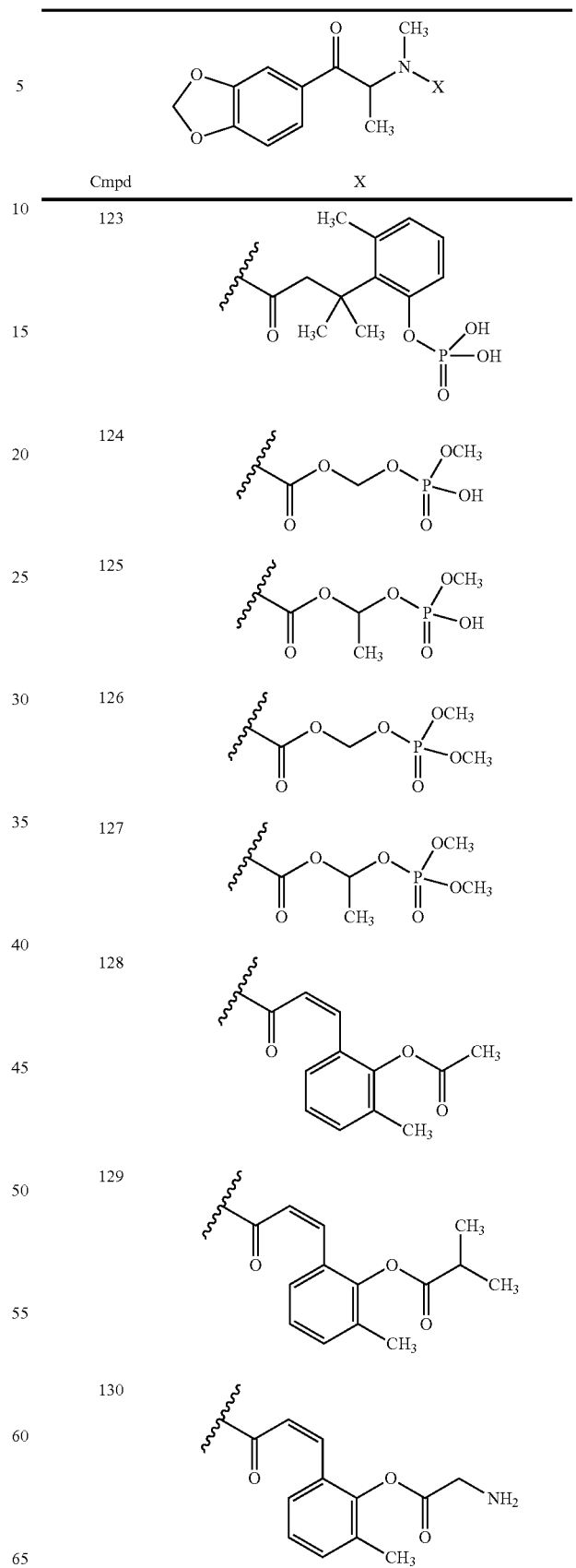

TABLE 1-continued

[Structure: 1-(benzo[d][1,3]dioxol-5-yl)-2-(N-methyl-N-X-amino)propan-1-one]

| Cmpd | X |
|---|---|
| 131 | [cinnamoyl group with 2-acetoxyphenyl] |
| 132 | [cinnamoyl group with 3-acetoxy-2,4,6-trimethylphenyl] |
| 133 | [cinnamoyl group with 3-acetoxy-2,6-dimethylphenyl] |
| 134 | [cinnamoyl group with 2-acetoxy-3,4-dimethylphenyl] |

TABLE 2

[Structure: 1-(benzo[d][1,3]dioxol-5-yl)-2-(N-methyl-N-X-amino)butan-1-one]

| Cmpd | X |
|---|---|
| 135 | [lysyl] |
| 136 | [glycyl] |
| 137 | [alanyl] |
| 138 | [valyl] |
| 139 | [leucyl] |
| 140 | [isoleucyl] |
| 141 | [methionyl] |
| 142 | [cysteinyl] |
| 143 | [histidyl] |
| 144 | [seryl] |
| 145 | [threonyl] |

TABLE 2-continued
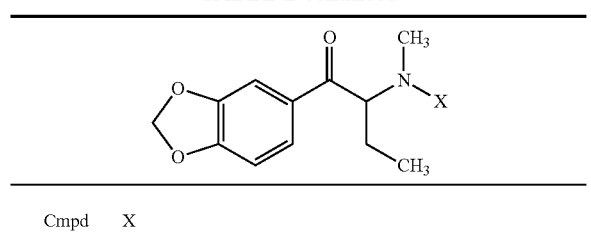
| Cmpd | X |
|---|---|
| 146 | 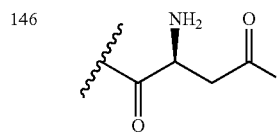 |
| 147 | 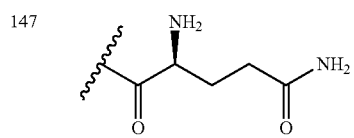 |
| 148 | 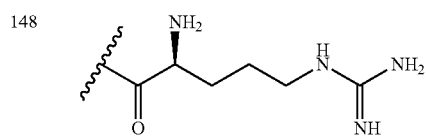 |
| 149 | 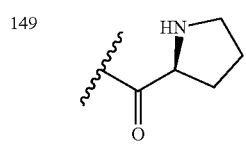 |
| 150 | 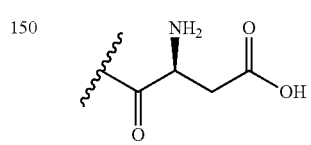 |
| 151 | 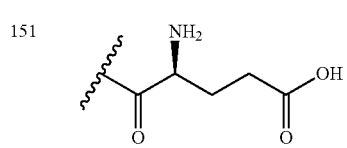 |
| 152 | 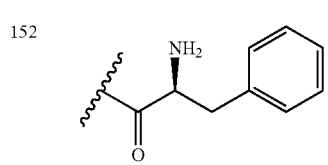 |
| 153 | 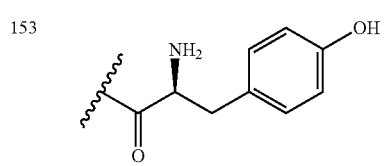 |
| 154 | 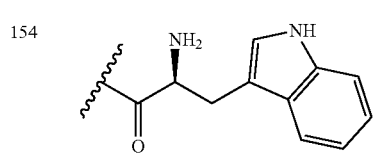 |
TABLE 2-continued
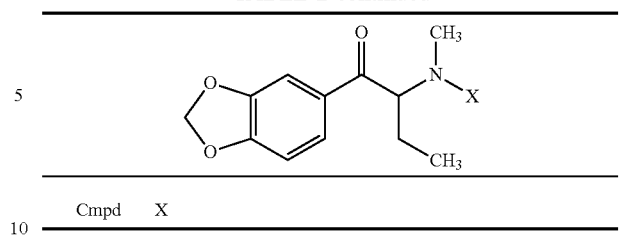
| Cmpd | X |
|---|---|
| 155 | 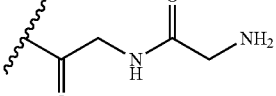 |
| 156 | 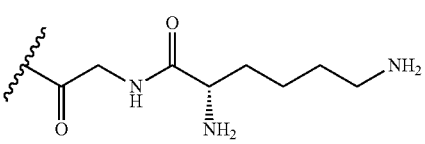 [SMILES: *C(=O)CNC(=O)[C@@H](N)CCCCN] |
| 157 | 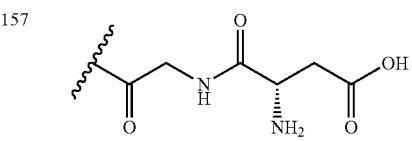 |
| 158 | 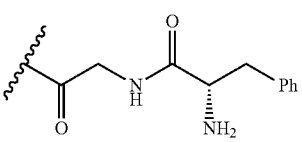 [SMILES: *C(=O)CNC(=O)[C@@H](N)Cc1ccccc1] |
| 159 | 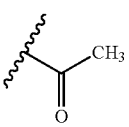 |
| 160 | 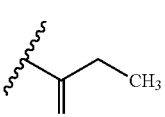 |
| 161 | 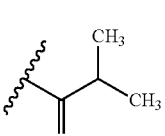 |
| 162 | 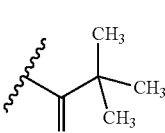 |
| 163 | 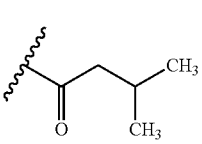 |
| 164 | 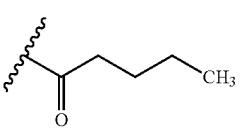 [SMILES: *C(=O)CCCC] |

TABLE 2-continued
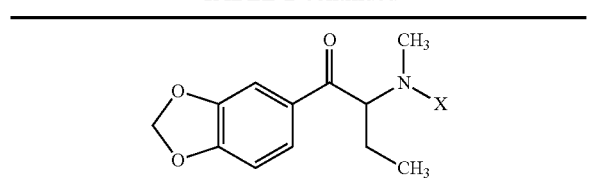
| Cmpd | X |
|---|---|
| 165 | 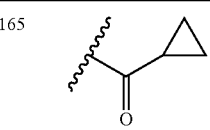 |
| 166 | 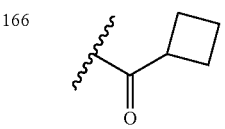 |
| 167 | 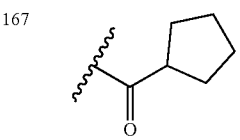 |
| 168 | 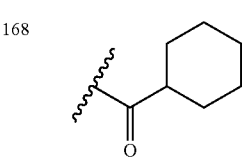 |
| 169 | 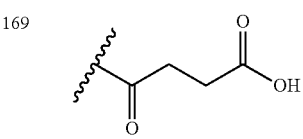 |
| 170 | 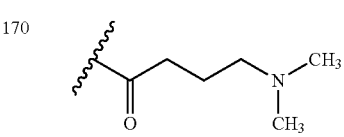 |
| 171 | 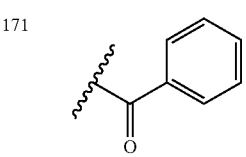 |
| 172 | 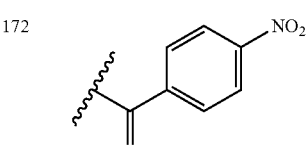 |
| 173 | 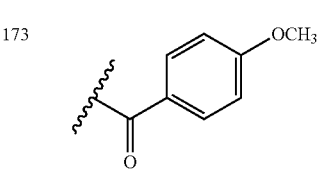 |
TABLE 2-continued
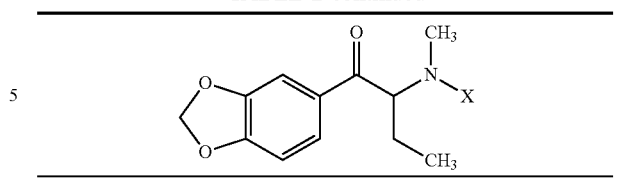
| Cmpd | X |
|---|---|
| 174 | 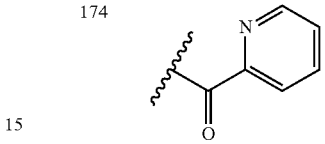 |
| 175 | 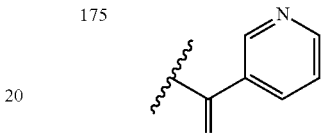 |
| 176 | 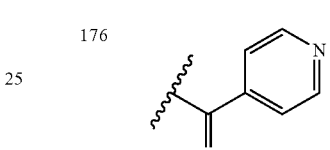 |
| 177 | 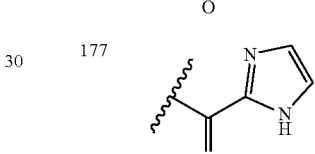 |
| 178 | 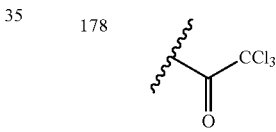 |
| 179 | 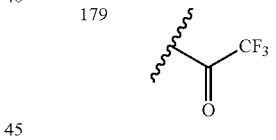 |
| 180 | 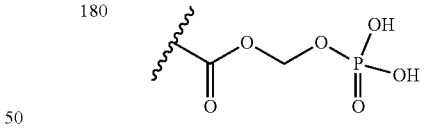 |
| 181 | 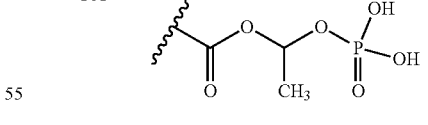 |
| 182 | 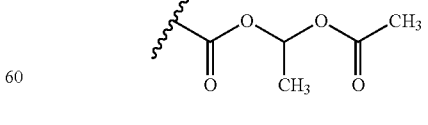 |
| 183 | 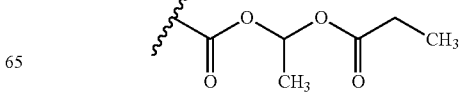 |

TABLE 2-continued
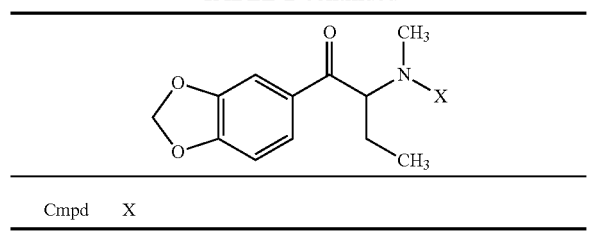
| Cmpd | X |
|---|---|
| 184 | 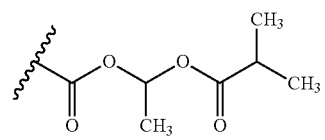 [SMILES: *C(=O)OC(C)OC(=O)C(C)C] |
| 185 | 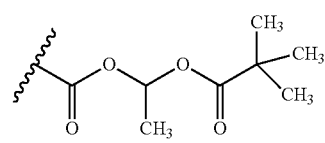 |
| 186 | 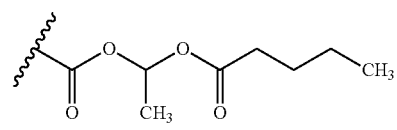 [SMILES: *C(=O)OC(C)OC(=O)CCCC] |
| 187 | 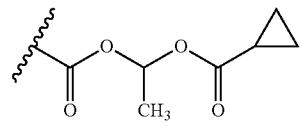 [SMILES: *C(=O)OC(C)OC(=O)C1CC1] |
| 188 | 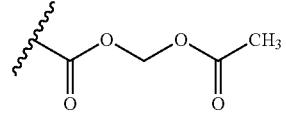 [SMILES: *C(=O)OCOC(C)=O] |
| 189 | 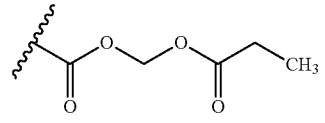 [SMILES: *C(=O)OCOC(=O)CC] |
| 190 | 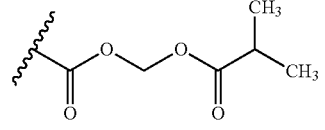 [SMILES: *C(=O)OCOC(=O)C(C)C] |
| 191 | 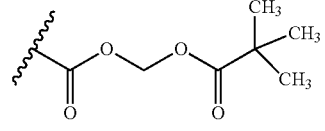 [SMILES: *C(=O)OCOC(=O)C(C)(C)C] |
| 192 | 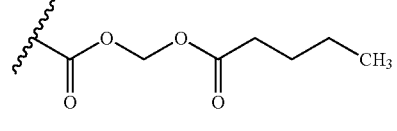 [SMILES: *C(=O)OCOC(=O)CCCC] |
| 193 | 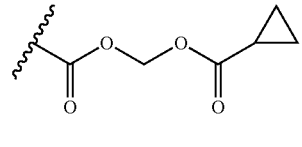 [SMILES: *C(=O)OCOC(=O)C1CC1] |
TABLE 2-continued
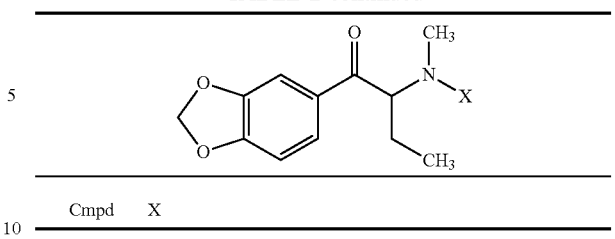
| Cmpd | X |
|---|---|
| 194 | 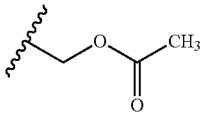 [SMILES: *COC(C)=O] |
| 195 | 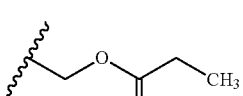 |
| 196 | 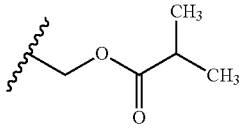 [SMILES: *COC(=O)C(C)C] |
| 197 | 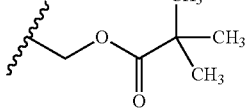 |
| 198 | 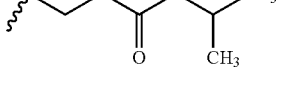 |
| 199 | 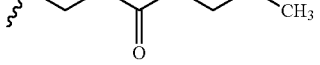 |
| 200 | 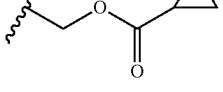 |
| 201 | 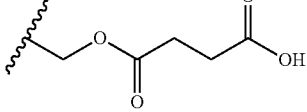 |
| 202 | 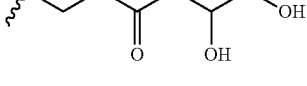 |
| 203 | 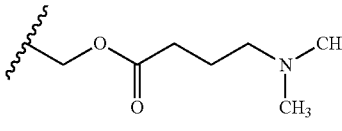 |
| 204 | $CH_2OPO(OH)_2$ |

TABLE 2-continued

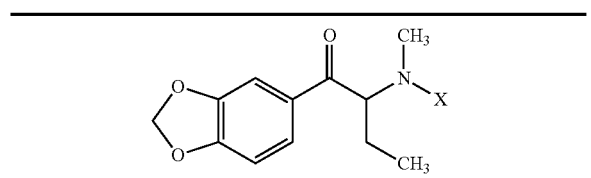

| Cmpd | X |
|---|---|
| 205 | methyl ester (–C(O)OCH₃) |
| 206 | ethyl ester |
| 207 | isopropyl ester |
| 208 | tert-butyl ester |
| 209 | isobutyl ester |
| 210 | n-butyl ester |
| 211 | n-pentyl ester |
| 212 | –C(O)OCF₃ |
| 213 | –C(O)OCCl₃ |
| 214 | cyclopropyl ester |

TABLE 2-continued

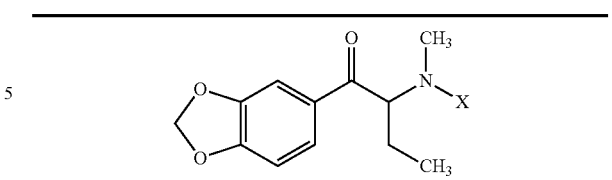

| Cmpd | X |
|---|---|
| 215 | glyceryl ester (–C(O)OCH₂CH(OH)CH₂OH) |
| 216 | –C(O)OCH₂CH₂CH₂N(CH₃)₂ |
| 217 | –C(O)OCH₂CH₂C(O)OH |
| 218 | PO(OH)₂ |
| 219 | –C(O)CH₂CH₂CH₂NHC(O)CH₃ |
| 220 | –C(O)CH₂CH₂CH₂NHC(O)CH(CH₃)₂ |
| 221 | –C(O)CH₂CH₂CH₂NHC(O)CH₂NH₂ |
| 222 | –C(O)CH₂CH₂CH₂OC(O)CH₃ |
| 223 | –C(O)CH₂CH₂CH₂OC(O)CH(CH₃)₂ |
| 224 | –C(O)CH₂CH₂CH₂OC(O)CH₂NH₂ |

TABLE 2-continued
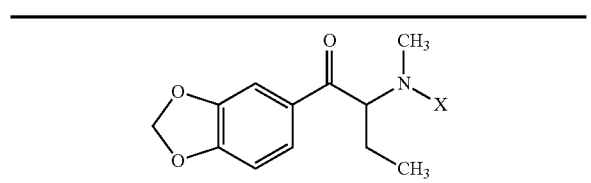
| Cmpd | X |
|---|---|
| 225 | 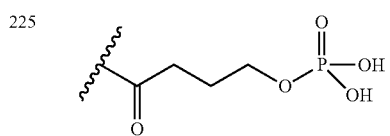 |
| 226 | 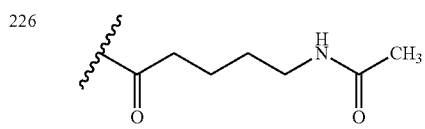 |
| 227 | 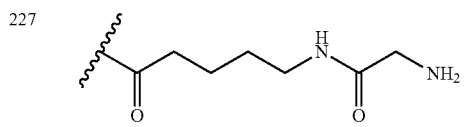 |
| 228 | 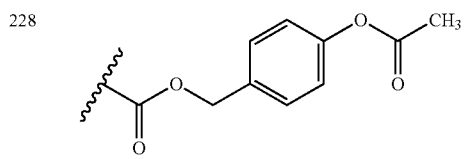 |
| 229 | 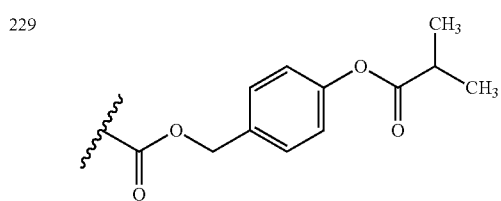 |
| 230 | 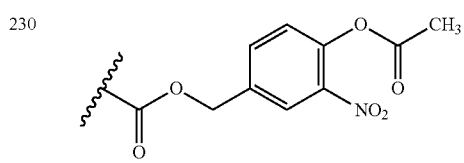 |
| 231 | 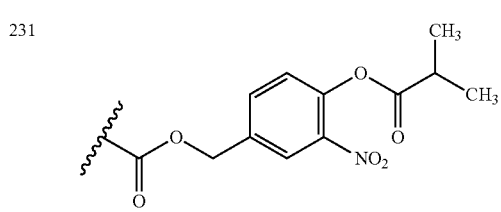 |
| 232 | 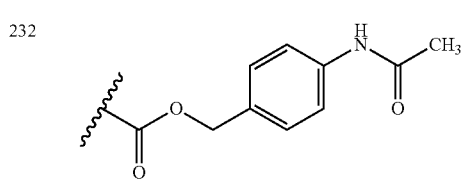 |
TABLE 2-continued
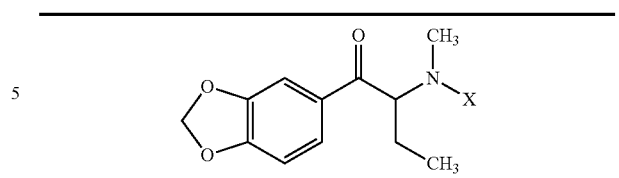
| Cmpd | X |
|---|---|
| 233 | 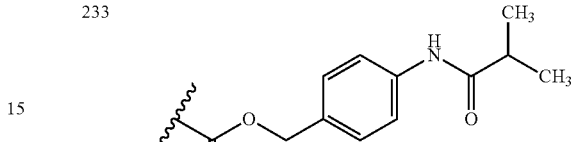 |
| 234 | 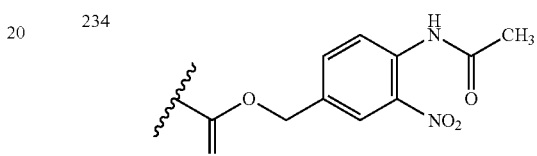 |
| 235 | 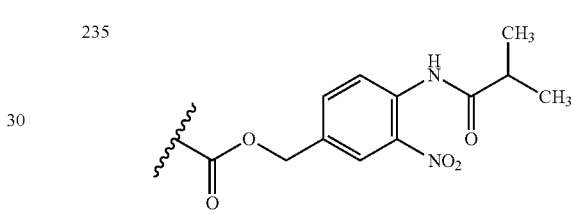 |
| 236 | 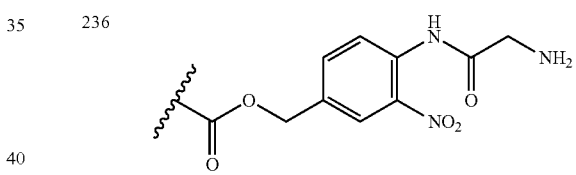 |
| 237 | 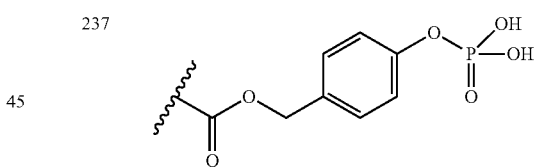 |
| 238 | 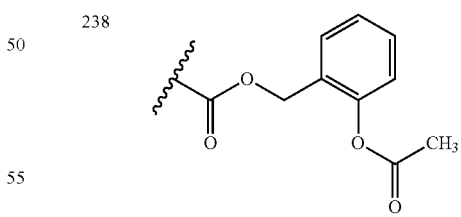 |
| 239 | 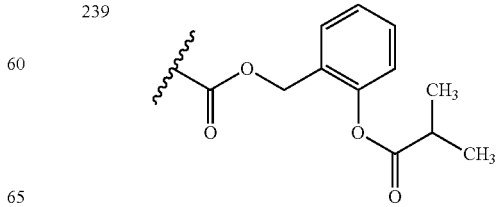 |

TABLE 2-continued
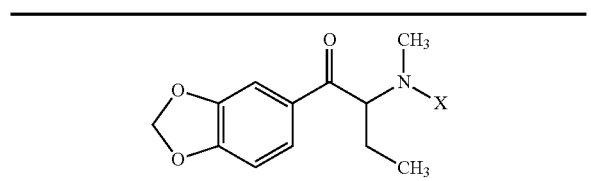
| Cmpd | X |
|---|---|
| 240 | |
| 241 | |
| 242 | |
| 243 | |
| 244 | |
| 245 | |
TABLE 2-continued
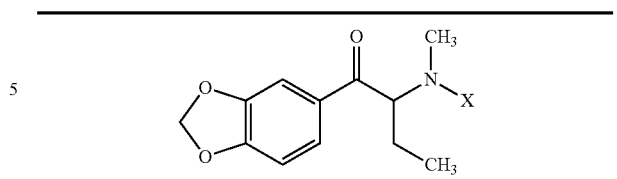
| Cmpd | X |
|---|---|
| 246 | |
| 247 | |
| 248 | |
| 249 | |
| 250 | |
| 251 | |

TABLE 2-continued
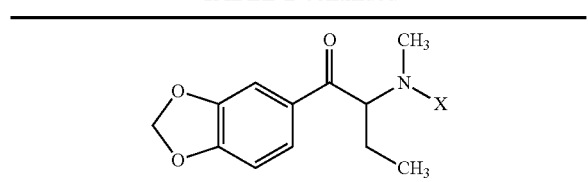
| Cmpd | X |
|------|---|
| 252 | |
| 253 | |
| 254 | |
| 255 | |
| 256 | |
| 257 | |
TABLE 2-continued
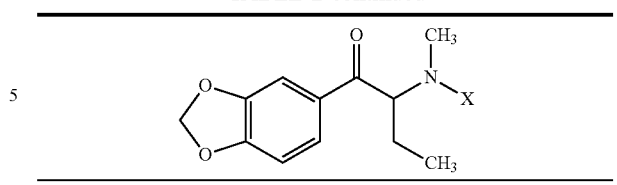
| Cmpd | X |
|------|---|
| 258 | |
| 259 | |
| 260 | |
| 261 | |
| 262 | |
| 263 | |
| 264 | |
| 265 | |

TABLE 2-continued
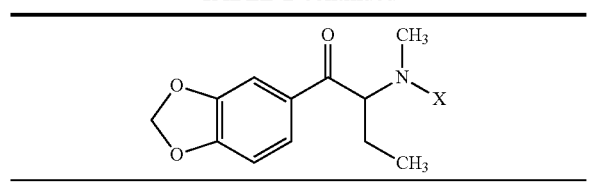
| Cmpd | X |
|---|---|
| 266 | 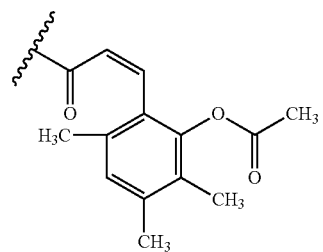 [SMILES: *C(=O)/C=C\c1c(C)cc(C)c(C)c1OC(C)=O] |
| 267 | 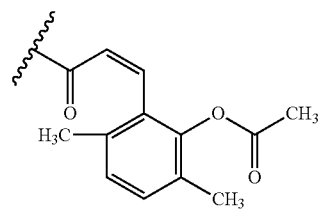 |
| 268 | 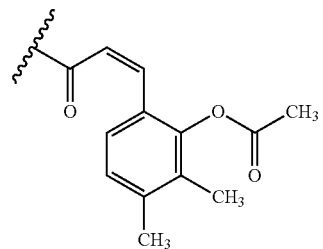 [SMILES: *C(=O)/C=C\c1ccc(C)c(C)c1OC(C)=O] |
TABLE 3
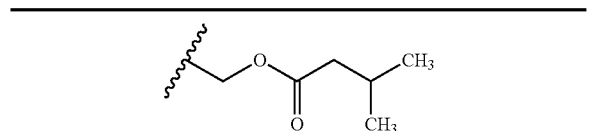
| Cmpd | X |
|---|---|
| 269 | 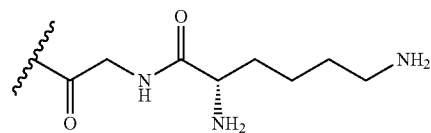 [SMILES: *C(=O)CNC(=O)[C@@H](N)CCCCN] |
| 270 | 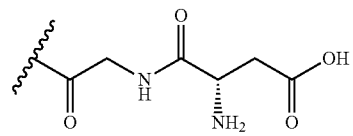 [SMILES: *C(=O)CNC(=O)[C@@H](N)CC(=O)O] |
| 271 | 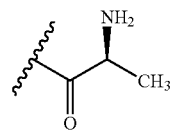 |
TABLE 3-continued
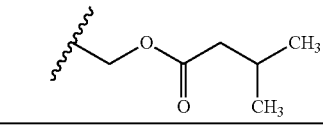
| Cmpd | X |
|---|---|
| 272 | 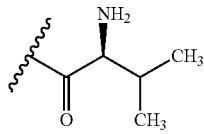 |
| 273 | 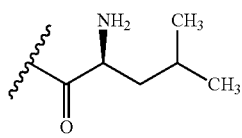 [SMILES: *C(=O)[C@@H](N)CC(C)C] |
| 274 | 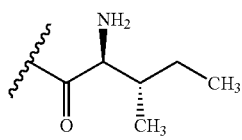 |
| 275 | 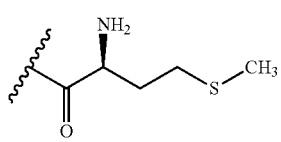 [SMILES: *C(=O)[C@@H](N)CCSC] |
| 276 | 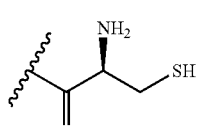 |
| 277 | 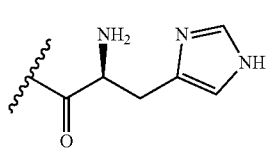 [SMILES: *C(=O)[C@@H](N)Cc1c[nH]cn1] |
| 278 | 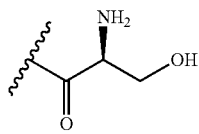 [SMILES: *C(=O)[C@@H](N)CO] |
| 279 | 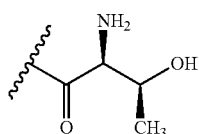 |
| 280 | 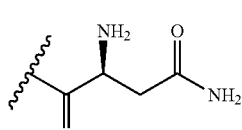 |
| 281 | 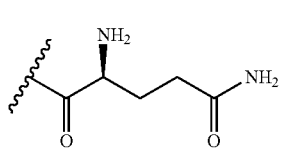 [SMILES: *C(=O)[C@@H](N)CCC(N)=O] |

TABLE 3-continued
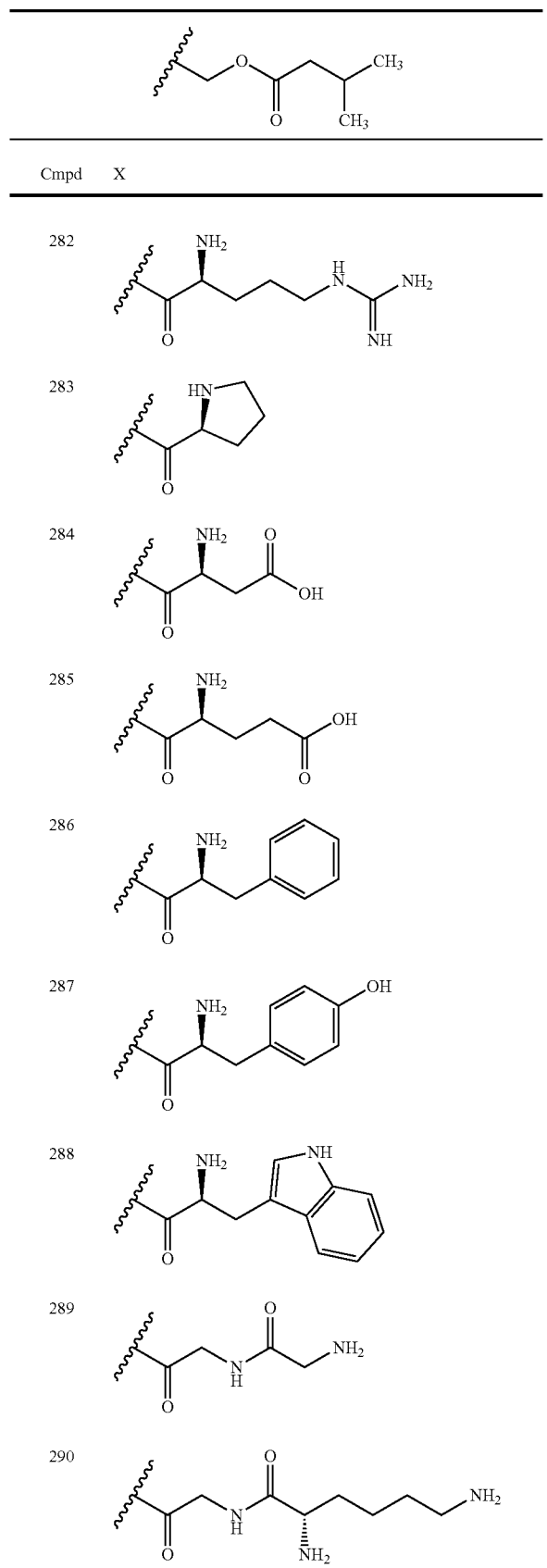
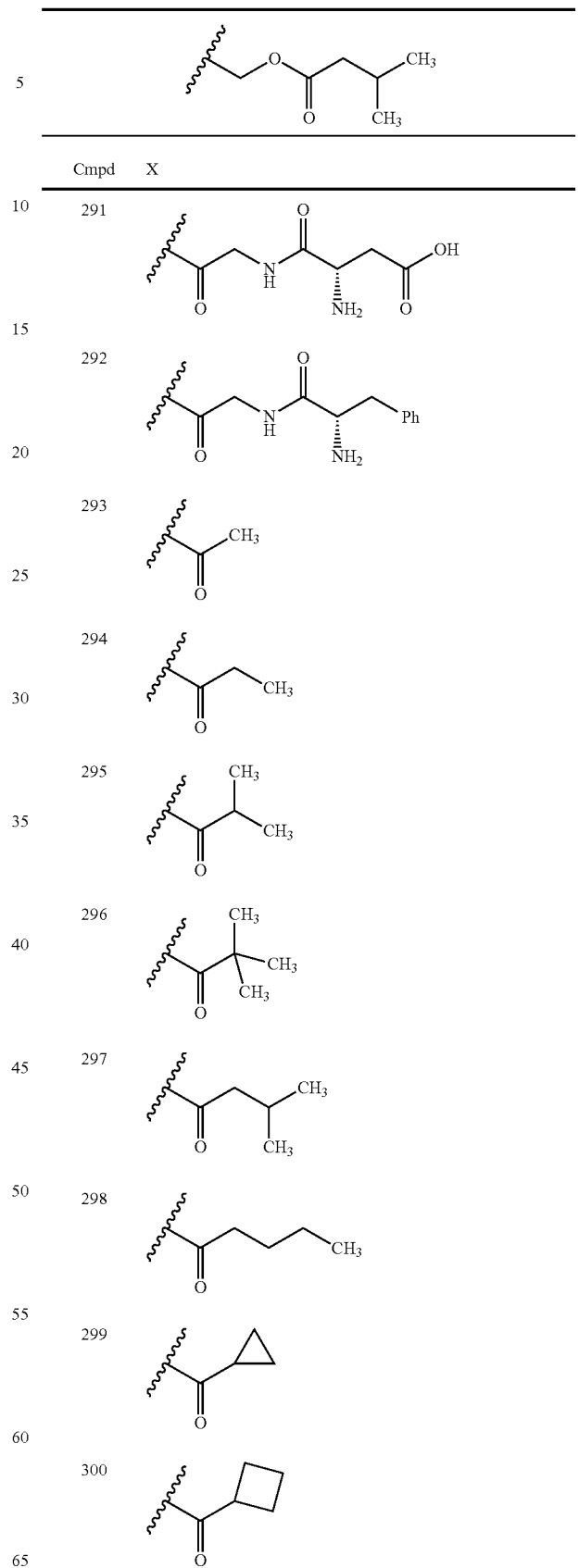

TABLE 3-continued
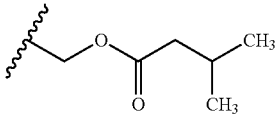
| Cmpd | X |
|---|---|
| 301 | 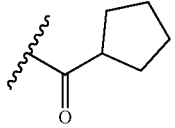 [SMILES: *C(=O)C1CCCC1] |
| 302 | 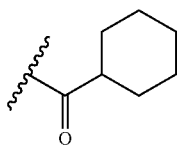 [SMILES: *C(=O)C1CCCCC1] |
| 303 | 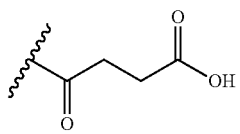 [SMILES: *C(=O)CCC(=O)O] |
| 304 | 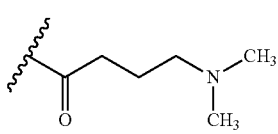 [SMILES: *C(=O)CCCN(C)C] |
| 305 | 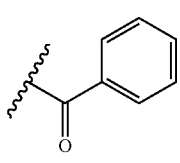 [SMILES: *C(=O)c1ccccc1] |
| 306 | 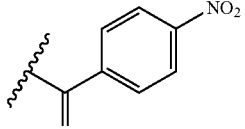 |
| 307 | 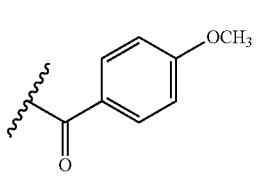 [SMILES: *C(=O)c1ccc(OC)cc1] |
| 308 | 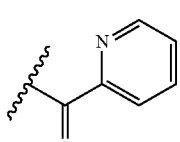 |
| 309 | 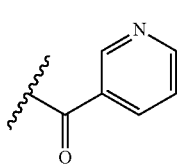 [SMILES: *C(=O)c1cccnc1] |
TABLE 3-continued
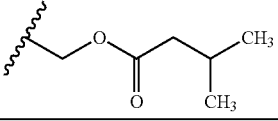
| Cmpd | X |
|---|---|
| 310 | 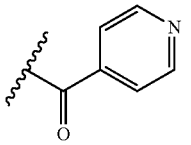 |
| 311 | 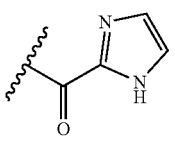 [SMILES: *C(=O)c1ncc[nH]1] |
| 312 | 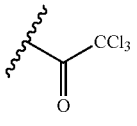 |
| 313 | 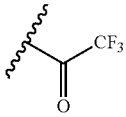 |
| 314 | 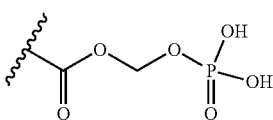 [SMILES: *C(=O)OCOP(=O)(O)O] |
| 315 | 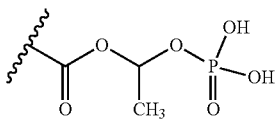 |
| 316 | 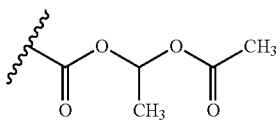 [SMILES: *C(=O)OC(C)OC(C)=O] |
| 317 | 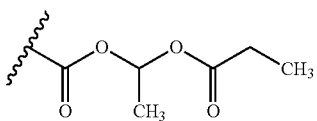 |
| 318 | 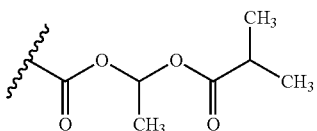 |
| 319 | 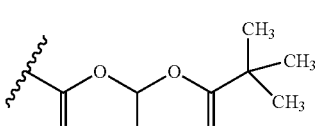 |

TABLE 3-continued
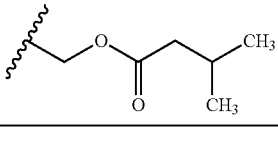
| Cmpd | X |
|---|---|
| 320 | 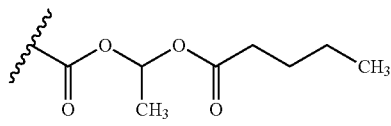 |
| 321 | 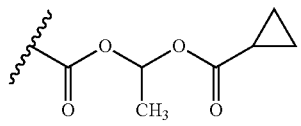 |
| 322 | 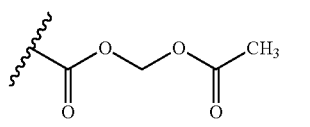 [SMILES: *C(=O)OCOC(C)=O] |
| 323 | 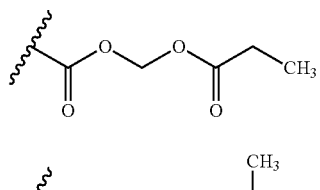 |
| 324 | 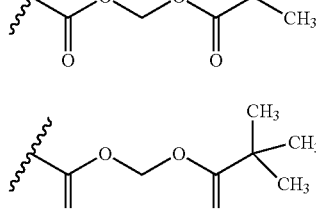 |
| 325 | 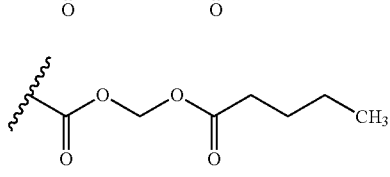 |
| 326 | 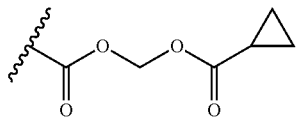 [SMILES: *C(=O)OCOC(=O)C1CC1] |
| 327 | 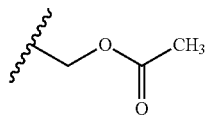 [SMILES: *COC(C)=O] |
| 328 | 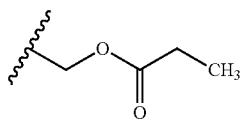 [SMILES: *COC(=O)CC] |
| 329 | 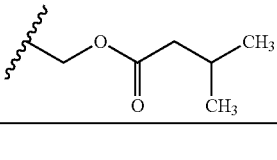 |
TABLE 3-continued
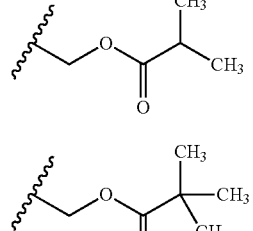
| Cmpd | X |
|---|---|
| 330 | 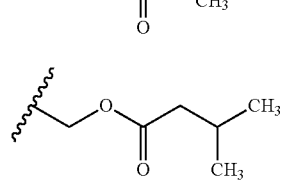 |
| 331 | 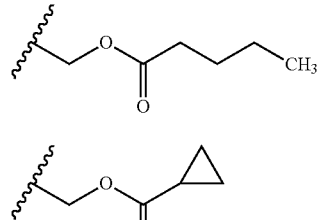 |
| 332 |  |
| 333 | 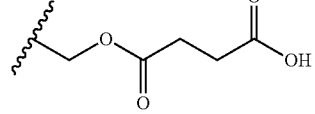 |
| 334 | 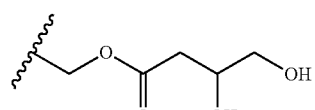 |
| 335 | 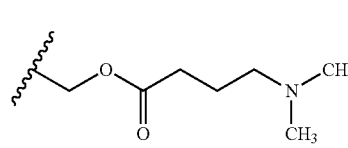 |
| 336 | 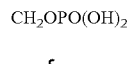 |
| 337 | 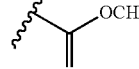 |
| 338 | $CH_2OPO(OH)_2$ |
| 339 | 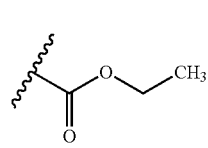 [SMILES: *C(=O)OCC] |
| 340 |  |

TABLE 3-continued
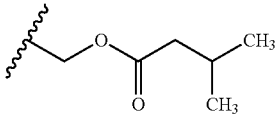
| Cmpd | X |
|---|---|
| 341 | 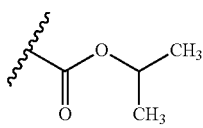 |
| 342 | 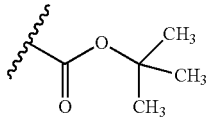 |
| 343 | 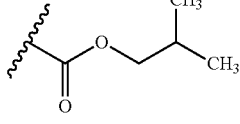 |
| 344 | 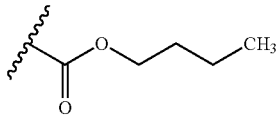 [SMILES: *C(=O)OCCCC] |
| 345 | 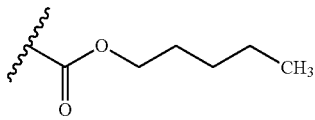 [SMILES: *C(=O)OCCCCC] |
| 346 | 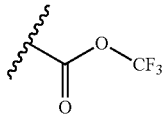 [SMILES: *C(=O)OC(F)(F)F] |
| 347 | 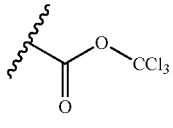 |
| 348 | 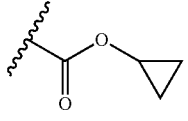 [SMILES: *C(=O)OC1CC1] |
| 349 | 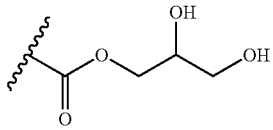 |
| 350 | 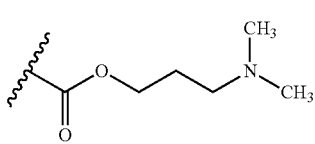 [SMILES: *C(=O)OCCCN(C)C] |
TABLE 3-continued
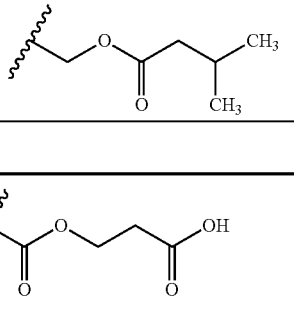
| Cmpd | X |
|---|---|
| 351 | 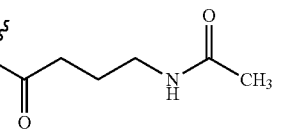 |
| 352 | PO(OH)$_2$ |
| 353 | 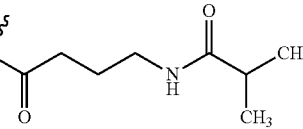 |
| 354 | 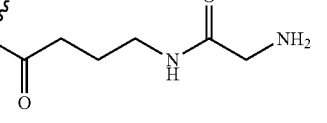 |
| 355 | 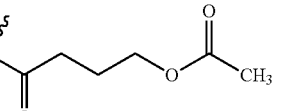 |
| 356 | 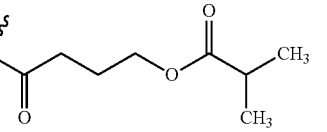 |
| 357 | 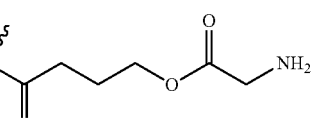 |
| 358 | 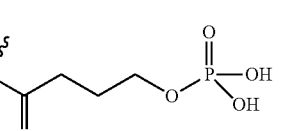 |
| 359 | 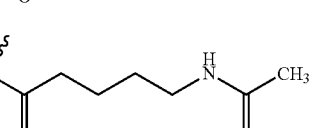 |
| 360 | 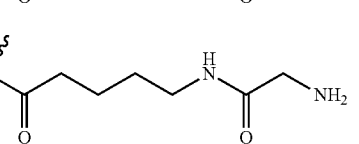 |
| 361 |  |

TABLE 3-continued
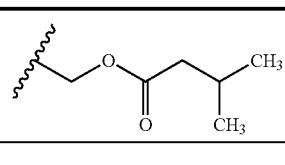
| Cmpd | X |
|---|---|
| 362 | 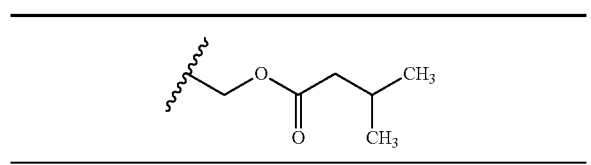 |
| 363 | 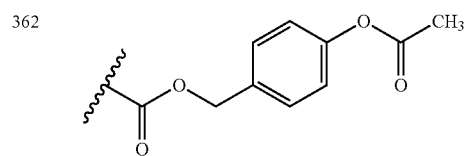 |
| 364 | 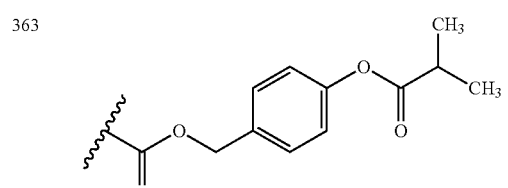 |
| 365 | 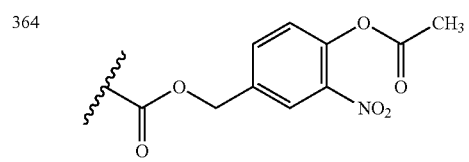 |
| 366 | 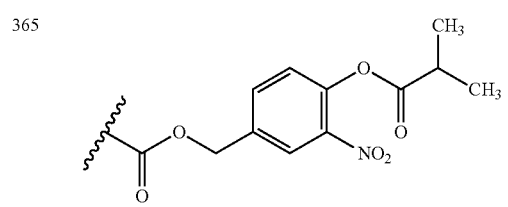 |
| 367 | 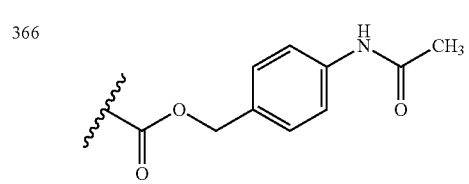 |
| 368 | 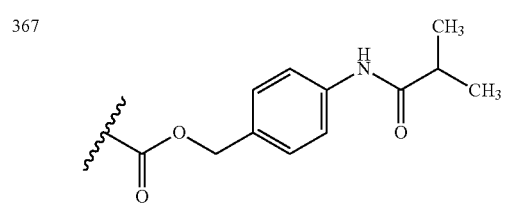 |
TABLE 3-continued
| Cmpd | X |
|---|---|
| 369 | 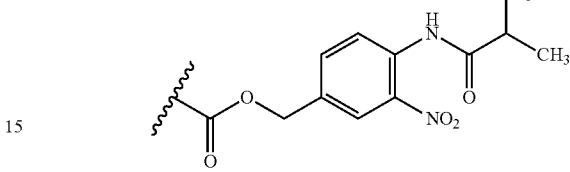 |
| 370 | 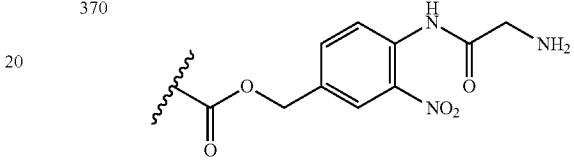 |
| 371 | 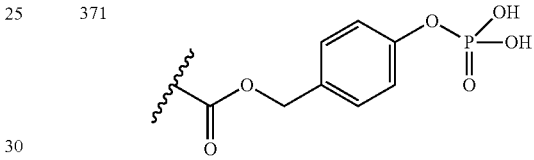 |
| 372 | 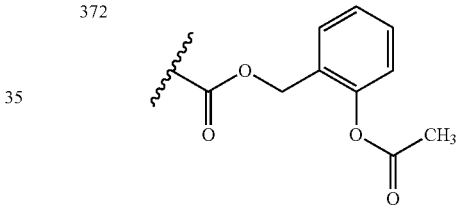 |
| 373 | 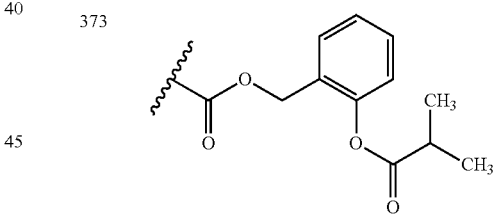 |
| 374 | 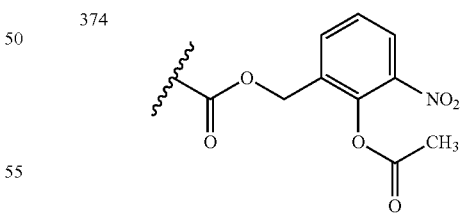 |
| 375 | 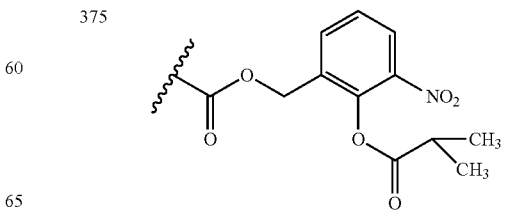 |

TABLE 3-continued
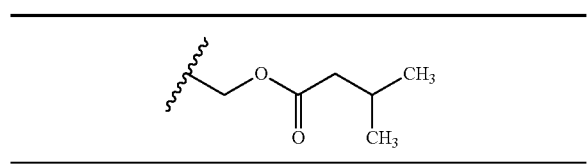
| Cmpd | X |
|---|---|
| 376 | 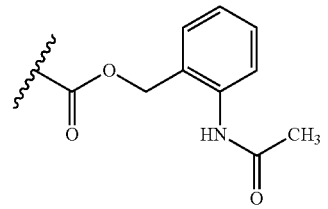 [SMILES: *C(=O)OCc1ccccc1NC(C)=O] |
| 377 | 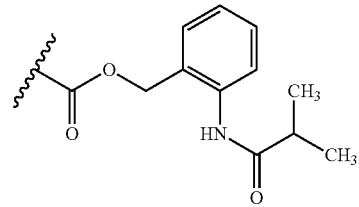 [SMILES: *C(=O)OCc1ccccc1NC(=O)C(C)C] |
| 378 | 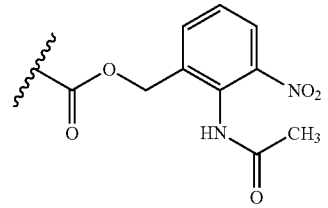 [SMILES: *C(=O)OCc1cccc([N+](=O)[O-])c1NC(C)=O] |
| 379 | 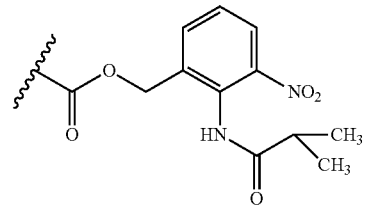 [SMILES: *C(=O)OCc1cccc([N+](=O)[O-])c1NC(=O)C(C)C] |
| 380 | 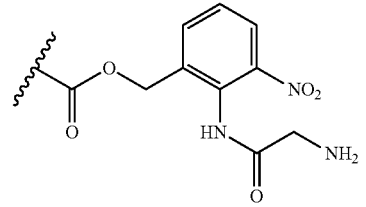 [SMILES: *C(=O)OCc1cccc([N+](=O)[O-])c1NC(=O)CN] |
| 381 | 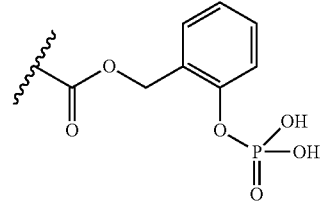 [SMILES: *C(=O)OCc1ccccc1OP(=O)(O)O] |
TABLE 3-continued
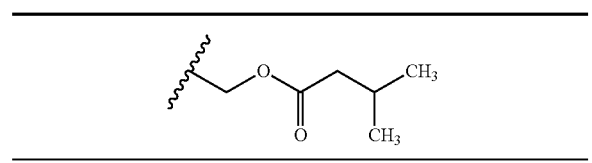
| Cmpd | X |
|---|---|
| 382 | 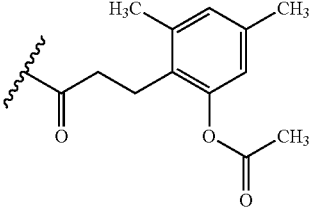 [SMILES: *C(=O)CCc1c(C)cc(C)cc1OC(C)=O] |
| 383 | 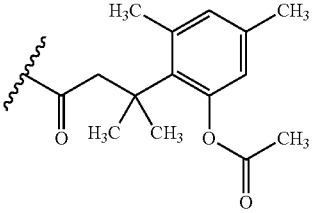 [SMILES: *C(=O)CC(C)(C)c1c(C)cc(C)cc1OC(C)=O] |
| 384 | 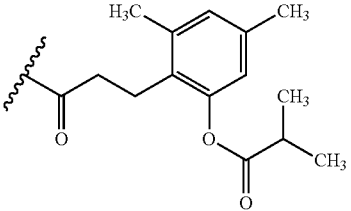 [SMILES: *C(=O)CCc1c(C)cc(C)cc1OC(=O)C(C)C] |
| 385 | 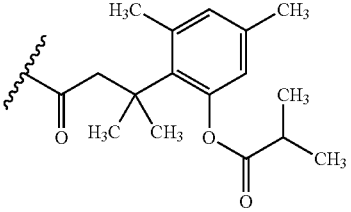 [SMILES: *C(=O)CC(C)(C)c1c(C)cc(C)cc1OC(=O)C(C)C] |
| 386 | 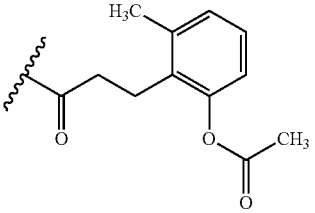 [SMILES: *C(=O)CCc1c(C)cccc1OC(C)=O] |
| 387 | 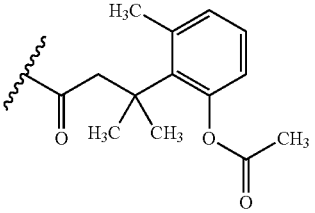 [SMILES: *C(=O)CC(C)(C)c1c(C)cccc1OC(C)=O] |

TABLE 3-continued
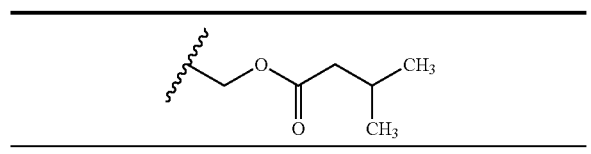
| Cmpd | X |
|---|---|
| 388 | 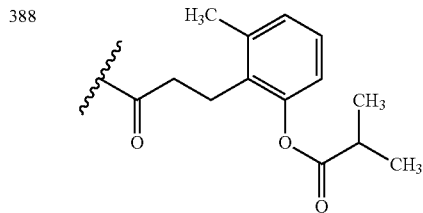 |
| 389 | 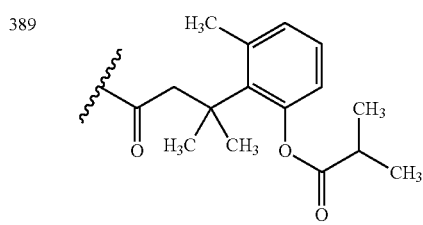 |
| 390 | 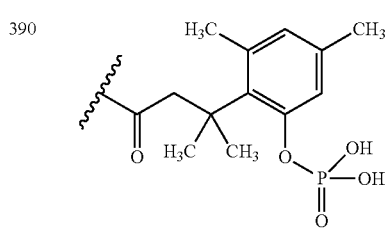 |
| 391 | 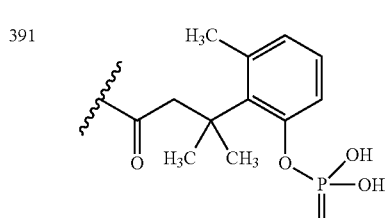 |
| 392 | 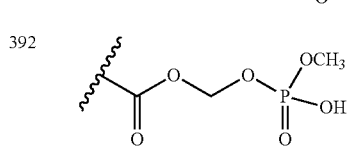 |
| 393 | 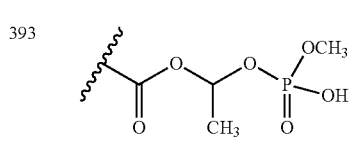 |
| 394 | 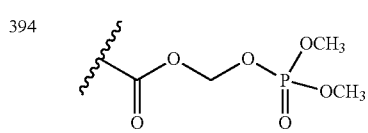 |
| 395 | 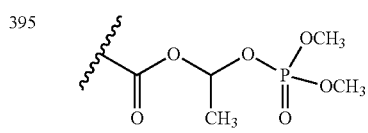 |
TABLE 3-continued
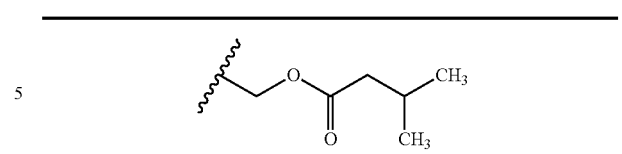
| Cmpd | X |
|---|---|
| 396 | 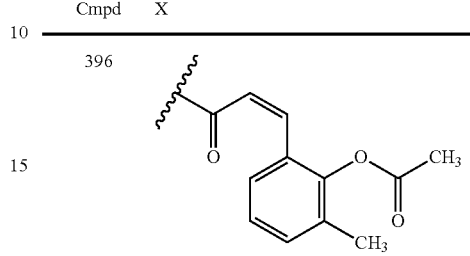 |
| 397 | 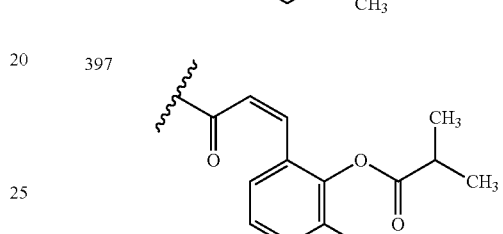 |
| 398 | 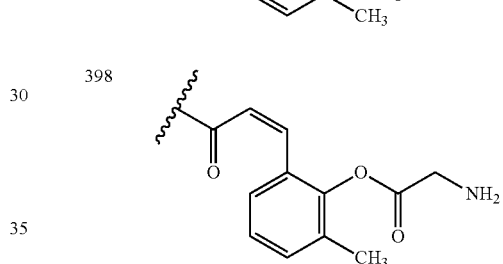 |
| 399 | 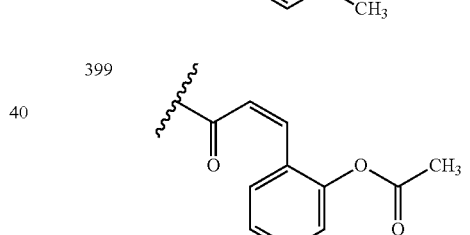 |
| 400 | 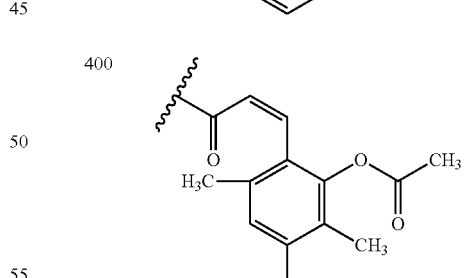 |
| 401 | 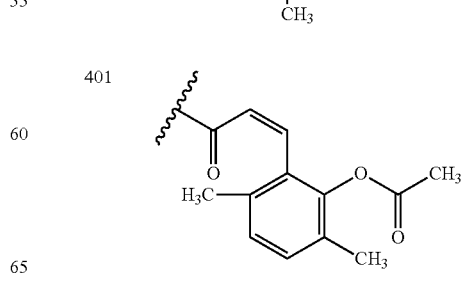 |

TABLE 3-continued
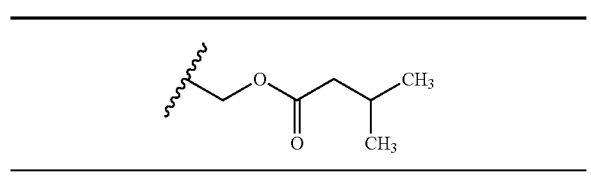
| Cmpd | X |
|---|---|
| 402 | 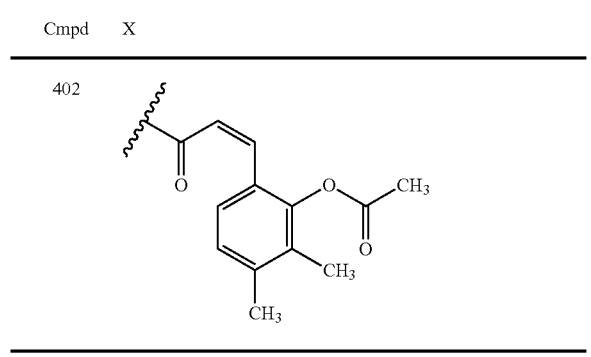 |
TABLE 4
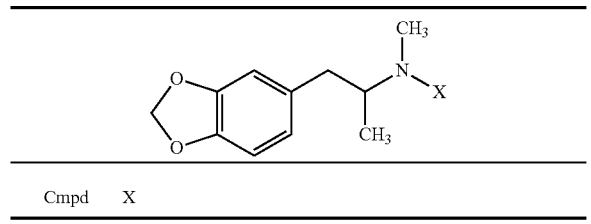
| Cmpd | X |
|---|---|
| 403 | |
| 404 | |
| 405 | |
| 406 | |
| 407 | |
| 408 | |
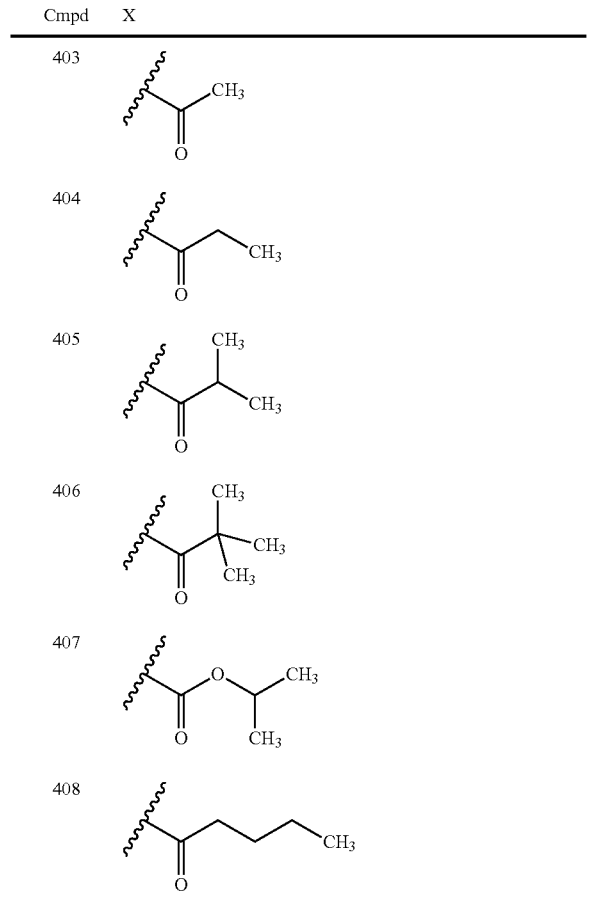
TABLE 4-continued
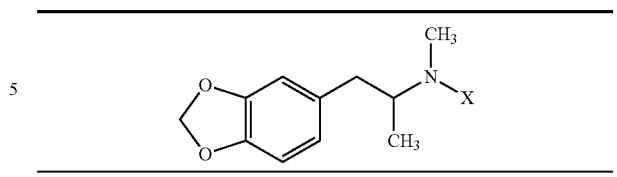
| Cmpd | X |
|---|---|
| 409 | |
| 410 | |
| 411 | |
| 412 | |
| 413 | |
| 414 | |
| 415 | |
| 416 | |
| 417 | |
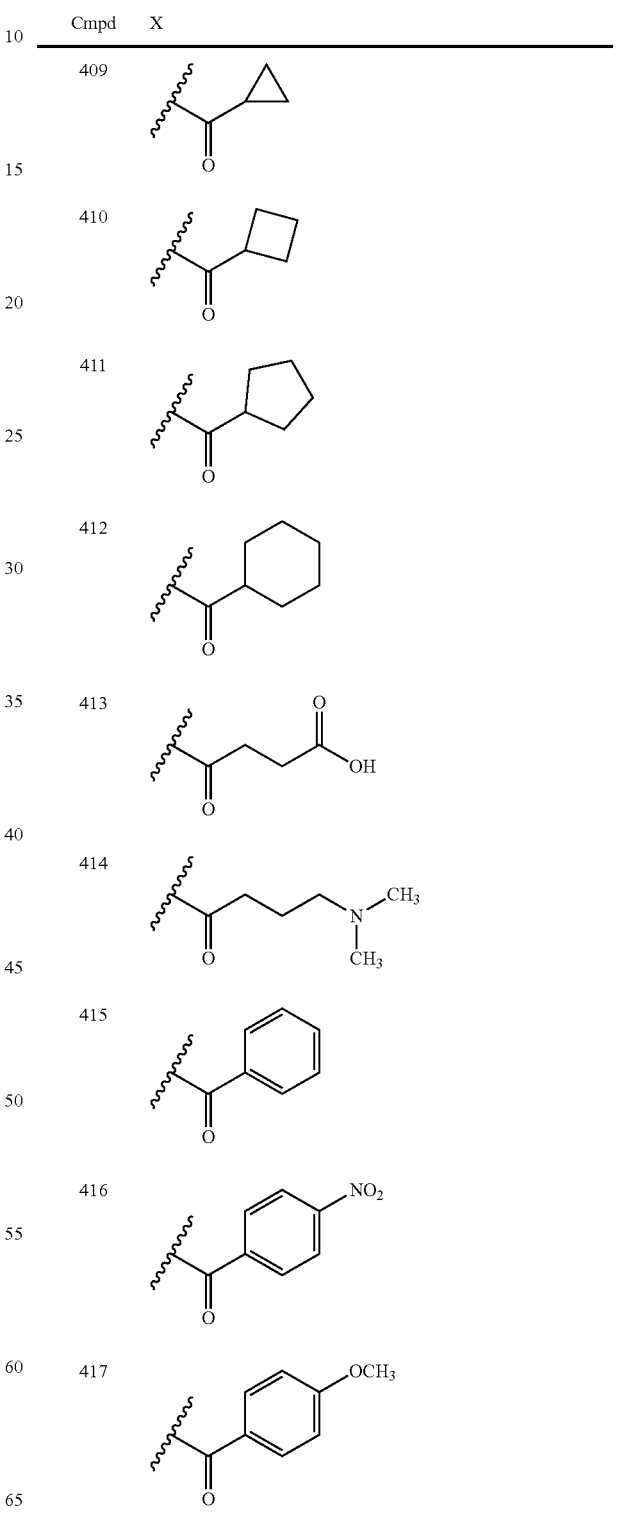

TABLE 4-continued

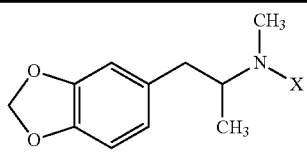

| Cmpd | X |
|---|---|
| 418 | 2-pyridyl-C(O)- |
| 419 | 3-pyridyl-C(O)- |
| 420 | 4-pyridyl-C(O)- |
| 421 | 1H-imidazol-2-yl-C(O)- |
| 422 | CCl₃-C(O)- |
| 423 | CF₃-C(O)- |
| 424 | -C(O)-O-CH₂-O-P(O)(OH)₂ |
| 425 | -C(O)-O-CH(CH₃)-O-P(O)(OH)₂ |
| 426 | -C(O)-O-CH(CH₃)-O-C(O)-CH₃ |
| 427 | -C(O)-O-CH(CH₃)-O-C(O)-CH₂CH₃ |

TABLE 4-continued

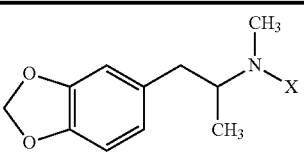

| Cmpd | X |
|---|---|
| 428 | -C(O)-O-CH(CH₃)-O-C(O)-CH(CH₃)₂ |
| 429 | -C(O)-O-CH(CH₃)-O-C(O)-C(CH₃)₃ |
| 430 | -C(O)-O-CH(CH₃)-O-C(O)-CH₂CH₂CH₂CH₃ |
| 431 | -C(O)-O-CH(CH₃)-O-C(O)-cyclopropyl |
| 432 | -C(O)-O-CH₂-O-C(O)-CH₃ |
| 433 | -C(O)-O-CH₂-O-C(O)-CH₂CH₃ |
| 434 | -C(O)-O-CH₂-O-C(O)-CH(CH₃)₂ |
| 435 | -C(O)-O-CH₂-O-C(O)-C(CH₃)₃ |
| 436 | -C(O)-O-CH₂-O-C(O)-CH₂CH₂CH₂CH₃ |
| 437 | -C(O)-O-CH₂-O-C(O)-cyclopropyl |

TABLE 4-continued
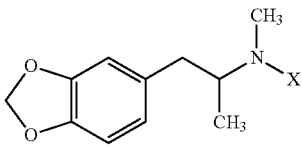
| Cmpd | X |
|---|---|
| 438 | 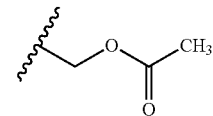 [SMILES: *COC(C)=O] |
| 439 | 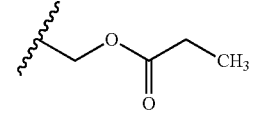 [SMILES: *COC(=O)CC] |
| 440 | 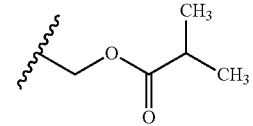 [SMILES: *COC(=O)C(C)C] |
| 441 | 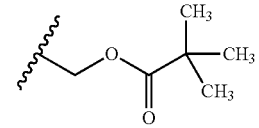 [SMILES: *COC(=O)C(C)(C)C] |
| 442 | 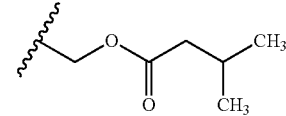 |
| 443 | 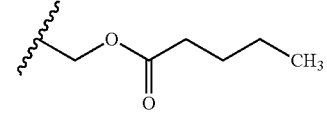 [SMILES: *COC(=O)CCCC] |
| 444 | 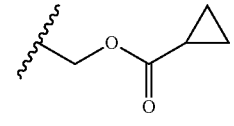 [SMILES: *COC(=O)C1CC1] |
| 445 | 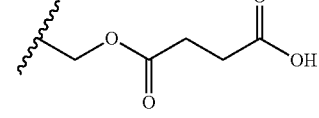 |
| 446 | 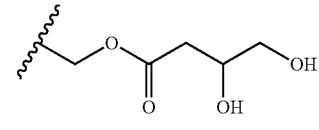 [SMILES: *COC(=O)CC(O)CO] |
| 447 | 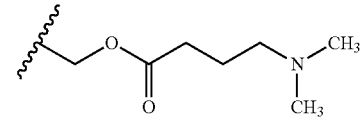 [SMILES: *COC(=O)CCCN(C)C] |
| 448 | $CH_2OPO(OH)_2$ |
TABLE 4-continued
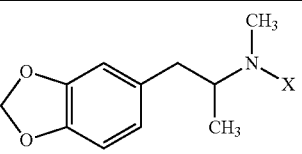
| Cmpd | X |
|---|---|
| 449 | 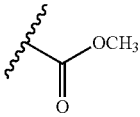 |
| 450 | 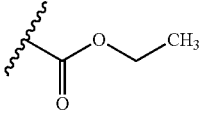 [SMILES: *C(=O)OCC] |
| 451 | 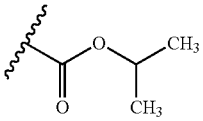 |
| 452 | 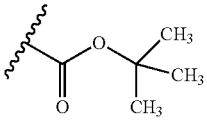 |
| 453 | 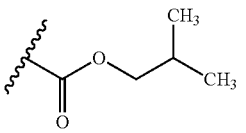 [SMILES: *C(=O)OCC(C)C] |
| 454 | 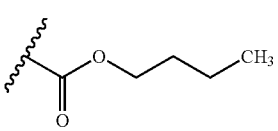 [SMILES: *C(=O)OCCCC] |
| 455 | 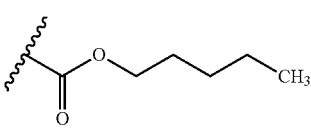 [SMILES: *C(=O)OCCCCC] |
| 456 | 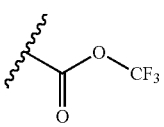 |
| 457 | 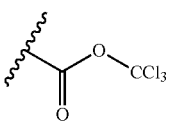 |
| 458 | 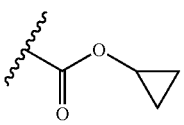 |

TABLE 4-continued
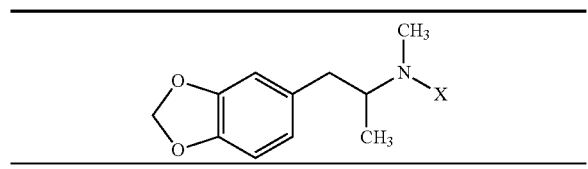
| Cmpd | X |
|---|---|
| 459 |  |
| 460 |  |
| 461 | 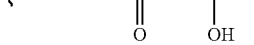 |
| 462 |  |
| 463 |  |
| 464 |  |
| 465 |  |
| 466 |  |
| 467 |  |
| 468 |  |
TABLE 4-continued
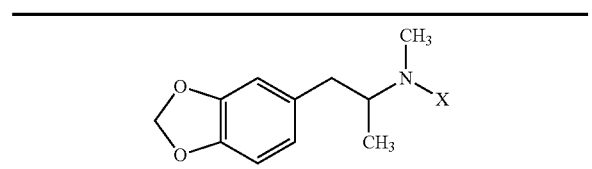
| Cmpd | X |
|---|---|
| 469 | 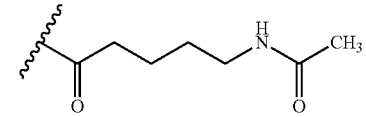 [SMILES: *C(=O)CCCCNC(C)=O] |
| 470 | 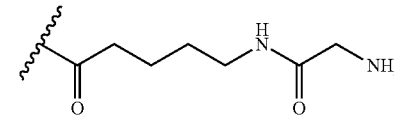 |
| 471 | 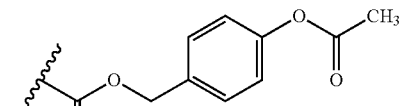 |
| 472 | 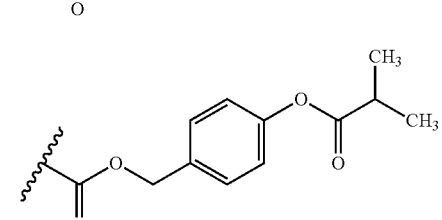 |
| 473 | 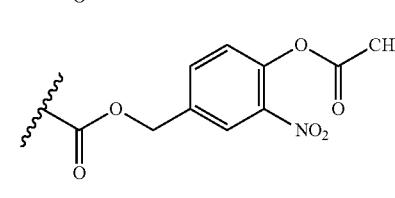 |
| 474 | 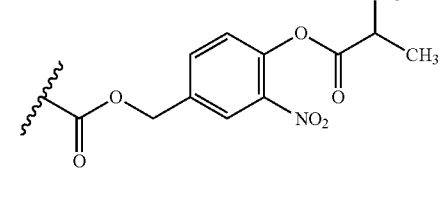 |
| 475 | 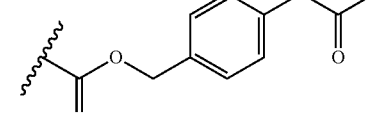 |
| 476 | 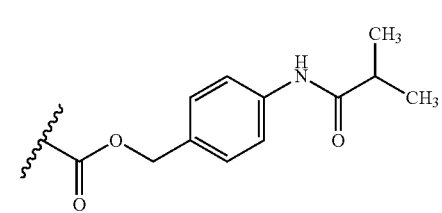 |

TABLE 4-continued

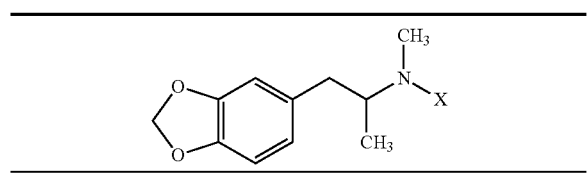

| Cmpd | X |
|---|---|
| 477 | 4-acetamido-3-nitrobenzyl ester |
| 478 | 4-isobutyramido-3-nitrobenzyl ester |
| 479 | 4-(2-aminoacetamido)-3-nitrobenzyl ester |
| 480 | 4-(phosphonooxy)benzyl ester |
| 481 | 2-acetoxybenzyl ester |
| 482 | 2-(isobutyryloxy)benzyl ester |
| 483 | 2-acetoxy-3-nitrobenzyl ester |

TABLE 4-continued

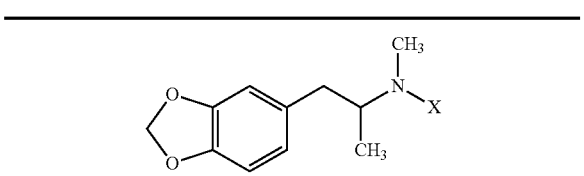

| Cmpd | X |
|---|---|
| 484 | 2-(isobutyryloxy)-3-nitrobenzyl ester |
| 485 | 2-acetamidobenzyl ester |
| 486 | 2-isobutyramidobenzyl ester |
| 487 | 2-acetamido-3-nitrobenzyl ester |
| 488 | 2-isobutyramido-3-nitrobenzyl ester |
| 489 | 2-(2-aminoacetamido)-3-nitrobenzyl ester |

TABLE 4-continued
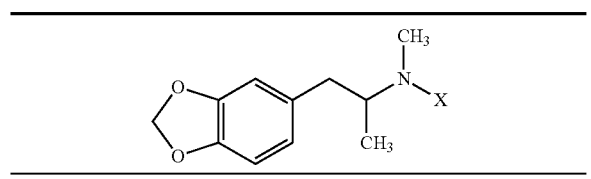
| Cmpd | X |
|---|---|
| 490 | 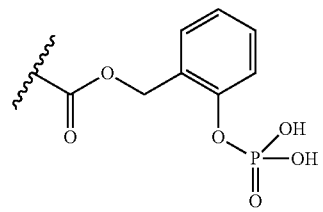 [SMILES: *C(=O)OCc1ccccc1OP(=O)(O)O] |
| 491 | 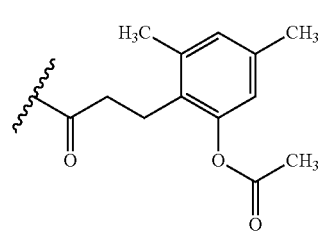 [SMILES: *C(=O)CCc1c(C)cc(C)cc1OC(C)=O] |
| 492 | 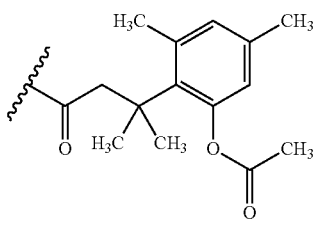 [SMILES: *C(=O)CC(C)(C)c1c(C)cc(C)cc1OC(C)=O] |
| 493 | 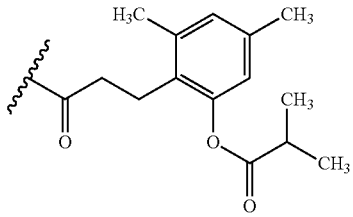 [SMILES: *C(=O)CCc1c(C)cc(C)cc1OC(=O)C(C)C] |
| 494 | 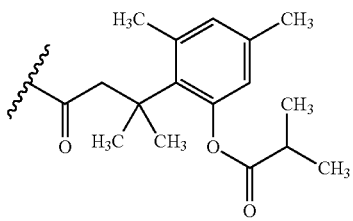 [SMILES: *C(=O)CC(C)(C)c1c(C)cc(C)cc1OC(=O)C(C)C] |
| 495 | 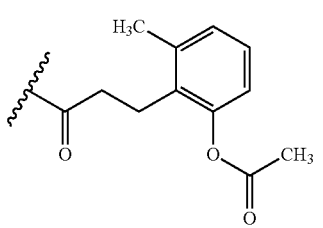 [SMILES: *C(=O)CCc1c(C)cccc1OC(C)=O] |
TABLE 4-continued
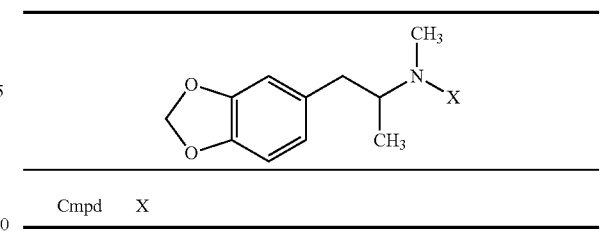
| Cmpd | X |
|---|---|
| 496 | 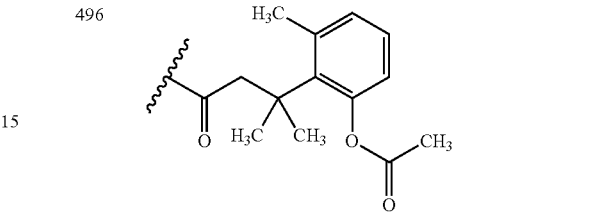 |
| 497 | 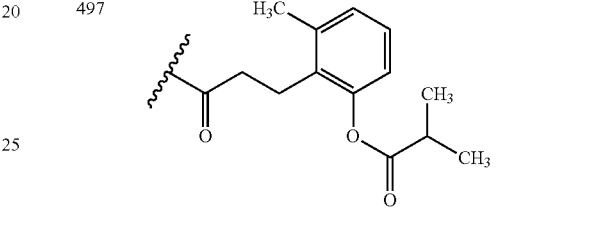 |
| 498 | 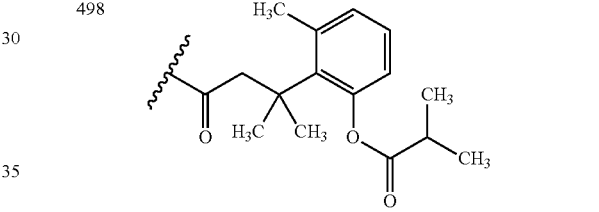 |
| 499 | 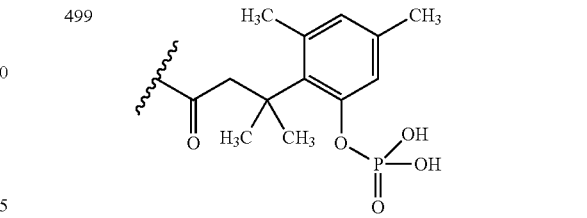 |
| 500 | 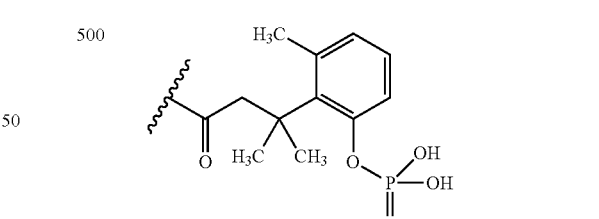 |
| 501 | 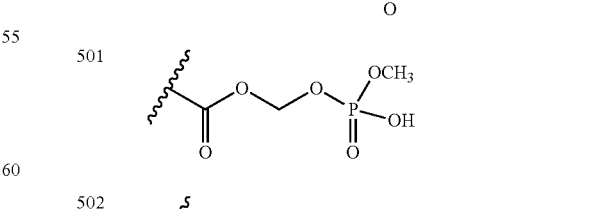 |
| 502 | 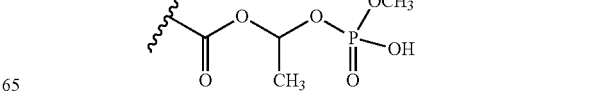 |

TABLE 4-continued

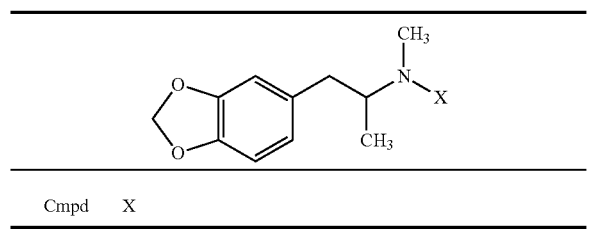

| Cmpd | X |
|---|---|
| 503 | 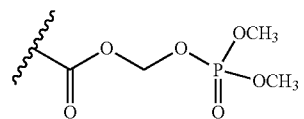 [SMILES: *C(=O)OCOP(=O)(OC)OC] |
| 504 | 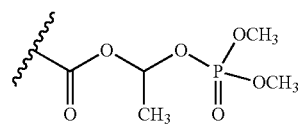 [SMILES: *C(=O)OC(C)OP(=O)(OC)OC] |
| 505 | 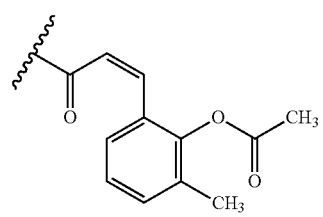 [SMILES: *C(=O)/C=C\c1cccc(C)c1OC(C)=O] |
| 506 | 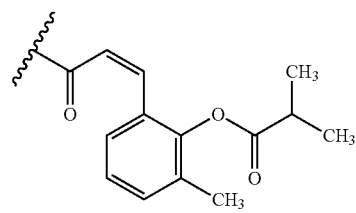 [SMILES: *C(=O)/C=C\c1cccc(C)c1OC(=O)C(C)C] |
| 507 | 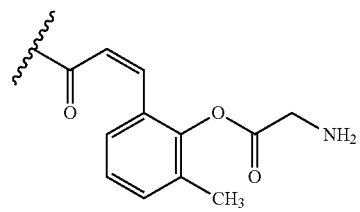 [SMILES: *C(=O)/C=C\c1cccc(C)c1OC(=O)CN] |
| 508 | 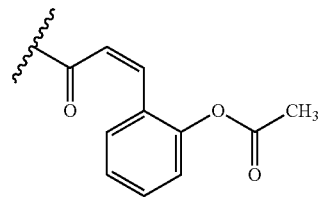 [SMILES: *C(=O)/C=C\c1ccccc1OC(C)=O] |
| 509 | 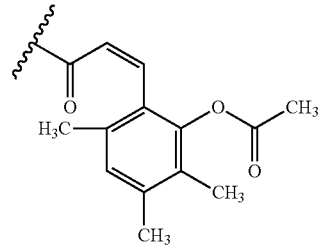 [SMILES: *C(=O)/C=C\c1c(C)cc(C)c(C)c1OC(C)=O] |

TABLE 4-continued

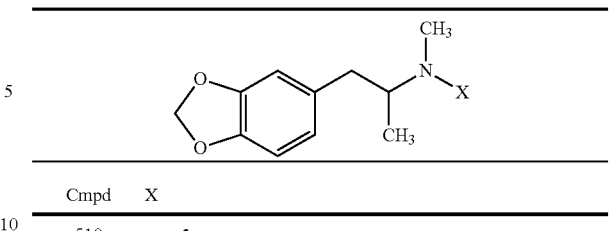

| Cmpd | X |
|---|---|
| 510 | 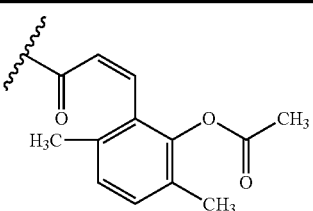 |
| 511 | 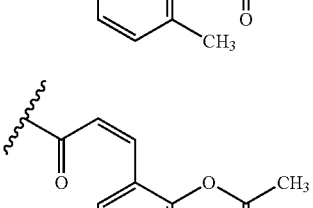 |

Compound 1: (2S)-2,6-diamino-N-(1-(benzo[d][1,3]dioxol-5-yl)-1-oxopropan-2-yl)-N-methylhexanamide

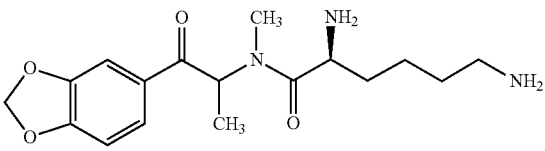 [SMILES: CC(C(=O)c1ccc2c(c1)OCO2)N(C)C(=O)[C@@H](N)CCCCN]

Compound 1 was prepared by the following procedure: Step 1: di-tert-butyl ((5S)-6-((1-(benzo[d][1,3]dioxol-5-yl)-1-oxopropan-2-yl)(methyl)amino)-6-oxohexane-1,5-diyl) dicarbamate. To a solution of methylone hydrochloride (1.03 g) in 100 mL of $CH_2Cl_2$ at room temperature was added diisopropylethylamine (3.6 mL), HOBT (0.87 g), di-Boc-Lysine (1.7 g), EDC (0.9 mL) and DMAP (0.1 g). The reaction was stirred overnight at room temperature followed by the addition of 100 mL of $CH_2Cl_2$. The resulting solution was washed with 200 mL of 1 M HCl, 200 mL of aqueous saturated $NaHCO_3$ and 200 mL of aqueous saturated NaCl. The organic layer was dried over sodium sulfate, concentrated under reduced pressure, and purified by silica gel column chromatography using 30-50% EtOAc in hexane. The pure fractions were then combined and concentrated to afford the desired Boc protected intermediate as an off-white solid.

Step 2: (2S)-2,6-diamino-N-(1-(benzo[d][1,3]dioxol-5-yl)-1-oxopropan-2-yl)-N-methylhexanamide. To a $CH_2Cl_2$ (10 mL) solution of di-tert-butyl ((5S)-6-((1-(benzo[d][1,3]dioxol-5-yl)-1-oxopropan-2-yl)(methyl)amino)-6-oxohexane-1,5-diyl)dicarbamate from step 1, was added 10 mL of trifluoroacetic acid. The reaction was stirred 4 hours at room temperature, diluted with 10 mL of $CH_2Cl_2$ and brought to pH 1 with 20 mL of 1 M HCl. Layers were separated and 20% NaOH$_{aq}$· was added to the aqueous layer to bring the pH>10. This resulting basic aqueous layer was extracted twice with 20 mL of CH$_2$Cl$_2$. The combined organic layers were concentrated under reduced pressure to afford compound 1 as a solid.

Compound 2: 2-amino-N-(1-(benzo[d][1,3]dioxol-5-yl)-1-oxopropan-2-yl)-N-methylacetamide

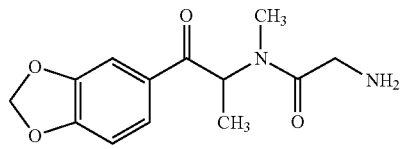 [SMILES: CC(C(=O)c1ccc2c(c1)OCO2)N(C)C(=O)CN]

Compound 2 was prepared by the following procedure: Step 1: tert-butyl (2-((1-(benzo[d][1,3]dioxol-5-yl)-1-oxopropan-2-yl)(methyl)amino)-2-oxoethyl)carbamate. To a solution of methylone hydrochloride (0.5 g) in 50 mL of CH$_2$Cl$_2$ at room temperature was added diisopropylethylamine (1.8 mL), Boc-Glycine (0.47 g), EDC (0.5 mL), DMAP (0.1 g) and HOBT (0.42 g). The reaction was stirred overnight at room temperature followed by the addition of 50 mL of CH$_2$Cl$_2$. The resulting solution was washed with 100 mL of 1 M HCl, 100 mL of aqueous saturated NaHCO$_3$ and 100 mL of aqueous saturated NaCl. The organic layer was concentrated under reduced pressure to afford an off-white solid. This crude product was carried to the next step without purification.

Step 2: 2-amino-N-(1-(benzo[d][1,3]dioxol-5-yl)-1-oxopropan-2-yl)-N-methylacetamide. To a CH$_2$Cl$_2$ (10 mL) solution of tert-butyl (2-((1-(benzo[d][1,3]dioxol-5-yl)-1-oxopropan-2-yl)(methyl)amino)-2-oxoethyl)carbamate from step 1, was added 10 mL of trifluoroacetic acid. The reaction was stirred 4 hours at room temperature, diluted with 30 mL of CH$_2$Cl$_2$ and brought to pH 1 with 20 mL of 1 M HCl. Layers were separated and 20% NaOH$_{aq}$· was added to the aqueous layer to bring the pH>10. This resulting basic aqueous layer was extracted twice with 20 mL of CH$_2$Cl$_2$. The combined organic layers were concentrated under reduced pressure to afford compound 2 as a solid.

Compound 25: N-(1-(benzo[d][1,3]dioxol-5-yl)-1-oxopropan-2-yl)-N-methylacetamide

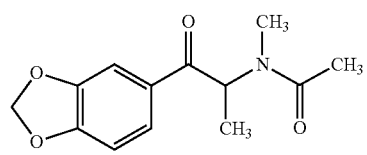 [SMILES: CC(=O)N(C)C(C)C(=O)c1ccc2c(c1)OCO2]

Compound 25 was prepared by the following procedure: To a solution of methylone hydrochloride (0.5 g) in 50 mL of CH$_2$Cl$_2$ was added diisopropylethylamine (0.9 mL). The solution was stirred 15 minutes at room temperature, cooled down to 0° C. and acetyl chloride (0.3 mL) was added. After 30 minutes at 0° C., the reaction was allowed to warm up to room temperature and stirred overnight. Volatiles were then removed under reduced pressure to afford a yellow solide that was dissolved in 150 mL of CH$_2$Cl$_2$. The resulting solution was washed twice with 100 mL aqueous saturated NaHCO$_3$ and 100 mL of aqueous saturated NaCl. The organic layer was concentrated under reduced pressure to yield compound 25 as a solid.

Compound 45: N-(1-(benzo[d][1,3]dioxol-5-yl)-1-oxopropan-2-yl)-2,2,2-trifluoro-N-methylacetamide

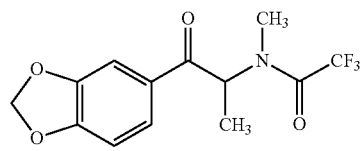 [SMILES: CC(C(=O)c1ccc2c(c1)OCO2)N(C)C(=O)C(F)(F)F]

Compound 45 was prepared by the following procedure: to a 25 mL round-bottomed flask under nitrogen was charged methylone hydrochloride (500 mg, 2.05 mmol, 1.0 eq) and DCM (4 mL, 8 vol) with DIPEA (1.09 mL, 6.25 mmol, 3 eq). After stirring for 10 mins a light brown solution formed. The solution was cooled to 0° C. and trifluoroacetic anhydride (483 mg, 2.3 mmol, 1.12 eq) in DCM (1 mL, 2 vol) was charged dropwise, off gassing and a small exotherm from 4° C. to 10° C. was observed. After 30 mins of stirring at 0° C. to 10° C., HPLC monitoring indicated 66% product and 33% starting material. An additional charge of DIPEA (0.44 mL, 1.23 mmol eq) and trifluoroacetic anhydride (237 mg, 0.55 eq) was made, and the reaction stirred overnight at ambient temperature. HPLC analysis the following day showed 95% product and no detectable starting material. The reaction was washed with water (5 mL×2), the DCM layer was dried (MgSO4) and concentrated to afford an orange solid. The solid was purified by column chromatography (10 g silica, 100% DCM) to give 372 mg of compound 45 as a solid.

Compound 50: 1-(((1-(benzo[d][1,3]dioxol-5-yl)-1-oxopropan-2-yl)(methyl)carbamoyl)oxy)ethyl isobutyrate

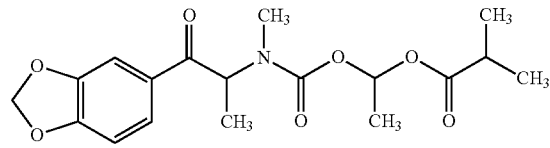 [SMILES: CC(OC(=O)C(C)C)OC(=O)N(C)C(C)C(=O)c1ccc2c(c1)OCO2]

Compound 50 was prepared by the following procedure: To a 0° C. suspension of methylone hydrochloride (1.35 g) in CH$_2$Cl$_2$ (10 mL) was added triethylamine (1.19 g in 2 mL of CH$_2$Cl$_2$). The resulting beige solution was stirred at 0° C. for 10 minute followed by the dropwise addition of 1-(((4-Nitrophenoxy)carbonyl)oxy)ethyl isobutyrate (2.0 g in 4 mL of CH$_2$Cl$_2$) over 5 minutes. The reaction mixture was stirred between −5 to 5° C. for 1 h then warmed up to RT (15-20° C.) and stirred over the weekend (~66 h) and an orange solution was obtained. 1M aqueous acetic acid (7 mL) was then added dropwise over 5 minutes below 25° C. and stirred for 5 minutes. The phases were separated and the organic layer was washed with 1M aqueous K$_2$CO$_3$ (3×7 mL) and then 20% aqueous brine (7 mL). The material was concentrated in vacuo at 30° C. then redissolved in ethyl acetate (10 mL). The organic was washed with 1M aqueous K$_2$CO$_3$ (2×7 mL) followed by 20% aqueous brine (7 mL) and then concentrated in vacuo at 40° C. The crude material was purified via silica gel column chromatography and eluted with 1-10% ethyl acetate in heptane. The clean fractions were concentrated in vacuo at 40° C. then stripped from TBME (3×20 mL) to afford compound 50.

Compound 71: methyl (1-(benzo[d][1,3]dioxol-5-yl)-1-oxopropan-2-yl)(methyl)carbamate

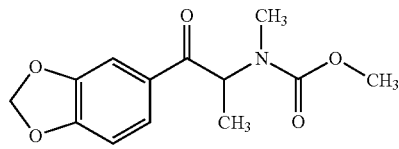 [SMILES: COC(=O)N(C)C(C)C(=O)c1ccc2c(c1)OCO2]

Compound 71 was prepared by the following procedure: to a 25 mL round-bottomed flask under nitrogen was charged methylone hydrochloride (500 mg, 2.05 mmol, 1.0 eq) with DCM (4 mL, 8 vol) and DIPEA (1.09, 6.25 mmol, 3 eq). The reaction was cooled to 0° C. and methyl chloroformate (257 mg, 2.7 mmol, 1.3 eq) in DCM (1 mL, 2 vol) was charged dropwise over 5 minutes to form a pale brown solution, an exotherm from 6° C. to 12° C. was observed. HPLC analysis showed the starting material had been consumed. The reaction was worked up by washing with water (5 mL×2) using a phase separator. The DCM concentrated to afford a clear oil. The oil was purified using column chromatography (10 g silica, 100% DCM) to afford 197 mg of compound 71 as a clear oil.

Compound 77: pentyl (1-(benzo[d][1,3]dioxol-5-yl)-1-oxopropan-2-yl)(methyl)carbamate

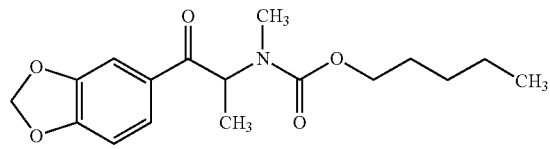 [SMILES: CCCCCOC(=O)N(C)C(C)C(=O)c1ccc2c(c1)OCO2]

Compound 77 was prepared by the following procedure: To a solution of methylone hydrochloride (0.5 g) in 50 mL of $CH_2Cl_2$ was added diisopropylethylamine (0.9 mL) and triethylamine (0.46 mL). The solution was stirred 15 minutes at room temperature, cooled down to 0° C. and amyl chloroformate (0.5 mL) was added dropwise. The reaction was allowed to warm up to room temperature and stirred for 90 minutes. Volatiles were removed under reduced pressure to afford an off-white solide that was then dissolved in 100 mL of $CH_2Cl_2$. The resulting solution was washed twice with 100 mL aqueous saturated $NaHCO_3$ and 100 mL of aqueous saturated NaCl. The organic layer was concentrated under reduced pressure to afford compound 77 as a solid.

Example 2

Assessment of Prodrug Effects on the Pharmacokinetic Properties of Methylone

The pharmacokinetic properties of methylone after a single administration intravenously (IV), intraperitoneally (IP), or by oral gavage (PO) in male Sprague Dawley rats has been determined using a liquid chromatography tandem mass spectrometry (LC-MS/MS) method that has been established and validated for methylone in the rat. Rats (n=3 per group) received a single dose of methylone: 5 mg/kg IV, 15 mg/kg IP, or 15 mg/kg PO. Plasma was sampled at time points between 0.083-24 hours, methylone levels determined, and key parameters (e.g., $C_{max}$, $T_{max}$, $T_{1/2}$, and AUC) were analyzed from the data. Results are shown in Table 5.

TABLE 5

Selected pharmacokinetic parameters of methylone following a single IV, PO and IP administration to male Sprague-Dawley rats

| PK Parameters | Methylone | | |
|---|---|---|---|
| | Group 1 (IV) | Group 2 (PO) | Group 3 (IP) |
| $C_{max}$ (ng/mL) | N/A | 678 ± 243 | 4230 ± 514 |
| $T_{max}$ (h) | N/A | 1.33 ± 0.577 | 0.250 ± 0.000 |
| $T_{1/2}$ (h) | 0.362 ± 0.024 | 3.23 ± 1.99 | 0.800 ± 0.169 |
| $C_0$ (ng/mL) | 3018 ± 666 | N/A | N/A |
| $Vd_{ss}$ (L/kg) | 1.98 ± 0.230 | N/A | N/A |
| Cl (mL/min/kg) | 68.3 ± 5.40 | N/A | N/A |
| $AUC_{0-last}$ (ng · h/mL) | 1200 ± 88.2 | 2765 ± 657 | 4305 ± 1179 |
| $MRT_{0-last}$ (h) | 0.439 ± 0.026 | 2.99 ± 0.467 | 1.07 ± 0.211 |

To investigate whether the prodrug extends the half-life or alters other basic pharmacokinetic properties of methylone (e.g., $C_{max}$ or $T_{max}$), rats are treated with each prodrug IV, IP, or PO. For each compound, three groups of rats are treated as follows: For group 1, a single dose of methylone is administered to 3 male Sprague-Dawley rats by IV bolus at 5 mg/kg. For group 2, a single dose of methylone is administered to 3 male Sprague-Dawley rats by oral gavage (PO) at 15 mg/kg. For group 3, a single dose of methylone is administered to 3 male Sprague-Dawley rats by IP at 15 mg/kg. For all groups, blood samples are collected from each animal at 0.083, 0.25, 0.5, 1, 2, 4, 8, 12, and 24 hours post-dose for the determination of plasma concentrations. The plasma concentrations are quantified by liquid chromatography tandem mass spectrometry (LC-MS/MS). The bioanalytical assay has been established and validated, providing a lower limit of quantification (LLOQ) of 1 ng/mL and an upper limit of quantification (ULOQ) of 3000 ng/mL for methylone. The plasma concentration-time data are analyzed using Phoenix WinNonlin (version 8.3) to characterize the PK properties of the analyte. The non-compartmental analysis model and the linear/log trapezoidal method are applied to the calculation of the PK parameters.

Behavioral Pharmacology Studies to Address Efficacy of the Prodrugs

Antidepressant Efficacy in the Forced Swim Test (FST)

The forced swim test (FST) is a classic model to assess the antidepressant-like activity of compounds that has been in use for over 40 years (Porsolt et al. (1977) Nature 266:730-732; Detke et al. (1995) Psychopharmacology 121:66-72). All classes of antidepressants, including selective serotonin reuptake inhibitors, noradrenergic reuptake inhibitors, tricyclics, and more recent rapidly acting antidepressants like ketamine, psilocybin, or MDMA have all been shown to reduce immobility in the FST. Methylone has a robust, dose-dependent antidepressant-like effect in the rat forced swim test (FST). A single dose of 5 mg/kg methylone reduces immobility by approximately 50% compared to vehicle-treated controls, whereas a 15 mg/kg dose reduces immobility by nearly 100%. Accompanying changes in climbing and/or swimming behavior reflect noradrenergic and serotonergic activities of methylone, respectively.

All FST studies are performed and scored by an experimenter blind to treatment group and according to standard protocols. Briefly, rats are placed in a circular plexiglass container filled with water. Water temperature is maintained at 22-25° C. and changed for every animal. Day 1 (Training) consists of a 15 min acclimation trial, and Day 2 (Testing, 24 h later) consists of the 5 min test. A time sampling procedure is employed where animals are observed every 5 seconds for the duration of the test session (60 counts or 5 minutes) and scored for immobility (defined as the failure to struggle), swimming (defined as a circular movement around the tank), or climbing (defined as an upwards escape behavior). Data are expressed as the percent of the testing session (e.g., the number of immobility counts divided by 60). A p-value less than 0.05 indicates statistical significance after typical statistical analyses (e.g., unpaired t-test or ANOVA).

To determine the prodrug has an antidepressant-like effect and to compare it to methylone, rats are treated with each compound 30 min prior to testing. Additional tests are run 24, 72, 168 hours post-dose or longer.

Effects on Fear Extinction in a Model of Post-Traumatic Stress Disorder (PTSD)

Methylone (30 mg/kg, IP) significantly improves fear extinction recall in a mouse model of PTSD (FIG. 1). Deficient fear extinction memory is a feature of PTSD in patients (Wicking et al. (2016) *Neurobiology of Learning and Memory* 136:116). SSRI antidepressants, similar to the two approved for the treatment of PTSD (i.e., paroxetine and sertraline), prevent fear memory generalization and enhance extinction (Pedraza et al. (2019) *Transl Psychiatry* 9:53). The enhancement of fear extinction might also underlie the beneficial effect of MDMA as a PTSD treatment (Feduccia & Mithoefer (2018) *Progress in Neuro-Psychopharmacology & Biological Psychiatry* 84(Part A), 221-228).

Effective PTSD treatments facilitate the disassociation between a traumatic memory and the patient's fear response, making cues for the traumatic memory evoke less of a fear response. This is modeled in the mouse fear extinction paradigm which takes place over 3 days. On day 1 (fear conditioning), mice are trained to acquire a "traumatic memory," namely associating the conditioned stimulus (CS, tone) to the unconditioned stimulus (US, foot shock). On day 2 (extinction training), they are trained to forget the traumatic memory association by presenting the CS 6 times (with no US) in a novel environment. On day 3 (extinction recall), the mice are "asked" if that tone (CS) still elicits a fearful response, as measured by the time spent freezing when the tone is presented. Less time freezing means better extinction recall. Drugs that improve extinction recall reduce freezing time on day 3, and, therefore, show potential as a PTSD treatment.

Figure 1B:
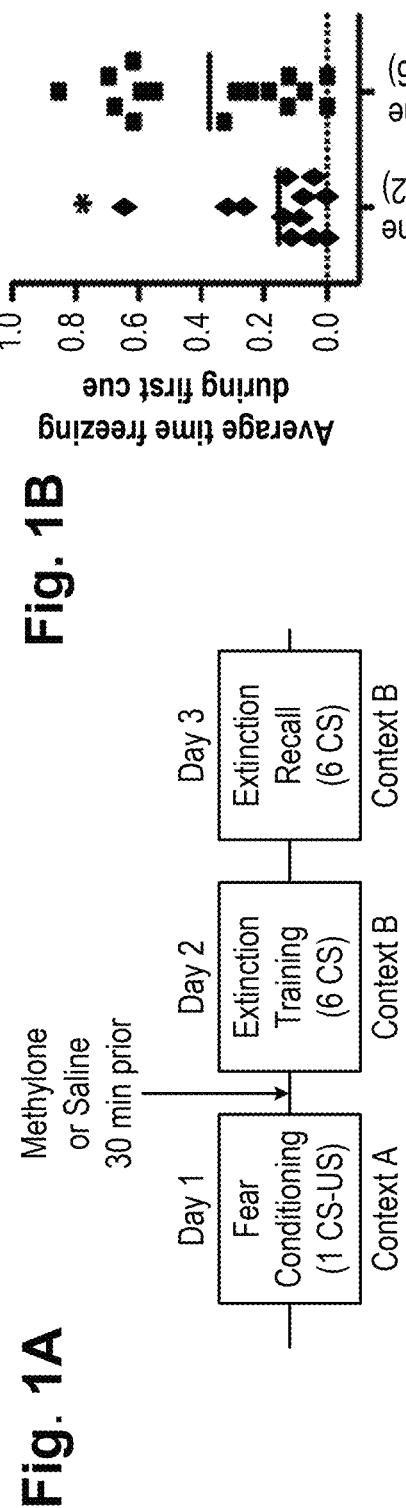
Figure 1C:
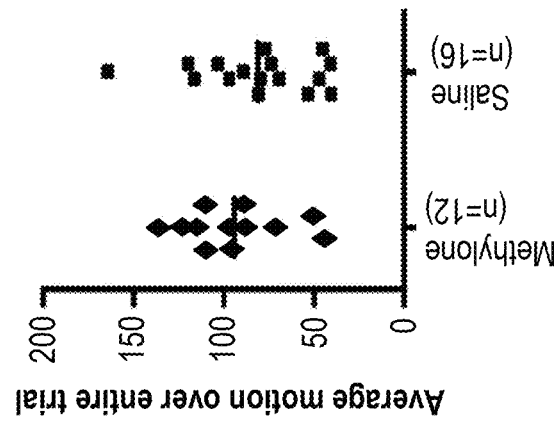
Figure 1D:
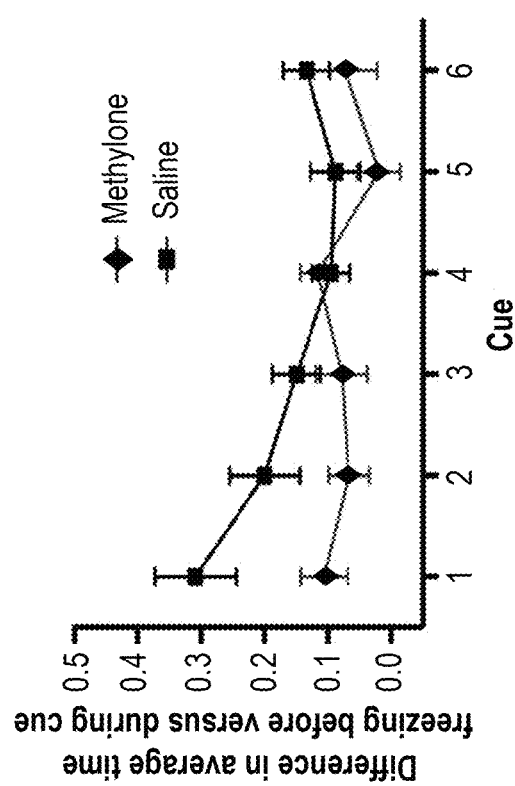

Work with MDMA shows that after fear conditioning, administering MDMA (7.5 mg/kg) 30 minutes prior to extinction training enhances extinction recall measured as 35% reduced freezing compared to saline injected controls (Young et al. (2015) *Transl Psychiatry* 5:e634). Using a similar experimental design, recent results show that methylone (30 mg/kg) significantly enhances fear extinction recall (FIG. 1) by nearly 60% compared to saline controls (FIG. 1B). Using these methods, prodrugs are administered to mice and tested for efficacy in the fear extinction model to evaluate their efficacy to treat PTSD and other memory disorders.

Anxiolytic Effects in Other Behavioral Anxiety Models

Additional behavioral testing including the elevated plus maze (EPM) and thigmotaxis in the open field test (OFT) are used to assess the anxiolytic effects of methylone and its prodrugs in mice or rats. Methylone (5, 10, 20 mg/kg, SC) has been shown to reduce thigmotaxis (time spent hugging the perimeter of the open field) in rats (Stefkovi et al. (2017) *Front Psychiatry* 8:232), consistent with an anxiolytic effect. These models are described in greater detail below. Prodrugs are screened in these behaviors to the anxiolytic efficacy of each compound.

Methylone reduces time spent in the center vs the periphery in the OFT, consistent with an anxiolytic-like response. Methylone is also a stimulant that increases locomotor activity in this test. Prodrug compounds are screened for their effects on both parameters. Briefly, rodents are assessed in a 30 minute OFT using an automated activity monitoring system. Rodents are acclimated to the room 30 minutes before the start of testing. The following parameters are captured: Horizontal distance travelled, overall ambulatory time, and ambulatory counts. Vertical activity (time and counts), Time in the Center vs. Periphery data are reported in 5 minute bins as well as total time.

The EPM is a classic anxiety model that also capitalizes on a rodent's dislike for open spaces. The effects of prodrug compounds and methylone are tested in this model. Briefly, rodents are acclimated to the anteroom at least 30 minutes before the start of the experiment. Testing is performed in dim light (40 lux). The elevated plus maze consists of two open and two closed arms (arm length: 30 cm; width: 5 cm). Open arms have a small 1 cm edge and the closed arms are bordered by a 15 cm wall. At the beginning of the task, rodents are placed in the center of the elevated plus maze facing an open arm and are videotracked while exploring the maze for 5 minutes. The time spent in the open and closed arms are measured and analyzed. More time in the open arm vs. the closed arm is consistent with an anxiolytic effect.

Example 3

Assessment of Prodrug Effects on the Pharmacokinetic Properties of Methylone

Methylone is in clinical development for PTSD, supported by robust data from animals and humans demonstrating its safety and potential for clinical benefit. However, generation of a methylone prodrug would have distinct advantages, addressing methylone's short half-life and dose-dependent increases in heart rate and blood pressure. The current clinical protocol for methylone employs a supervised, split dosing session (i.e., two subeffective doses given ~1 hour apart), frequent blood pressure and heart rate monitoring for 6-8 hours post-dose, and the exclusion of patients with a history of cardiovascular conditions. Improving the PK properties of methylone (e.g., lower $C_{max}$, longer half-life) with a prodrug could reduce or eliminate the need for frequent blood pressure and heart rate monitoring and potentially expand the eligibility criteria, making methylone's clinical benefit accessible to more patients.

Methylone prodrug analogs have been synthesized. Exemplified below (Scheme 18) is the synthesis of compound 50. This acyloxyalkoxycarbonyl prodrug was efficiently prepared through a one-step process by the direct N-acylation of methylone with 1-4-nitrophenoxycarbonyoxyethyl 2-methyl propanoate, By modifying the nature of the ester residue, the rate of prodrug bioactivation from esterase's hydrolysis can be modulated. Therefore, an alternate approach is also proposed according to US2010/0160666, which is hereby incorporated by reference. This strategy would allow the rapid assemblage of a series of different ester analogs from one common intermediate.

Scheme 18

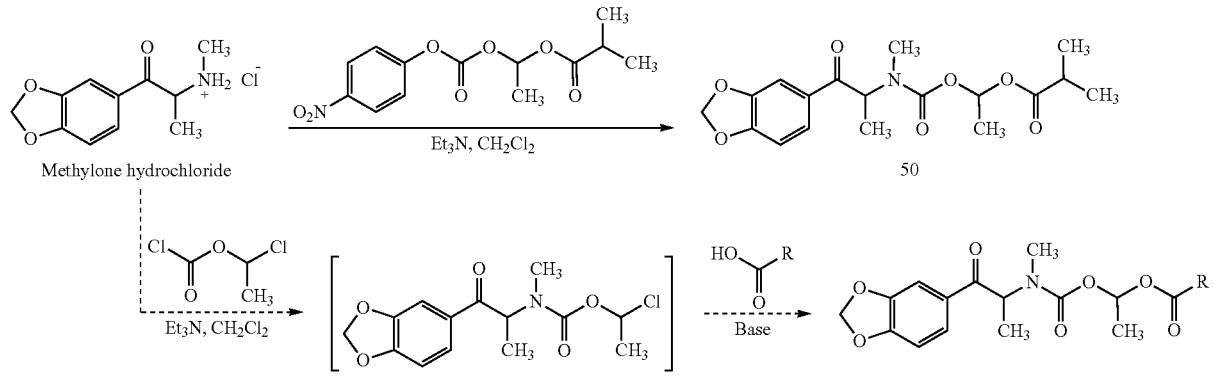

Designing, Synthesizing, and Characterizing Methylone Prodrugs:

Methylone is being developed as a treatment for PTSD based on its rapid-acting, robust and long-lasting beneficial effects in animals and humans. Overall, methylone is well-tolerated. Nonetheless, certain aspects of methylone's pharmacological profile warrant improvement. Development of an alternative therapeutic that showed the same overall safety and impressive beneficial effects of methylone, but with a longer duration of action (to extend therapeutic window) and lower $C_{max}$ (to minimize the cardiovascular effects) would be a significant advantage over parent methylone and have the potential for even greater impact in PTSD and other patients.

Methylone can be covalently bound to different promoieties by direct derivatization of its amino group. Prodrug bioactivation is determined initially by investigating chemical, hepatic, and whole blood stability in vitro in rat and human matrices. Based on their rate of in vitro cleavage to release the methylone active agent, prodrugs are selected and further characterized via rat PK for in vivo validation of the bioactivation process. A complete DMPK profile is then generated across 4 model species (mouse, rat, dog, NHP) and humans. Finally, the collected data are used to perform human PK prediction.

Prodrug Synthesis: The methylone prodrugs are synthesized by direct functionalization of the methylone's amino group as shown in Scheme 19. This approach affords seven different class of prodrugs as defined by the newly created functional group: amide (I), peptide (II), carbamate (III), acyloxyalkoxycarbonyl (IV), phosphoramide (V), acyloxymethyl (VI), and phosphoryloxymethyl (VII).

Even though the enzymatic biotransformation of each of these functional groups is clinically validated, it involves primary amines or less hindered N-substituted system compared to the methylone's secondary amine. Steric hindrance is known to significantly impact the rate of hydrolysis of peptide bonds. For some of methylone's prodrug such as class I, II or III, this could potentially inhibit the bioactivation process. Thus, prodrugs are also investigated that have a more "remote" site of activation, such as acyloxyalkoxycarbonyl IV, which are less dependent of the structural features of the parent molecule.

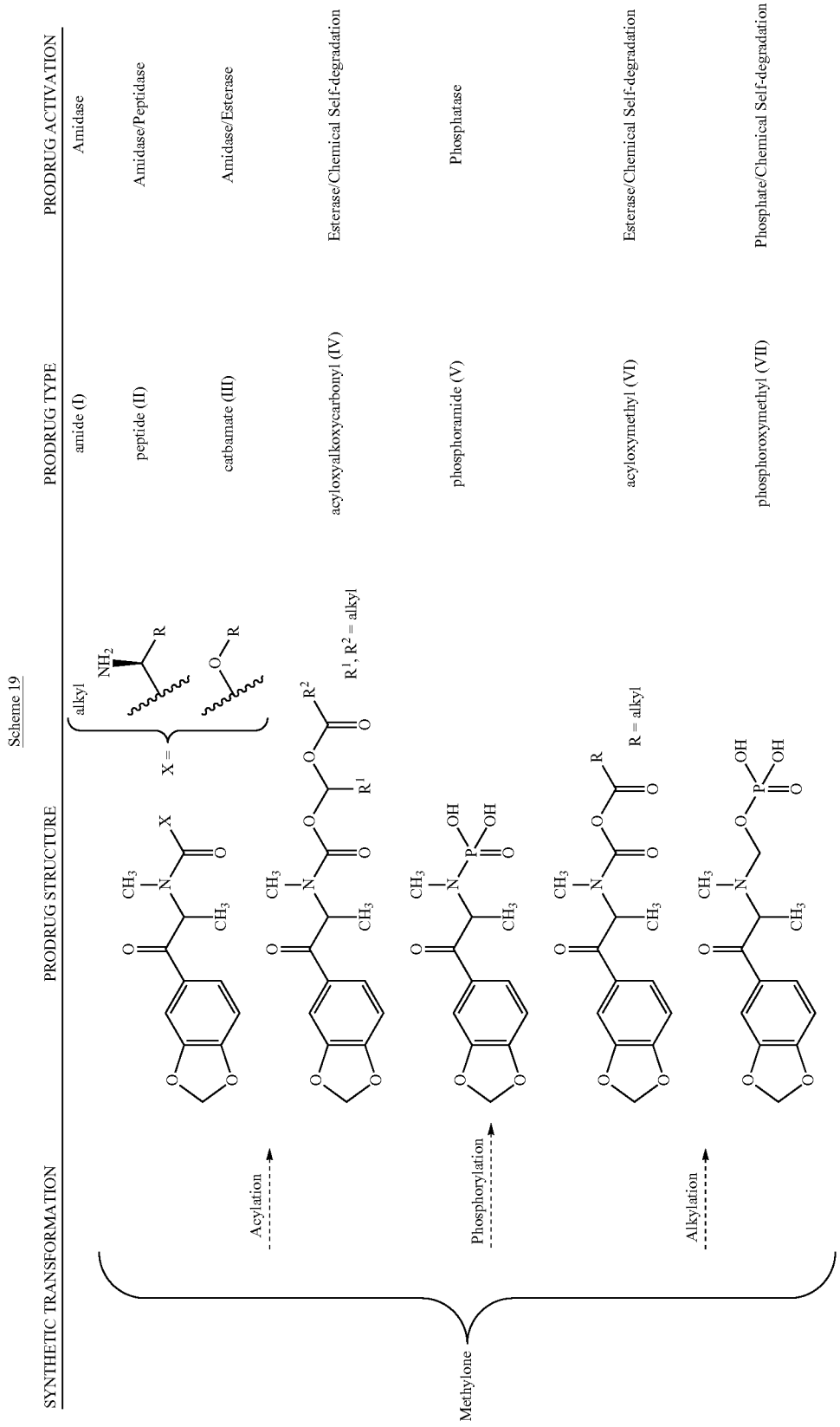

Bioactivation Potential of Prodrug Candidates: After a prodrug is synthesized, its bioactivation potential to release methylone is assessed under in vitro conditions. As the prodrugs are designed to be enzymatically activated by esterases and amidases/peptidases found in the blood and/or the liver, each prodrug is incubated in human and rat whole blood as well as liver hepatocytes. In these assays, the percentage of released parent methylone and of remaining prodrug is measured at different timepoints for a period of 2 hours. A chemical stability assessment of each prodrug is also performed under various pH conditions to ensure that the methylone released is a result of enzymatic hydrolysis. Prodrugs that show in vitro bioactivation are then administered (IV/PO) to rats, and blood samples are collected to assess the pharmacokinetic profile of each prodrug.

For example, the metabolic stability of prodrug candidates to release methylone could be assessed in vitro according to the following protocol: cryopreserved human and rat hepatocytes are thawed in recovery media and diluted in plating media to a viable cell density of $1 \times 10^6$ cells/mL. Viability is determined by trypan blue exclusion. A 350 µL suspension of cells is added to individual strip tubes and pre-incubated for 10 minutes at 37° C., 5% $CO_2$. Following preincubation, 350 µL of prodrug and reference compounds (testosterone and ethoxycoumarin) are added in duplicate at a final concentration of 1 M to start the reaction. From the mix, aliquots of 100 µL are transferred to a 96-well plate for incubation. At selected timepoints (0, 10, 30, 60, 90, 120 minutes), the incubations are quenched with 200 µL of ice-cold acetonitrile (ACN) containing internal standard (1 µM glyburide and labetalol). A pre-quenched sample of methylone is prepared to calculate percent appearance of the active drug at different timepoints of prodrug incubations. Samples are then centrifuged, and supernatants are further diluted 1:1 with 25% acetonitrile in water. All samples, including analytical standards, are analyzed by LC-MS/MS to measure the concentration of methylone released and the concentration of the corresponding prodrug remaining. A set criterion of 100% recovery is targeted where the summation of the % of prodrug remaining and the % of methylone released should be 100% with an experimental error tolerance of ±20%.

When compound 50 was incubated with human hepatocytes under the conditions described above, at t=60 minutes, approximately 100% of the prodrug had been converted to methylone with a total recovery of approximately 100%. As a negative control, when compound 50 was incubated up to 2 hours in the absence of hepatocytes in a phosphate buffer pH 6.8 at 37° C., no parent methylone was released.

DMPK Profiling: Based on the rat PK data, prodrugs are then selected for a more extensive assessment of their DMPK profile. With the main objective of performing human PK prediction, a set of data, including PK parameters, whole blood stability, hepatocytes metabolic profile, microsomal clearance and plasma protein binding, are collected across 4 species (mouse, rat, dog and NHP) and for human (in vitro assays only). Comparing the human in vitro metabolic profile and the pre-clinical species DMPK data set allows human PK prediction.

Metabolic resistance to prodrug bioactivation: As mentioned above, the steric hinderance of the alpha-substituted secondary amine of methylone might slow down the rate of hydrolysis of amide-type prodrugs to such an extent that very little of the parent is being released from the system. Alternate prodrugs are designed to rely on a dual activation process such as the acyloxyalkoxycarbonyl (IV), the acyloxymethyl (VI) or the phosphoryloxymethyl (VII). In this case, while the first step of prodrug activation is still an enzymatic hydrolytic process, it does not involve the methylone's amino group. A remote functional group gets cleaved off followed by a chemical self-degradation completely independent of the methylone's amine structural features.

Discrepancy between the predicted human PK and the preclinical POC species (rat, mouse): As the hydrolytic activity of esterases and/or amidases differs significantly between the different species, a prodrug with a suitable predicted human PK may be identified that cannot be used in a pre-clinical model to assess the duration of action because of PK discrepancy. We may therefore have to advance a so-called POC molecule with a fit-for-purpose PK profile. This candidate would add up to the lead and back-up candidate.

Demonstrating the Efficacy and Improved Cardiovascular Safety Profile of Prodrugs in Pre-Clinical Models:

Whereas a longer half-life generally translates into an extended duration of action, the overall impact of this new PK profile on methylone's therapeutic index needs to be assessed. Similar to the parent compound, efficacy of the prodrug is tested in vivo in rats in the forced swim test to assess antidepressant-like activity and in fear extinction, a PTSD model, in order to establish a therapeutic dose range. To assess cardiovascular effects, a tail cuff method is used to monitor rats' heart rate and blood pressure at effective doses established in the behavioral tests and compared to parent methylone.

Parent methylone has shown antidepressant-like activity in the rat forced swim test (Warner-Schmidt et al, 2023) and enhances fear extinction, consistent with a beneficial effect in a mouse model of PTSD (Yu et al, 2022). These three tests are used to assess the activity of the prodrug compared to vehicle- or methylone-treated controls. For all studies, groups are compared using ANOVA and appropriate post-hoc tests using Graphpad Prism 9 software. Statistical significance is set at $p<0.05$. Outliers are defined as individual values lying more than 2 standard deviations off the mean and will be removed from the analysis.

Forced Swim Test: To test the antidepressant-like effect of the methylone prodrug compared with parent methylone, male Sprague Dawley (SD) rats, weighing 180-200 g on arrival, are subjected to the FST. Briefly, rats (N=6-8 per group) are subjected to a 15 min training swim 24 h before a 5 min FST testing session. Prodrug (at 5 doses selected based on PK profile), parent methylone (10 mg/kg) or vehicle control are administered 30 min prior to testing. Immobility is scored for the duration of the 5 min testing session. Reduced immobility is reflective of antidepressant-like responses. Predicted effective doses of the prodrug are identified based on the difference in immobility time between treated animals and controls.

Fear Extinction: Fear conditioning is a model of PTSD in which a traumatic memory is formed after a single presentation (e.g., association between tone and painful foot shock). Drugs that facilitate the extinction of fear conditioning (i.e., unlearning of the traumatic memory) are predicted to have therapeutic benefit in PTSD. A single dose of methylone (30 mg/kg) has been shown to enhance fear extinction in mice. To test whether the prodrug maintains this beneficial effect of methylone, male C57BL/6 mice (N=10-12 per group) are tested in a fear conditioning experiment. Briefly, mice are exposed to cued fear conditioning on day 1 (one CS—US) presentation in context A), fear extinction training on day 2 (6 CS presentations in context B) and extinction testing on day 3 (6 CS presentations in context B). Prodrug (5 doses selected based on PK profile), parent methylone (10 mg/kg) or vehicle control are administered 30 min prior to extinction training. Freezing behavior is scored as an indicator of the mouse's memory for the CSS—U association. Methylone significantly reduces freezing behavior on day 3, indicating a facilitation of extinction recall. The effect of the prodrug on time spent freezing to the CS presentations on day 3 is compared to vehicle- or methylone-treated controls.

Assessment of heart rate and blood pressure: Male SD rats are dosed once orally with prodrug (3-5 doses determined by results of FST), methylone positive control or vehicle negative control, Blood pressure parameters are assessed in the animals using a Visitech BP-2000 Tail Cuff Apparatus. The following parameters are acquired or calculated: (1) Systolic pressure (SP, primary); (2) Diastolic pressure (DP, primary); (3) Average pressure=(SP+DP)/2; (4) Mean arterial pressure (MAP)=DP+(SP−DP)/3 (approximate); (5) Pulse pressure=SP−DP; and (6) Heart rate (HR); derived from peak pulse pressure.

One week prior to the day on which test article (prodrug) and positive control (methylone) reagent are assessed for blood pressure effects, the animals are trained in the tail cuff apparatus for 5 sessions over 5 days. On the testing after which the vehicle or the test agent is administered and blood pressure evaluated at 9 time points relative to dosing (−60, 15, 30, 45, 60, 75, 90, 105, 120 min). Differences between vehicle control, methylone and each prodrug treatment group are determined by one-way ANOVA with Dunnett's multiple comparison test using GraphPad Prism with an alpha threshold of 0.05. Differences between prodrug and methylone groups are particularly relevant to show improvement in cardiovascular effects by the prodrug.

Conducting IND-Enabling Pre-Clinical Studies to Dose Patients in the Clinic:

A methylone prodrug is scaled-up, purified and formulated into GMP batches, and a non-clinical toxicology program is initiated in two species: rats and dogs. A 7-day dose-range finding study is followed by a 28-day GLP toxicology study to assess clinical signs and histopathology at three dose levels in both species. Bioanalytical testing in these animals is conducted to determine the PK profile in both species. Mutagenic potential and genotoxicity is evaluated by an Ames study and chromosomal aberration (in vitro micronucleus) testing. Cardiac safety is demonstrated in a cardiovascular safety study in dogs and supported by a hERG assay (in vitro). Additional in vivo safety pharmacology includes an in vivo micronucleus study and respiratory and CNS studies in rats. These studies follow ICH and FDA guidance, matching studies conducted for parent methylone.

Formulation of R&D and GMP Batches: Pisgah Laboratories begins R&D formulation optimization after identification of a prodrug candidate. Identity and structural confirmation are performed using HPLC, FTIR, proton ($^1$H) nuclear magnetic resonance spectroscopy (NMR), carbon-13 ($^{13}$C) NMR, and liquid-chromatography-mass spectroscopy (LC-MS). A route of synthesis which consistently results in a prodrug that is ≥95% pure with a yield ≥85% is selected for scale up batches. Initial scale up production is completed under R&D conditions (e.g., 50 g scale on a methylone basis), Results from synthesis optimization and initial scale up batches are used to determine potential impurities and form the foundation of stability measures. Following successful synthesis of the prodrug during R&D processes, material is scaled to a larger scale (e.g., 500 g on a methylone basis) under CGMP conditions. The material produced under the CGMP conditions is used for the IND enabling studies.

IND Enabling Studies: For all in vivo studies, Sprague Dawley rats or beagle dogs are used, consistent with IND-enabling studies performed previously with parent methylone. All studies are performed under GLP conditions except for the initial dose range finding studies in rat and dog.

Model selection and rationale: Rats are selected because they are a commonly used species for nonclinical research an accepted rodent species for nonclinical toxicity evaluations by regulatory agencies. Rodents show reproducible growth rates under laboratory conditions, are reasonably free from extraneous diseases, and have a low level of spontaneous abnormalities. The total number of animals is the minimum needed to properly characterize responses related to methylone hydrochloride administration and, thus, to meet experimental objectives. No alternative test systems exist which have been adequately validated to permit replacement of the use of live animals in this study. Every effort is made to obtain the maximum amount of information while reducing to a minimum the number of animals required for this study. The beagle is selected because the beagle is the usual non-rodent model used for evaluating the toxicity of various test article and for which there is a large historical database. The total number of animals to be used in these studies is considered to be the minimum required to properly characterize the effects of the test article and is designed such that it does not require an unnecessary number of animals to accomplish its objectives.

Toxicology Studies:

Dose range finding (DRF) studies in rat and dog: Four groups (N=5 per sex per group) of main study animals and corresponding satellite TK study animals (N=6 per sex per group) are dosed once by oral gavage on day1 and again on day 8 to determine tolerability of four different doses of prodrug selected based on results from pharmacokinetic analysis and results from efficacy and cardiovascular studies run above. The same study design applies to a DRF study in beagle dogs (N=2 per sex per group for main study and another N=2 per sex per group for TK analysis). In-life procedures (mortality/cage-side observations, clinical cage-side observations, body weights, food consumption, and ophthalmic examinations), clinical pathology (hematology, coagulation, clinical chemistry, urinalysis), bioanalysis and toxicokinetic evaluation, terminal necropsy (gross pathology) are evaluated for all animals in accordance with standard procedures, statistical analyses and in line with FDA guidance. Results inform dose selection for all in vivo IND-enabling studies.

28-day toxicology study in rat and dog: The objective is to determine the potential toxicity of the prodrug when given once weekly for four weeks. A four-week study of the prodrug by oral gavage in rats and dogs with a 14-day recovery period is run according to standard protocols, like a study run with parent methylone. There are four groups (3 dose levels+vehicle) of male and female rats (N=10 per sex per group for main study; N=5 per sex per group for recovery study) and a corresponding satellite cohort of animals for TK analysis (N=3 per sex per group for vehicle; 9 per sex per group for drug-treated). Prodrug is administered by oral gavage on days 1, 8, 15, and 22, consistent with studies of parent methylone. The same experimental design applies to the 28-day study in beagle dogs (N=4 per sex per group for main study; N=2 per sex per group for recovery study). All procedures are conducted under GLP conditions. In-life procedures (mortality/cage-side observations, clinical cage side observations, detailed clinical observations, body weights, food consumption, and ophthalmic examinations), clinical pathology (hematology, coagulation, clinical chemistry, urinalysis), bioanalysis and toxicokinetic evaluation, terminal necropsy (tissue collection, organ weights, histopathology, and microscopic evaluation) are evaluated for all animals (main study and recovery) in accordance with standard procedures, statistical analyses and in line with FDA guidance.

Ames Study (Bacterial Reverse Mutation): The purpose of this study is to evaluate the mutagenic potential of the prodrug to induce reverse mutations in the histidine operon of S. typhimurium strains TA98, TA100, TA1535, and TA1537 and the tryptophan operon of E. coli strain WP2 uvrA. Prodrug, appropriate positive controls (ICR, 2NF, SA, NQNO, and 2AA), and negative control (vehicle) are run in triplicate with and without metabolic activation mixture S9. In the absence of toxicity or solubility limitations, standard test article concentrations are 1.0, 5.0, 10, 50, 500, 1000, and 5000 pg/plate are used. After the 2-day incubation period, plates are evaluated for precipitation of the test article and thinning of the background lawn. The number of revertant colonies are counted and recorded. The test article is considered positive for mutagenicity if it induces an increase in mean revertants per concentration with increasing test article concentration that is at least 2-3× the vehicle control background frequency.

Rat micronucleus study: The objective is to determine potential genotoxicity of the prodrug when administered to rats by oral gavage for two days. A dose-range finding (DRF) phase determines tolerability to provide dose levels for the definitive study. For the DRF, three groups of rats (N=3 per group) treated with three doses of prodrug are evaluated for tolerability. For the main study, 5 groups of rats (N=5 per group) are treated with vehicle or 4 doses of prodrug (based on micronucleus DRF results) by oral gavage once daily for 2 days. Detailed cage-side and clinical observations take place pre-dose, post-dose and daily until termination 48 h post-dose. Micronucleus evaluation is by flow cytometry using peripheral blood using standard protocols. Criteria for a positive response: (1) at least 1 treatment group exhibits a statistically significant increase in % reticulocytes with micronuclei (MN-RETs) as compared with the concurrent negative control ($p<0.05$); and (2) the increase is dose-related ($p<0.05$); and (3) any increase is outside the 95% control interval of the historical negative control data. Criteria for a negative response: (1) no treatment group exhibits a statistically significant increase in % MN-RETs as compared with the concurrent negative control; and (2) there is no dose-related increase in % MN-RETs; and (3) all results are within the 95% control interval of the historical negative control data; and (4) bone marrow exposure to the test item has been demonstrated to occur.

Chromosomal Aberration (in vitro Micronucleus) Testing: This test evaluates the ability of a test article to break chromosomes to interfere with normal mitotic cell division. The objective of this study is to evaluate the potential of the prodrug to induce micronuclei in TK6 cells in the presence and absence of an exogenous metabolic activation system using short- and long-term treatments. Prodrug, vehicle control, or appropriate positive controls (cyclophosphamide monohydrate; mitomycin C, vinblastine sulfate) are evaluated using standard procedures. The target concentrations for the DRF study are 0.977, 1.95, 3.91, 7.81, 15.6, 31.3, 62.5, 125, 250, 500 µg/mL. All cultures are evaluated visually for signs of cytotoxicity, pH change, and precipitation at the time of dosing, wash, and prior to harvest. For the definitive study, single cultures are treated with vehicle, positive controls, and the 6 highest test article concentrations determined in the DRF. Criteria for a positive response are: (1) at least one of the test concentrations exhibits a statistically significant increase compared with the concurrent negative control; (2) the increase is dose-related; and (3) any of the results are outside the 95% control limit of the historical negative control distribution.

hERG Assay: The objective of this study is to examine the in vitro effects of prodrug on the hERG (human ether-à-go-go-related gene) channel current (a surrogate for $I_{Kr}$, the rapidly activating, delayed rectifier cardiac potassium current). The hERG is responsible for a rapid delayed rectifier current ($I_{Kr}$) in human ventricles. This channel has been selected for evaluation because inhibition of $I_{Kr}$ is the most common cause of cardiac action potential prolongation by non-cardiac drugs. Increased action potential duration causes prolongation of the QT interval and has been associated with a dangerous ventricular arrhythmia, torsade de pointes (TdP). In this assay, hERG potassium channels are expressed in a human embryonic kidney (HEK-293) cell line that lacks endogenous $I_{Kr}$. The concentration-response relationship of the effect of the prodrug on the hERG potassium channel current is evaluated at near-physiological temperature (35 to 37° C.). Percent inhibition at each concentration in the test group is compared with the vehicle control group using one-way ANOVA followed by Dunnett's multiple comparison Significant inhibition is defined at the level of $p<0.05$.

Core Battery of Safety Pharmacology Studies:

Dog cardiovascular (CV) study: The objective is to evaluate the potential CV effects of the prodrug in conscious, freely moving beagle dogs when dosed once via oral gavage at each dose level using a Latin square design. Four groups (N=4 male dogs per group) receive three different doses of prodrug or vehicle control. Hemodynamic endpoints, body temperature, and electrocardiogram (ECG) are monitored continuously at least 2 hours prior to dosing and for at least 24 hours post-dose via implanted telemetry devices. Interpretation of results are based on established safety thresholds per FDA guidance.

Rat respiratory study: The purpose of this study is to evaluate the potential acute respiratory effects of the prodrug in rats. Four groups of male rats (N=8 per group) are on-study. Parameters to be evaluated include respiratory rate, tidal volume, and minute volume. The animals are placed in the respiratory monitoring chambers at least 2.5 hours prior to dosing for acclimation and collection of pre-dose data. After at least 2.5 hours in the chambers, the animals are temporarily removed from the chambers for dosing with prodrug (3 dose levels) or vehicle. Immediately following dosing, the animals are returned to the chambers and respiratory monitoring is continued for a period of at least 6 hours. Data are collected continuously, logged into 1-minute time intervals, and reported in 15-minute time intervals during the course of the study. The effect of treatment over time is evaluated using a repeated measures analysis of covariance.

Rat CNS Study: The objective of this study is to evaluate the potential acute neurobehavioral effects of the prodrug. Four groups of male Sprague Dawley rats (N=8 per group) are treated with one of three doses of prodrug or vehicle. Neurobehavioral evaluations (activity, autonomic, excitability, neuromuscular, physiological, and sensorimotor) are conducted pre-dose (day −1) and at approximately 1.5, 6, and 24 h post-dose. Each animal is observed for 2 minutes in an opaque open-field observation box.

What is claimed is:

1. A compound of Formula (III):

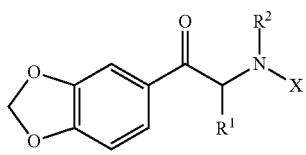

(III)

or a pharmaceutically acceptable salt thereof, wherein:
X is independently selected from the group consisting of:
(a) —C(O)OCH($R^4$)OP(O)O$R^{11}$(O$R^{12}$),
(b) —CH$_2$OC(O)$R^3$, and
(c) —C(O)(CH$_2$)$_n$Z$^a$$R^5$;
wherein:
n is 3 or 4;
$R^1$ and $R^2$ are each independently —C$_{1-6}$alkyl or —C$_{3-6}$cycloalkyl;
$R^3$ is selected from the group consisting of: —C$_{1-6}$alkyl, C$_{3-6}$cycloalkyl, —C$_{1-6}$haloalkyl, aryl, and heteroaryl;
$R^4$ is H, —C$_{1-6}$alkyl or C$_{3-6}$cycloalkyl;
$R^5$ is selected from the group consisting of: —C(O)$R^3$, —C(O)O$R^3$, —P(O)O$R^{11}$(O$R^{12}$), an amino acid, and a peptide;
$Z^a$ is O or N$R^4$;
$R^{11}$ and $R^{12}$ are each independently H, —C$_{1-6}$alkyl, —C$_{1-6}$heteroalkyl, —C$_{3-6}$cycloalkyl, —C$_{1-6}$haloalkyl, aryl or heteroaryl, wherein —C$_{1-6}$alkyl, —C$_{1-6}$heteroalkyl, —C$_{3-6}$cycloalkyl, —C$_{1-6}$haloalkyl, aryl or heteroaryl is unsubstituted or substituted with one or more —C$_{1-6}$alkyl, —C$_{1-6}$heteroalkyl, —C$_{3-6}$cycloalkyl, —C$_{1-6}$haloalkyl, aryl or heteroaryl.

2. The compound according to claim 1, wherein $R^1$ and $R^2$ are each independently methyl or ethyl.

3. The compound according to claim 1, wherein $R^4$ is H or methyl.

4. A compound of Formula (V):

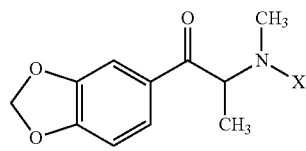

(V)

or a pharmaceutically acceptable salt thereof, wherein
X is independently selected from the group consisting of:
(a) —C(O)OCH($R^4$)OP(O)O$R^{11}$(O$R^{12}$),
(b) —CH$_2$OC(O)$R^3$, and
(c) —C(O)(CH$_2$)$_n$Z$^a$$R^5$;
wherein:
n is 3 or 4;
$R^3$ is selected from the group consisting of: —C$_{1-6}$alkyl, C$_{3-6}$cycloalkyl, —C$_{1-6}$haloalkyl, aryl, and heteroaryl;
$R^4$ is H, —C$_{1-6}$alkyl or C$_{3-6}$cycloalkyl;
$R^5$ is selected from the group consisting of: —C(O)$R^3$, —C(O)O$R^3$, —P(O)O$R^{11}$(O$R^{12}$), an amino acid, and a peptide;
$Z^a$ is O or N$R^4$;
$R^{11}$ and $R^{12}$ are each independently H, —C$_{1-6}$alkyl, —C$_{1-6}$heteroalkyl, —C$_{3-6}$cycloalkyl, —C$_{1-6}$haloalkyl, aryl or heteroaryl, wherein —C$_{1-6}$alkyl, —C$_{1-6}$heteroalkyl, —C$_{3-6}$cycloalkyl, —C$_{1-6}$haloalkyl, aryl or heteroaryl is unsubstituted or substituted with one or more —C$_{1-6}$alkyl, —C$_{1-6}$heteroalkyl, —C$_{3-6}$cycloalkyl, —C$_{1-6}$haloalkyl, aryl or heteroaryl.

5. The compound according to claim 4, wherein $R^4$ is H or methyl.

6. The compound according to claim 1, wherein X is

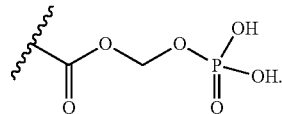 [SMILES: *C(=O)OCOP(=O)(O)O]

7. A compound of Formula (46):

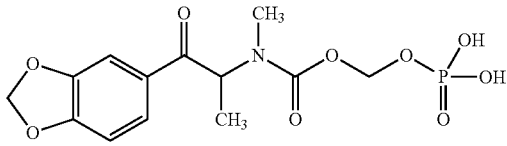

(46)

or a pharmaceutically acceptable salt thereof.

8. A pharmaceutical composition comprising a compound according to claim 1 or a pharmaceutically acceptable salt thereof; and a pharmaceutically acceptable carrier.

* * * * *